US008765704B1

(12) United States Patent
Han et al.

(10) Patent No.: US 8,765,704 B1
(45) Date of Patent: *Jul. 1, 2014

(54) MODIFIED SMALL INTERFERING RNA MOLECULES AND METHODS OF USE

(75) Inventors: Jang Han, Lafayette, CA (US); Michael Houghton, Emeryville, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/325,308

(22) Filed: Dec. 14, 2011

Related U.S. Application Data

(62) Division of application No. 11/664,008, filed on Feb. 28, 2008, now Pat. No. 8,138,161.

(51) Int. Cl.
*A61K 48/00* (2006.01)
*C07H 21/02* (2006.01)
*C07H 21/04* (2006.01)

(52) U.S. Cl.
USPC ............ 514/44; 536/23.1; 536/536; 536/24.5

(58) Field of Classification Search
CPC ..................... C12N 2310/14; C12N 2310/321; C12N 15/111; A61K 2300/00
See application file for complete search history.

(56) References Cited

U.S. PATENT DOCUMENTS

| | | | |
|---|---|---|---|
| 5,610,054 A | 3/1997 | Draper | |
| 6,107,027 A | 8/2000 | Kay et al. | |
| 6,133,246 A | 10/2000 | McKay et al. | |
| 6,174,868 B1 | 1/2001 | Anderson et al. | |
| 6,506,559 B1 | 1/2003 | Fire et al. | |
| 7,718,632 B2 | 5/2010 | Van Heeke et al. | |
| 2003/0143732 A1 | 7/2003 | Fosnaugh et al. | |
| 2003/0153519 A1 | 8/2003 | Kay et al. | |
| 2003/0206887 A1 | 11/2003 | Morrissey et al. | |
| 2003/0219823 A1 | 11/2003 | Alsobrook, II et al. | |
| 2004/0192626 A1 | 9/2004 | McSwiggen et al. | |
| 2004/0209831 A1 | 10/2004 | McSwiggen et al. | |
| 2005/0085528 A1 | 4/2005 | Ahola et al. | |
| 2005/0209180 A1 | 9/2005 | Jadhav et al. | |
| 2005/0255487 A1 | 11/2005 | Khvorova et al. | |
| 2011/0166058 A1 | 7/2011 | Hinkle et al. | |

FOREIGN PATENT DOCUMENTS

| | | |
|---|---|---|
| EP | 1 532 248 B1 | 5/2005 |
| WO | WO 03/079757 A2 | 10/2003 |
| WO | WO 2004/009769 A2 | 1/2004 |
| WO | WO 2004/011647 A1 | 2/2004 |
| WO | WO 2004/042024 A2 | 5/2004 |
| WO | WO 2004/065546 A2 | 8/2004 |
| WO | WO 2004/065601 A2 | 8/2004 |
| WO | WO 2005/112636 A2 | 12/2005 |
| WO | WO 2007/076328 A2 | 7/2007 |

OTHER PUBLICATIONS

Czauderna, et al.; "Structural variations and stabilising modifications of synthetic siRNAs in mammalian cells"; Nucleic Acids Research; 31(11):2705-2716 (2003).
Dias, et al.; "Antisense Oligonucleotides: Basic Concepts and Mechanisms"; Mol. Cancer Ther.; 1:347-355 (2002).
Doherty, et al.; "Ribozyme Structures Andmechanisms"; Annu. Rev. Biophys. Biomol. Struct.; 30:457-475 (2001).
Dorsett, et al.; siRNAs: Applications in Functional Genomics and Potential As Therapeutics; Nature Reviews—Drug Discovery; 3:318-329 (2004).
Elbashir, et al.; "Duplexes of 21 nucleotide RNAs mediate RNA interference in cultured mammalian cells"; Nature—Letters to Nature; 411:494-498 (2001).
Elbashir, et al.; "Functional anatomy of siRNAs for mediating efficient RNAi in *Drosophila melanogaster* embryo lysate"; The EMBO Journal; 20(23):6877-6888 (2001).
Elbashir, et al.; "RNA interference is mediated by 21- and 22-nucleotide RNAs"; Genes Dev.; 15:188-200 (2001).
Jarczak, et al.; "Hairpin ribozymes in combination with siRNAs against highly conserved hepatitis C virus sequence inhibit RNA replication and protein translation from hepatitis C virus subgenomic replicons"; FEBS Journal; 272:5910-5922 (2005).
Guerniou, et al.; "Targeted inhibition of the hepatitis C internal ribosomal entry site genomic RNA with oligonucleotide conjugates"; Nucleic Acids Research; 35(20):6778-6787 (2007).
Kapadia, et al.; "Interference of hepatitis C virus RNA replication by short interfering RNAs"; PNAS; 100(4): 2014-2018 (2003).
Kawasaki, et al.; "World of small RNAs: from ribozymes to siRNA and miRNA"; Differentiation; 72:58-64 (2004).
Kim, et al.; "Inhibition of hepatitis C virus gene expression by small interfering RNAs using a tri-cistronic full-length viral replicon and a transient mouse model"; Virus Research; 122:1-10 (2006).
Kraynack, et al.; "Small interfering RNAs containing full 2'-O-methylribonucleotide-modified sense strands display Argonaute2/eIF2C2-dependent activity"; RNA; 12(1):163-176 (2006).
Kruger, et al.; "Involvement of Proteasome Alpha-Subunit PSMA7 in Hepatitis C Virus Internal Ribosome Entry Site-Mediated Translation"; Molecular and Cellular Biology; 21(24):8357-8364 (2001).
Lee, et al.; "Pharmacokinetics and Tissue Distribution of a Ribozyme Directed Against Hepatitis C Virus RNA Following Subcutaneous or Intravenous Administration in Mice"; Hepatology; 32(3):640-646 (2000).

(Continued)

*Primary Examiner* — Amy Bowman
(74) *Attorney, Agent, or Firm* — Frank Wu

(57) ABSTRACT

The present invention provides double-stranded RNA molecules that mediate RNA interference in target cells, preferably hepatic cells. The invention also provides double-stranded RNA (dsRNA) molecules that are modified to be resistant to nuclease degradation, which inactivates a virus, and more specifically, hepatitis C virus (HCV). The invention also provides a method of using these modified RNA molecules to inactivate virus in mammalian cells and a method of making modified small interfering RNAs (siRNAs) using human Dicer. The invention provides modified RNA molecules that are modified to include a dsRNA or siRNA wherein one or more of the pyrimidines in the RNA molecule are modified to include 2'-Fluorine. The invention also provides dsRNA or siRNA in which all pyrimidines are modified to include a 2'-Fluorine. The invention provides that the 2'-Fluorine dsRNA or siRNA molecule is further modified to include a two base deoxynucleotide "TT" sequence at the 3' end of the molecule.

18 Claims, 29 Drawing Sheets

(56) References Cited

OTHER PUBLICATIONS

Lieber, et al.; "Elimination of Hepatitis C Virus RNA in Infected Human Hepatocytes by Adenovirus-Mediated Expression of Ribozymes"; Journal of Virology; 70(12):8782-8791 (1996).

Macejak, et al.; "Inhibition of Hepatitis C Virus (HCV)-RNA-Dependent Translation and Replication of a Chimeric HCV Poliovirus Using Synthetic Stabilized Ribozymes"; Hepatology; 31(3):769-776 (2000).

Macejak, et al.; "Enhanced antiviral effect in cell culture of type 1 interferon and ribozymes targeting HCV RNA"; Journal of Viral Hepatitis; 8:400-405 (2001).

Martinand-Mari, et al.; "Oligonucleotide-based Strategies to Inhibit Human Hepatitis C Virus"; Oligonucleotides—Review; 13:539-548 (2003).

Miyagishi, et al.; "Comparison of the Suppressive Effects of Antisense Oligonucleotides and siRNAs Directed Against the Same Targets in Mammalian Cells"; Antisense and Nucleic Acid Drug Development; 13:1-7 (2003).

Ohkawa, et al.; "Cleavage of viral RNA and inhibition of viral translation by hepatitis C virus RNA-specific hammerhead ribozyme in vitro"; Journal of Hepatology; 27:78-84 (1997).

Peracchi; "Prospects for antiviral ribozymes and deoxyribozymes"; Rev. Med. Virol.—Review; 14:47-64 (2004).

Puerta-Fernandez, et al.; "Ribozymes: recent advances in the development of RNA tools"; FEMS Microbiology Reviews; 27:75-97 (2003).

Randall, et al.; "Clearance of replicating hepatitis C virus replicon RNAs in cell culture by small interfering RNAs"; PNAS; 100(1):235-240 (2003).

Ryu, et al.; "Identification of the Most Accessible Sites to Ribozymes on the Hepatitis C Virus Internal Ribosome Entry Site"; Journal of Biochemistry and Molecular Biology; 36(6):538-544 (2003).

Ryu, et al.; "Note: Comparative Analysis of Intracellular Trans-Splicing Ribozyme Activity Against Hepatitis C Virus Internal Ribosome Entry Site"; The Journal of Microbiology; 42(4):361-364 (2004).

Sakamoto, et al.; "Intracellular Cleavage of Hepatitis C Virus RNA and Inhibition of Viral Protein Translation by Hammerhead Ribozymes"; J. Clin. Invest.; 98:2720-2728 (1996).

von Weizsacker, et al.; "Gene Therapy for Chronic Viral Hepatitis: Ribozymes, Antisense Oligonucleotides, and Dominant Negative Mutants"; Hepatology—Concise Review; 26(2):251-255 (1997).

Wang, et al.; "Subsection E: Methods of RGS Protein Inhibition—[15] Ribozyme- and siRNA-Mediated Suppression of RGS-Containing RhoGEF Proteins"; Methods in Enzymology; 389:244-265 {2004}.

Welch, et al.; "Ribozyme gene therapy for hepatitis C virus infection"; Clinical and Diagnostic Virology; 10:163-171 (1998).

Yu, et al.; "Activity of HDV ribozymes to trans-cleave HCV RNA"; World J. Gastroenterol.; 8(4):694-698 (2002).

J. Tang et al., "The Large 386-nt Deletion in SARS-Associated *Coronavirus*: Evidence for Quasispecies?", The Journal of Infectious Diseases, 194:808-813 (2006).

L. Delang et al., "Statins Potentiate the In Vitro Anti-Hepatitis C Virus Activity of Selective Hepatitis C Virus Inhibitors and Delay or Prevent Resistance Development", Hepatology, 50(1):6-16 (2009).

T. Bader et al., "Fluvastatin Inhibits Hepatitis C Replication in Humans", American Journal of Gastroenterology, 103:1383-1389 (2008).

M. Segarra-Newnham et al., "Effectiveness and Hepatotoxicity of Statins in Men Seropositive for Hepatitus C Virus", Pharmacotherapy, 27(6):845-851 (2007).

C. Argo et al., "Statins in Liver Disease: A Molehill, an Iceberg, or Neither?", Hepatology, 48:662-669 (2008).

J. Ye et al., "Disruption of hepatitus C virus RNA replication through inhibition of host protein geranylgeranylation", PNAS, 100(26):15865-15870 (2003).

K. Gibson et al., "Experience With Use in Patients With Chronic Hepatitus C Infection", Am J Cardiol, 96:1278-1279 (2005).

THE REGION WHERE siRNAs WAS DESIGNED IS BOXED.
THE SEQUENCE OF THE 21-bp siRNA$_5$ IS SHOWN BELOW.

```
            286                    304
siRNA5   5'-GUACUGCCUGAUAGGGUGCUU
            UUCAUGACGGACUAUCCCACG-5'
GL2      5'-CGUACGCGGAAUACUUCGAUU
            UUGCAUGCGCCUUAUGAAGCU-5'
GL3      5'-CUUACGCUGAGUACUUCGAUU
            UUGAAUGCGACUCAUGAAGCU--5'
SIN      5'-AUCUCUACGGUGGUCCUAAUU
            UUUAGAGAUGCCACCAGGAUU--5'
```

Fig. 2

| | Domain | sequence (NN-N19-NN) | Position | | |
|---|---|---|---|---|---|
| 5U6 | 5UTR | cc-CUGUGAGGAACUACUGUCU-uc | 45-63 | sense | CUGUGAGGAACUACUGUCUU |
| | | | | antisense | AGACAGUAGUUCCUCACAGG |
| 5U9 | | ua-CUGUCUUCACGCAGAAAGC-gu | 58-76 | sense | CUGUCUUCACGCAGAAAGCU |
| | | | | antisense | GCUUUCUGCGUGAAGACAGUA |
| 5U10 | | cg-AGACUGCUAGCCGAGUAGU-gu | 244-262 | sense | AGACUGCUAGCCGAGUAGUGU |
| | | | | antisense | ACUACUCGGCUAGCAGUCUCG |
| C1 | Core | ga-AUCCUAAACCUCAAAGAAA-aa | 352-379 | sense | AUCCUAAACCUCAAAGAAAA |
| | | | | antisense | UUUCUUUGAGGUUUAGGAUUC |
| C2 | | gg-UCAGAUCGUCGGUGGAGUU-ua | 425-443 | sense | UCAGAUCGUCGGUGGAGUUA |
| | | | | antisense | AACUCCACCGACGAUCUGACC |
| C3 | | gg-UAAGGUCAUCGAUACCCUC-ac | 701-719 | sense | UAAGGUCAUCGAUACCCUCAC |
| | | | | antisense | GAGGGUAUCGAUGACCUUACC |
| C4 | | ac-GGCGUGAACUAUGCAACAG-gg | 822-840 | sense | GGCGUGAACUAUGCAACAGGG |
| | | | | antisense | CUGUUGCAUAGUUCACGCCGU |
| C5 | | cc-GGUUGCUCCUUUUCUAUCU-uc | 852-870 | sense | GGUUGCUCCUUUUCUAUCUUC |
| | | | | antisense | AGAUAGAAAAGGAGCAACCGG |
| 5B1 | NS5B | gc-UCUUCAUACGGAUUCCAAU-ac | 6163-6181 | sense | UCUUCAUACGGAUUCCAAUAC |
| | | | | antisense | AUUGGAAUCCGUAUGAAGAGC |
| 5B2 | | ca-UACGGAUUCCAAUACUCUC-cu | 6167-6187 | sense | UACGGAUUCCAAUACUCUCCU |
| | | | | antisense | GAGAGUAUUGGAAUCCGUAUG |
| 5B3 | | uu-UGACUCAACGGUCACUGAG-aa | 6270-8286 | sense | UGACUCAACGGUCACUGAGAA |
| | | | | antisense | CUCAGUGACCGUUGAGUCAA |
| 5B4 | | cc-UUCACGGAGGCUAUGACUA-gg | 8813-8901 | sense | UUCACGGAGGCUAUGACUAGA |
| | | | | antisense | UAGUCAUAGCCUCCGUGAAGG |
| 5B5 | | au-ACGACUUGGAGUUGAUAAC-au | 8871-8889 | sense | ACGACUUGGAGUUGAUAACAU |
| | | | | antisense | GUUAUCAACUCCAAGUCGUAU |
| 5B6 | | au-UCCUGGCUAGGCAACAUCA-uc | 8817-8835 | sense | UCCUGGCUAGGCAACAUCAUC |
| | | | | antisense | UGAUGUUGCCUAGCCAGGAAU |
| 5B7 | | uu-GUGGCAAGUACCUCUUCAA-cu | 9160-9178 | sense | GUGGCAAGUACCUCUUCAACU |
| | | | | antisense | UUGAAGAGGUACUUGCCACAA |
| 5B8 | | au-GUGGUGCCUACUCCUACUU-uc | 9317-9335 | sense | GUGGUGCCUACUCCUACUUUC |
| | | | | antisense | AAGUAGGAGUAGGCACCACAU |
| 3U1 | 3UTR | cu-UUGGUGGCUCCAUCUUAGC-cc | 9506-9524 | sense | UUGGUGGCUCCAUCUUAGCCC |
| | | | | antisense | GCUAAGAUGGAGCCACCAAAG |
| 3U2 | | gu-CACGGCUAGCUGUGAAAGG-uc | 9531-9549 | sense | CACGGCUAGCUGUGAAAGGUC |
| | | | | antisense | CCUUUCACAGCUAGCCGUGAC |
| 3U3 | | ag-CCGCUUGACUGCAGAGAGU-gc | 9556-9579 | sense | CCGCUUGACUGCAGAGAGUGC |
| | | | | antisense | ACUCUCUGCAGUCAAGCGGCU |

Fig. 3

```
   1 ttattaggtt ttacctacc caggaaaagc caaccaacct cgatctcttg tagatctgtt
  61 ctctaaacga actttaaaat ctgtgtagct gtcgctcggc tgcatgccta gtgcacctac
 121 gcagtataaa caataataaa tttactgtc gttgacaaga aacgagtaac tcgtccctct
 181 tctgcagact gcttacggtt tcgtccgtgt tgcagtcgat catcagcata cctaggtttc
 241 gtccgggtgt gaccgaaagg taagatggag agccttgttc tggtgtcaa cgagaaaaca
 301 cacgtccaac tcagtttgcc tgtccttcag gttagagacg tgctagtgcg tggctcggg
 361 gactctgtgg aagaggccct atcggaggca cgtgaacacc tcaaaaatgg cactgtggt
 421 ctagtagagc tggaaaaagg cgtactgccc cagctgaac agccctatgt gttcattaaa
 481 cgttctgatg cctaagcac caatcacggc cacaaggtcg ttgagctggt tgcagaaatg
 541 gacggcattc agtacggtcg tagcggtata acactggag tactcgtgcc acatgtgggc
 601 gaaacccaa ttgcatacccg caatgttctt cttcgtaaga acggtaataa gggagccggt
 661 ggtcatagct atggcatcga tctaaagtct tatgacttag gtgacgagct tggcactgat
 721 cccattgaag attatgaaca aaactggaac actaagcatg gcagtggtgc actccgtgaa
 781 ctcactcgtg agctcaatgg aggtgcagtc actcgctatg tcgacaacaa ttctcgtggc
 841 ccagatgggt accctcttga ttgcatcaaa gattttctcg cacgcgcggg caagtcaatg
 901 tgcactcttt ccgaacaact tgattacatc gagtcgaaga gaggtgtcta ctgctgcgt
 961 gaccatgagc atgaaattgc ctggttcact gagcgctctg ataagagcta cgagcaccag
1021 acacccttcg aaattaagag tgccaagaaa tttgacactt tcaaggggga atgcccaaag
1081 ttgtgttttc ctcttaactc aaaagtcaaa gtcattcaac cacgtgttga aagaaaaag
1141 actgagggtt tcatggggcg tatacgctct gtgtaccctg ttgcatctcc acaggagtgt
1201 aacaatatgc acttgtctac cttgatgaaa tgtaatcatt gcgatgaagt ttcatggcag
1261 acgtgcgact ttctgaaagc cactgtgaa ccttgtggca ctgaaaattt agttattgaa
1321 ggacctacta catgtgggta cctacctact aatgctgtag tgaaaatgcc atgtcctgcc
1381 tgtcaagacc cagagattgg acctgagcat agtgttgcag attatcacaa ccactcaaac
1441 atgaaactc gactccgcaa gggaggtagg actagatgtt ttggaggctg tgtgtttgcc
1501 tatgtggct gctataaataa gcgtgcctac tgggttcctc gtgctagtgc tgatattggc
1561 tcaggccata ctggcattac tggtgacaat gtggagaccct tgaatgagga tctccttgag
1621 atactgagtc gtgaacgtgt taacattaac attgtttggcg attttcattt gaatgaagag
1681 gttgccatca tttggcatc ttttctctgct tctacaagtg ccttttatga cactataaag
1741 agtctgatt acaagtcttt caaaaccatt gttgagtcct gcggtaaacta taaagttacc
1801 aagggaaagc ccgtaaaagg tgctggaaac attggacaac agagatcagt tttaacacca
1861 ctgtgtggtt ttccctcaca ggctgctggt gttatcagat caattttgc gcgcacactt
1921 gatgcagcaa accactcaat tcctgatttg caaagagcag ctgtcaccat actgatggt
1981 attctgaac agtcattacg tcttgcgac gccatggttt atacttcaga cctgctcacc
2041 aacagtgtca ttattaggc atatgtaact ggtggtctg tacaacagac ttctcagtgg
2101 ttgtctaatc ttttgggcac tactgttgaa aaactcaggc ctatcttga atggattgag
2161 gcgaaactta gtgcaggagt tgaattctc aaggatgctt gggagattct caaatttctc
2221 attacaggtg tttttgacat cgtcaagggt caaatacagg ttgcttcaga taacatcaag
2281 gattgtgtaa aatgcttcat tgatgtgtt aacaaggcac tcgaaatgtg cattgatcaa
2341 gtcactatcg ctggcgcaaa gttgcgatca ctcaacttag gtgaagtctt catcgctcaa
2401 agcaagggac tttaccgtca gtgtatacgt ggcaaggagc agctgcaact actcatgcct
2461 cttaaggcac caaaagaagt aacctttctt gaaggtgatt cacatgacac agtacttacc
2521 tctgaggagg ttgttctcaa gaacggtgaa ctcgaagcac tcgagacgcc cgttgatagc
2581 ttcacaaatg gagctatcgt cggcacacca gtctgtgtaa atggcctcat gctcttagag
2641 attaaggaca aagaacaata ctgcgcattg tctcctggtt tactggctac aaacaatgtc
2701 tttcgcttaa aaggggggtgc accaattaaa ggtgtaacct tggagaagaa tactgtttgg
2761 gaagttcaag gttacaagaa tgtgagaatc acattgagc ttgatgaacg tgttgacaaa
```

(cont.)

```
2821 gtgctaatg aaaagtgctc tgtctacact gttgaatccg gtaccgaagt tactgagttt
2881 gcatgtgttg tagcagaggc tgttgtgaag actttacaac cagtttctga tctcottacc
2941 aacatgggta ttgatcttga tgagtggagt gtagctacat tctacttatt tgatgatgct
3001 ggtgaagaaa acttttcatc acgtatgtat tgttcctttt acccttccaga tgaggaagaa
3061 gaggacgatg cagagtgtga ggaagaagaa attgatgaaa cctgtgaaca tgagtacggt
3121 acagaggatg attatcaagg tctccctctg gaatttggtg cctcagctga aacagttcga
3181 gttgaggaag aagaagagga agactggctg gatgatacta ctgagcaatc agagattgag
3241 ccagaaccag aacctacacc tgaagaacca gttaatcagt ttactggtta tttaaaactt
3301 actgacaatg ttgccattaa atgtgttgac atcgttaagg aggcacaaag tgctaatcct
3361 atggtgattg taaatgctgc taacatacac ctgaaacatg gtggtggtgt agcaggtgca
3421 ctcaacaagg caaccaatgg tgccatgcaa aaggagagtg atgattacat taagctaaat
3481 ggccctctta cagtaggagg gtcttgtttg cttctggac ataatcttgc taagaagtgt
3541 ctgcatgttg ttggacctaa cctaaatgca ggtgaggaca tccagcttct taaggcagca
3601 tatgaaaatt tcaattcaca ggacatctta cttgcaccat tgtgtcagc aggcatattt
3661 ggtgctaaac cacttcagtc tttacaagtg tgcgtgcaga cggttcgtac acaggtttat
3721 attgcagtca atgacaaagc tctttatgag caggttgtca tggattatct tgataacctg
3781 aagcctagag tggaagcacc taaacaagag gagccaccaa acacagaaga ttccaaaact
3841 gaggagaaat ctgtcgtaca gaagcctgtc gatgtgaagc caaaaattaa ggcctgcatt
3901 gatgaggtta ccacaacact ggaagaaact aagttctctta caataagtt actcttgttt
3961 gctgatatca atggtaagct ttaccatgat tctcagaaca tgcttagagg tgaagatatg
4021 tctttccttg agaaggatgc acctacatg gtaggtgatg ttatcactag tggtgatatc
4081 actgtgttg taataccctc caaaaaggct ggtggcacta ctgagatgct ctcaagagct
4141 ttgaagaaag tgccagttga tgagtatata accacgtacc ctggacaagg atgtgctggt
4201 tatacacttg aggaagctaa gactgctctt aagaaatgca aatctgcatt ttatgtacta
4261 ccttcagaag cacctaatgc taaggaagag attctaggaa ctctatcctg gaattgaga
4321 gaaatgcttg ctcatgctga agagacaaga aaattaatgc ctatatgcat ggatgttaga
4381 gccataatgg caaccatcca acgtaagtat aaaggaatta aaattcaaga gggcatcgtt
4441 gactatggtg tccgattctt ctttatact agtaaagagc ctgtagcttc tattattacg
4501 aagctgaact ctctaaatga gccgctgtc acaatgccaa ttggttatgt gacacatggt
4561 tttaatcttg aagaggctgc gcgctgtatg cgttctctta agctcctgc cgtagtgca
4621 gtatcatcac cagatgctgt tactacatat aatggatacc tcactcgtc atcaaagaca
4681 tctgaggagc acttgtagaa aacagtttct tggctggct cttacagaga ttggtcctat
4741 tcaggacagc gtacagagtt aggtgttgaa tttcttaagc gtggtgacaa aattgtgtac
4801 cacactctgg agagcccgt cgagtttcat cttgacggtg aggttcttc actgacaaa
4861 ctaaagagtc tcttatccct gcgggaggtt aagactataa aagtgtcac aactgtggac
4921 aacactaatc tccacacaca gctgtggat atgtctatga catatggaca gcagttggt
4981 ccaacatact tggatggtgc tgatgttaca aaaattaaac ctcatgtaaa tcatgagggt
5041 aagcttttct tgtactacc tagtgatgac acactacgta gtgaagcttt cgagtactac
5101 catactcttg atgagagttt tcttggtagg tacatgtctg cttaaacca cacaaagaaa
5161 tggaaattc ctcaagtgg tggttaact tcattaaat gggctgataa caattgttat
5221 ttgtctagtg tttattago acttcaacag cttgaagtca aatcaatgc accagcactt
5281 caagaggctt attatagagc ccgtgctggt gatgctgcta actttgtgc actcatactc
5341 gcttacagta ataaaactgt tggcgagctt ggtgatgtca gagaaactat gacccatctt
5401 ctacagcatg ctaattggga atcgcaaaag cgagttctta atggtgtg taaacattgt
5461 ggtcagaaa ctactaccctt aacgggtgta gaagctgtga tgtatgggg tactctatct
5521 tatgataatc ttaagacagg tgtttccatt ccatgtgtgt gtgtcgtga tgctacacaa
5581 tatctagtac aacaagagtc ttcttttgtt atgatgctg caccacctgc tgagtataaa
5641 ttacagcaag gtacattctt atgtgcgaat gagtacactg gtaactatca gtgtggctat
5701 tacactcata taactgctaa ggagacccctc tatcgtattg acggagctca ccttacaaag
5761 atgtcagagt acaaggacc agtgactgat gttttctaca ggaaaacatc ttacactaca
5821 accatcaagc ctgtgtcgta taactctgat ggagttactt acacagagat tgaaccaaaa
5881 ttggatggtgt attataaaaa ggataatgct tactatacag agcagcctat agacctgta
5941 ccaacaac cattaccaaa tgcgagttt gataatttca aactcacatg ttctaacaca
6001 aaattgctg atgatttaaa tcaaatgaca ggcttcacaa gccagcttc acgagagcta
6061 tctgtcacat tctcccaga cttgaatggc gatgtagtgg ctattgacta tagacacacat
6121 tcagcgagtt tcaagaaagg tgctaaatta ctgcataagc caattgtttg gcacattaac
```

Fig. 3 (cont.)

```
6181 caggctacaa ccaagacaac gttcaaacca aacactggt gttacgttg tctttggagt
6241 acaaagccag tagatacttc aaattcattt gaagttctgg cagtagaaga cacacaagga
6301 atggacaatc ttgctgtga aagtcaacaa cccacctctg aagaagtagt ggaaaatcct
6361 accatacaga aggaagtcat agagtgtgac gtgaaaacta ccgaagttgt aggcaatgtc
6421 atacttaaac catcagatga aggtgttaaa gtaacacaag agtaggtca tgaggatctt
6481 atggctgctt atgtggaaaa cacaagcatt accattaaga aacctaatga gctttcacta
6541 gccttaggtt taaaaacaat tgccactcaa ggtattgctg caattaatag tgttcctttgg
6601 agtaaaattt tggcttatgt caaaccattc ttaggacaag cagcaattac aacatcaaat
6661 tcgctaaga gattagcaca acgtgtgttt aacaattata tgcctatgt gttacatta
6721 ttgtccaat tgtgtactt tactaaaagt accaattcta gaattagagc ttcactacct
6781 acaactattg ctaaaactag tgttaagagt gttgctaaat tatgttgga tgccggcatt
6841 aattatgtga agcacccaa atttctaaa tgttcacaa tcgctatgtg gctattgtg
6901 ttaagtattt gcttaggttc tctaatctgt gtaactgctg cttttggtgt actcttatct
6961 aatttggtg ctccttctta ttgtaatggc gttagagaat tgtatcttaa ttcgtctaac
7021 gtactacta tgggtattctg tgaaggttct tttcctgca gcattgttt aagtggattta
7081 gactcctg atcttatcc agctcttgaa accatcagg tgacgattc atcgtacaag
7141 ctagacttga caattttagg tctggccgct gagtgggttt ttgcatatat gttgttcaca
7201 aaattctttt atttattagg tcttcagct ataatgcagg tgtcttgg ctatttgct
7261 agtcattca tcagcaattc ttggctcatg tggtttatca ttagtattgt acaaatggca
7321 cccgttctg caatggttag gatgtacatc ttctttgct cttctacta catatggaag
7381 agctatgttc atatcatgga tggttgcacc tctcgaactt gcatgatgtg ctataagcgc
7441 aatcgtgcca cacgcgttga gtgtacaact atgttaatgt gcatgaagag atctttctat
7501 gctatgcaa atggaggcg tggcttctgc aagactcaca ttggaattg tctcaattgt
7561 gacacctttt gcactggtag tacattcatt agtgatgaag ttgctgtga ttgtcactc
7621 cagttaaaaa gaccaatcaa ccctactgac cagtcatgt atattgttga tagtgttgct
7681 gtgaaaaatg gcgcgcttca cctctactt gacaaggctg tcaaaagac ctatgagaga
7741 catccgctct cccatttgt caatttagac aatttgagag ctaacaacac taaaggtca
7801 ctgcctatta atgtcatagt tttgtggtc aagtccaaat gcgacgagtc tgctctaag
7861 tctgcttctg tgtactacag tcagctgatg tgccaaccta ttctgttgct tgaccaagct
7921 cttgtatcag acgtggaga tagtactgaa gtttccgtta agatgttga tgcttatgtc
7981 gacacctttt cagcaacttt tagtgttcct atggaaaaac ttaaggcact tgttgctaca
8041 gctcacagcg agttagcaaa gggtgtagct ttagatggtg tcttttctac attcgtgtca
8101 gctgccgac aaggtgttgt tgataccgat gttgacacaa aggatgttat tgaatgtctc
8161 aaacttcac atcactctga cttagaagtg acaggtgaca gttgtaacaa tttcatgctc
8221 acctataata aggttgaaaa catgacgccc agagatctg gcgcatgtat tgactgtaat
8281 gcaaggcata tcaatgccca agtagcaaaa agtcacaatg ttcactcat ctggaatgta
8341 aaagactaca tgtcttatc tgaacagctg cgtaaacaa ttcgtagtgc tgccagcagg
8401 aacaacatac ctttagact aacttgtgct acaactagac aggtgtcaa tgtcataact
8461 actaaaatct cactcaaggg tggtaagatt gttagtactt gtttaaaact tatgcttaag
8521 gccacattat tgtgcgttct tgctgcattg gttgttata tcgtatgcc agtacataca
8581 tgtcaatcc atgatggtta cacaaatgaa atcattggtt tcaaagccat tcaggatggt
8641 gtcactgtg acatcattc tactgatgat tgtttgcaa ataaacatgc tggtttgac
8701 gcatggtta gccagcgtgg tggttcatac aaaaatgaca aaagctgcc tgtagtagct
8761 gctatcatta caagcagagat tggtttcata gtgctggct taccgggtac tgtgctgaga
8821 gcaatcaatg gtgactctctt gcattttcta cctcgtgttt ttagtctgt tggcaacatt
8881 tgctacacac cttccaaact catgagtat agtgatttgc ctaccctctgc ttcgtctt
8941 gctgctgagt gtacaatttt taaggatgct atgggcaaac ctgtgccata ttgtttgac
9001 actaattgc tagagggtc tattcttat agtgagcttc gtccagacac tcgttatgtg
9061 cttatggatg gttccatcat acagtttcct aacacttacc tggagggtc tgttagagta
9121 gtaacaactt ttgatgctga gtactgtaga catggtacat gcgaaaggtc agaagtaggt
9181 atttgcctat ctaccagtgg tagatgggtt cttaataatg agcattacag agctctatca
9241 ggagtttct gtggtgtgga tgcgatgaat ctcatagcta acatctttac tcctctgtg
9301 caaacctgtg gtgcttaga tgtgtctgct tcagtagtgg ctggtgtat tattgccata
9361 ttgtgactt gtgctgccta ctacttatg aaattcagac gtgttttgg tgagtacaac
9421 catgtgttg ctgctaatgc actttgtgtt ttgatgtct tcactatact ctgctggtta
9481 ccagcttaca gcttctgcc gggagtctac tcagtctttt actgtactt gacattctat
```

Fig. 3 (cont.)

```
 9541 ttcaccaatg atgtttcatt cttggctcac cttcaatggt ttgccatgtt ttctcctatt
 9601 gtgcctttt ggataacagc aatctatgta ttctgtattt ctctgaagca ctgccattgg
 9661 ttcttaaca actatcttag gaaaagagtc atgtttaatg gagttacatt tagtacccttc
 9721 gaggaggctg ctttggtac cttttgctc aacaaggaaa tgtacctaaa attgcgtagc
 9781 gagacacctgt tgccacttac acagtataac aggtatcttg ctctatataa caagtacaag
 9841 tatttcagtg gagccttaga tactaccagc tatcgtgaag cagcttgctg ccacttagca
 9901 aaggctctaa atgactttag caactcaggt gctgatgttc tctaccaacc accacagaca
 9961 tcaatcactt ctgctgttct gcagagtggt tttaggaaaa tggcattccc gtcaggcaaa
10021 gttgaagggt gcatggtaca agtacctgt ggaactacaa ctcttaatgg atgtggttg
10081 gatgacacag tatactgtcc aagacatgtc attgcacag cagaagacat gcttaatcct
10141 aactatcaag atctgctcat tgcaaatcc aaccatagct ttctgttca ggctggcaat
10201 gtcaacttc gtgttattgg ccattctatg caaaattgtc tgcttaggct taaagtgat
10261 acttctaacc ctaagacacc caagtataaa ttgtccgta tccaacctgg tcaaacattt
10321 tcagttctag catgctacaa tggttcacca tctggtgttt atcagtgtgc catgagacct
10381 aatcatacca ttaaaggttc ttccttaat ggatcatgtg gtagtgtgg tttaacatt
10441 gattatgatt gcgtgtttt ctgctatatg catcatatgg agcttccaac aggagtacac
10501 gctggtactg acttagaagg taaattctat ggtccattg ttgacagaca aactgcacag
10561 gctgcaggta cagacacaac catacacatta aatgtttgg catggctgta tgctgctgtt
10621 atcaatggtg atagggtggtt tcttaataga ttcaccacta cttgaatga cttaaccctt
10681 gtggcaatga agtacaacta tgaaccttg acacaagatc atgttgacat attgggacct
10741 cttctgctc aaacaggaat tgccgtctta gatatgtgtg ctgcttgaa agagctgctg
10801 cagaatggta tgaatggtcg tactatcctt ggtagcacta tttagaaga tgagtttaca
10861 ccattgatg tgttagaca atgctgggt gttaccttcc aaggtaagtt caagaaaatt
10921 gttaagggca ctcatcatg gatgcttta acttcttga catcactatt gattcttgtt
10981 caaagtacac agtggtcact gtttttcttt gttacgaga atgcttctt gccatttact
11041 cttggtatta tggcaatgc tgcatgtgct atgctgctg ttaagcataa gcacgcattc
11101 ttgtcttgt ttctgttacc ttctcttgca acagttgctt acttaatat ggtctacatg
11161 cctgctagct gggtgatgcg tatcatgaca tggctgaat tggctgacac tagcttgtct
11221 ggtatatggc ttaaggattg tgttatgtat gctccagctt tagttttgct tattctcatg
11281 acagctcgca ctgtttatga tgatgctgct agacgtgttt ggacactgat gaatgtcatt
11341 acactgtttt acaaagtcta ctatggtaat gctttagatc aagctatttc catgtgggcc
11401 ttagtattt ctgtaacctc taactatct ggtgtcgtta cgactatcat gttttagct
11461 agactataag tgtttgtgtg tgttgagtat tacccatgt tattattac tgccaacacc
11521 ttacagtgta tcatgcttgt ttattgttc ttaggctatt gttgctgctg ctacttggc
11581 cttctgtt tactcaacg ttactcagg cttactcttg gtgttatga ctacttggtc
11641 tctacacaag aatttaggta tatgaactcc caggggcttt gcctcctaa gagtagtatt
11701 gatgcttca agcttaacat taagtgttg ggtattggag gtaaaccatg tatcaaggtt
11761 gctactgtac agtctaaaat gtctgacgta aagtgcacat ctgggtact gctctcggtt
11821 cttcaacaac ttagagtaga gtcatctct aaatgtggg cacaatgtt acaactccac
11881 aatgatattc ttctgcaaa agacacaact gaagcttcg agaagatggt ttctcttttg
11941 tctgttttgc tatccatgca gggtctgta gacattaata ggtgtgcga ggaaatgctc
12001 gataaccgtg ctactcttca ggctattgct tcagaattta gttcttacc atcatatgcc
12061 gcttatgcca ctgccagga ggcctatgag caggctgtag ctaatggtga ttctgaagtc
12121 gttctcaaaa agttaaagaa atcttgaat gtgctaaat ctgagtttga ccgtgatgct
12181 gccatgcaac gcaagttgga aaagatggca gatcaggcta tgacccaaat gtacaaacag
12241 gcaagatctg aggacaagag ggcaaaagta actagtgcta tgcaaacaat gctcttcact
12301 atgcttagga gctgataat tgatgcactt aacaacatta tcaacaatgc gcgtgatggt
12361 tgtgttccac tcaacatct accattgact acagcagcca actcatggt tgtttgcctt
12421 gattatggta cctacaagaa cacttgtgat ggtaacacct tacatatgc atctgcactc
12481 tgggaaatcc agcaagttgt tgatgcggat agcaagattg ttcaactag tgaaattaac
12541 atggacaatt ccccaaatt ggctggcct ctattgtta cagctcaag agccaactca
12601 gctgttaaac tacagaataa tgaactgagt ccagtagcac tacgacagat gtcctgtgcg
12661 gctggtacca cacaaacagc ttgtactgat gacaatgcac ttgcctacta taacaattcg
12721 aagggaggta ggttgtgct ggcattacta tcagccacc aagatctcaa atgggctaga
12781 ttccctaaga gtgatggtac aggtacaatt tacacagaaac tggaaccacc ttgtaggttt
12841 gttacagaca caccaaagg gcctaaagtg aaatacttgt acttcatcaa aggcttaaac
```

Fig. 3 (cont.)

```
12901 aacctaaata gaggtatggt gctgggcagt ttagctgcta cagtacgtct tcaggctgga
12961 aatgctacag aagtacctgc caattcaact gtgctttcct tctgtgcttt tgcagtagac
13021 cctgctaaag catataagga ttacctagca agtggaggac aaccaatcac caactgtgtg
13081 aagatgttgt gtacacacac tggtacagga caggcaatta ctgtaacacc agaagctaac
13141 atggaccaag agtccttgg tggtgcttca tgttgtctgt attgtagatg cccacattgac
13201 catccaaatc ctaaaggatt ctgtgacttg aaaggtaagt acgtccaaat acctaccact
13261 tgtgctaatg acccagtggg tttacactt agaaacacag tctgtaccgt ctgcggaatg
13321 tggaaaggtt atggctgtag ttgtgaccaa ctccgcgaac cctgatgca gtctgcggat
13381 gcatcaacgt tttaaacgg gtttgcgtg taagtgcagc ccgtcttaca ccgtcggca
13441 caggcactag tactgatgtc gtctacaggg cttttgatat ttacaacgaa aaagttgctg
13501 gttttgcaaaa gttcctaaaa actaatgct gtcgcttcca ggagaaggat gaggaaggca
13561 attattaga ctcttacttt gtagttaaga ggcatactat gtctaactac caacatgaag
13621 agactattta taactggtt aaagattgtc cagcggttgc tgtccatgac ttttcaagt
13681 ttagagtaga tggtgacatg gtaccacata tatcacgtca gcgtctaact aaatacacaa
13741 tggctgattt agtctatgct ctacgtcatt tgatgaggg taattgtgat acattaaaag
13801 aaatactcgt cacatacaat tgctgtgatg atgattattt caataagaag gatggtatg
13861 actcgtaga gaatcctgac atctacgcg tatatgctaa cttaggtgag cgtgtacgcc
13921 aatcattatt aaagactgta caattctgcg atgctatgcg tgatgcaggc attgaggcg
13981 tactgacatt agataatcag gatcttaatg ggaactggta cgattcggt gatttcgtac
14041 aagtagcacc aggctgcgga gttcctatg tggattcata ttactcattg ctgatgccca
14101 tcctcacttt gactagggca ttggctgctg agtccatat ggatgctgat ctcgcaaaac
14161 cacttattaa gtgggattg ctgaaaatg atttacgga agagagactt tgtctcttcg
14221 accgttattt taaatattgg gaccagacat accatcccaa ttgtataaac tgttggatg
14281 ataggtgtat cctcattgt gcaaacttta atgtgttatt ttctactgtg ttccaccta
14341 caagttttgg accactagta agaaaaatat ttgtagatgg tgttcctttt gttgttcaa
14401 ctggatacca ttttcgtgag ttaggagtcg tacataatca ggatgtaaac ttacatagct
14461 cgcgtctcag tttcaaggaa cttttagtgt atgctgctga tccagctatg catgcagctt
14521 ctggcaattt attgctagat aaacgcacta catgctttc agtagctgca ctaacaaaca
14581 atgtgcttt tcaaactgtc aaacccggta attttaataa agactttat gacttgctg
14641 tgtctaaagg tttcttaag gaaggaagtt ctgtgaact aaaacactc ttctttgctc
14701 aggatggcaa cgctgctatc agtgattatg actattatcg ttataatctg ccaacaatgt
14761 gtgatatcag acaactccta ttcgtagttg aagtgtgtga taatctctt gattgttacg
14821 atggtggctg tattaatgcc aaccaagtaa tcgttaacaa tctggataaa tcagctggtt
14881 tcccattaa taaatgggt aaggctagac ttattatga ctcaatgaG tatgaggatc
14941 aagatgcact ttcgcgtat actaagcgta atgtcatccc tactataact caaatgaatc
15001 ttaagtatgc cattagtgca aagaatagag ctcgcaccgt agctggtgtc tctatctgta
15061 gtactatgac aaatagacag tttcatcaga aattattgaa gtcaatagcc gccactagag
15121 gagctactgt ggtaattgga acaagcaagt ttacggttg ctggcataat atgtaaaaaa
15181 ctgtttacag tgatgtagaa actccacacc ttatgggttg ggattatcca aaatgtgaca
15241 gagccatgcc taacatgctt aggataatgg cctctctgt tcttgctcgc aaacataaca
15301 ctgctgtaa ctatcacac cgtttctaca ggttagctaa cgagtgtgcg caagtattaa
15361 gtgagatggt catgtgtggc ggctcactat atgttaaacc aggtggaaca tcatccggtg
15421 atgctacaac tgcttatgct aatagtgtct ttaacattg tcaagctgtt acagccaatg
15481 taaatgcact tctttcaact gatggtaata gatagctga caagtatgtc cgcaatctac
15541 aacacaggct ctatgagtgt ctctatagaa atagggatgt tgatcatgaa ttcgtggatg
15601 agtttttacgc ttacctgcgt aaacatttct ccatgatgat tcttctgat gatgccgttg
15661 tgtgctataa cagtaactat gcggctcaag gttagtagc tagcattaag aacttaagg
15721 cagttcttta ttatcaaaat aatgtgttca tgtctgaggc aaaatgttgg actgagactg
15781 accttactaa aggacctcac gaatttgct cacagcatac aatgctagtt aaacaaggag
15841 atgattacgt gtacctgcct taccccagatc catcaagaat attaggcgca ggctgttttg
15901 tcgatgatat tgtcaaaaca gatggtacac ttatgattga aaggttcgtt tcactggcta
15961 ttgatgctta cccactaca aaacatcca atcaggagta tgctgatgtc tttcacttgt
16021 attacaata cattagaaag ttacatgatg agcttactgg cccacatgtt gacatgtatt
16081 ccgtaatgct aactaatgat aacacctcac ggtactggga acctgagttt tatgaggcta
16141 tgtacacacc acatacagtc ttgcaggctg taggtgctg tgtattgtgc aattcacaga
16201 cttcactcg ttgcggtgcc tgtattagga gaccattcct atgtgcaag tgctgtatg
```

Fig. 3 (cont.)

```
16261 accatgtcat ttcaacatca cacaaattag tgttgtctgt taatccctat gtttgcaatg
16321 cccaggtg tgatgtcact gatgtgacac aactgtatct aggaggtatg agctattatt
16381 gcaagtcaca taagcctccc attagttttc cattatgtgc taatggtcag gttttggtt
16441 tatacaaaaa cacatgtgta ggcagtgaca atgtcactga cttcaatgcg atagcaacat
16501 gtgattggac taatgctggc gattacctac ttgccaacac ttgtactgag agactcaagc
16561 ttttcgcagc agaaacgtc aaagccactg aggaaacatt taagctgtca tatggtattg
16621 ccactgtacg cgaagtactc tctgacagag aattgcatct ttcatgggag gttggaaaac
16681 ctagaccacc attgaacaga aactatgtct ttactggtta ccgtgtaact aaaaatagta
16741 aagtacagat tggagagtac accttgaaa aaggtgacta tgtgatgct gttgtgtaca
16801 gaggtactac gacatacaag ttgaatgttg gtgattactt tgtgttgaca tctcacactg
16861 taatgccact tagtgcaccct actctagtgc cacaagagca ctatgtgaga attactggct
16921 tgtacccaac actcaacatc tcagatgagt ttctagcaa tgttgcaaat tatcaaaagg
16981 tcggcatgca aaagtactct acactccaag gaccacctgg tactggtaag agtcattttg
17041 ccatcggact tgctctctat tacccatctg ctcgcatagt gtatacggca tgctctcatg
17101 cagctgttga tgccctatgt gaaaaggcat taaatattt gccccatagat aaatgtagta
17161 gaatcatacc tgcgcgtgcg ccgtagagt gttttgataa attcaaagtg aattcaacac
17221 tagaacagta tgttttctgc actgtaaatg cattgccaga aacaactgct gacattgtag
17281 tcttgatga aatctctatg gctactaatt atgacttgag tgtgtcaat gctagactt
17341 gtgcaaaaca ctacgtctat attggcgatc ctgctcaatt accagccccc cgcacattgc
17401 tgactaaagg cacactagaa ccagaatatt taattcagt gtgcagactt atgaaaacaa
17461 taggtccaga catgttcctt ggaactgtc gccgttgtcc tgctgaaatt gttgacactg
17521 tgagtgcttt agtttatgac aataagctaa aagcacacaa ggataagtca gctcaatgct
17581 tcaaaatgtt ctacaaaggt gttattacac atgatgttc actgcaaatc aacagacctc
17641 aaataggcgt tgtaagagaa ttcttacac gcaatcctgc ttggagaaaa gctgttttta
17701 tctcaccta taatcacag aacgctgtag cttcaaaaat cttaggattg cctacgcaga
17761 ctgttgattc atcacagggt tctgaaatatg actatgtcat attcacacaa actactgaaa
17821 cagcacactc tgtaatgtc aaccgcttca atgtggctat cacaagggca aaaattggca
17881 tttgtcat aatgtctgat agagatcttt atgacaaact gcaattaca agtctagaaa
17941 taccacgtcg caatgtggct acattacaag cagaaaatgt aactggactt tttaaggact
18001 gtagtaagat cattactggt cttcatccta cacaggcacc tacacacctc agcgttgata
18061 taaagttcaa gactgaagga ttatgtgttg acatccagg catccaaaag gacatgacct
18121 accgtagact catctctatg atgggttcca aaatgaatta ccaagtcaat ggttaccctg
18181 atatgttat cacccgcgaa gaagctattc gtcacgttcg tgctgatt ggcttgatg
18241 tagagggctg tcatgcaact agagatgctg tgggtactaa cctacctctc cagctaggat
18301 tttctacagg tgttaactta gtgctgtac cgactggtta tgttgacact gaaaataaca
18361 cagaattcac cagagtaat gcaaaacctc caccaggtga ccagtttaaa catcttatac
18421 cactcatgta taaaggctg cccggaatg tagtgcgtat taagatagta caaatgctca
18481 gtgatacact gaaaggcttg tcagacagag tcgtttcgt ctttgggcg catggcttg
18541 agcttacatc aatgaagtac ttgtcaaga tggacctga agaacgtgt tgtctgtg
18601 acaaacgtgc aacttgcttt tcta ttcat cagatacta tgcctgctgg aatcattctg
18661 tgggttttga ctatgtctat aaccccattta tgattgatgt tcagcagtgg ggcttcacgg
18721 gtaaccttca gagtaaccat gaccaacatt gccaggtaca tggaaatgca catgtggcta
18781 gttgatgc tatcatgact agatgttag cagtccatga gtgcttgtt aagcgcgttg
18841 attggtctgt tgaataccct attataggag atgaactgag ggttaattc gcttgcagaa
18901 aagtacaaca catggttgtg aagtctgcat tgcttgctga taagttcca gttcttcatg
18961 acattggaaa tccaaaggct atcaagtgtg tgcctcaggc tgaagtagaa tggaagttct
19021 acgatgctca gccatgtagt gacaaagctt acaaaataga ggaactcttc tatctctatg
19081 ctacacatca cgataaatcc actgatggtt ttgttgtt ttggaattgt aacgttgatc
19141 gttacccagc caatgcaatt gtgtgtaggt ttgacacaag agtcttgtca aacttgaact
19201 taccaggctg tgatggtggt agtttgtatg tgaataagca tgcattccac actccagctt
19261 tcgataaaag tgcatttact aattaaagc aattgccttt ctttactat tctgatagtc
19321 ctgtgagtc tcatgcaaaa caagtagtgt cggatattga ttatgttcca ctcaaatctg
19381 ctacgtgtat tacacgatgc aattaggtg gtgctgtttg cagacacccat gcaaatgagt
19441 accgacagta cttggatgca tataatatga tgattctgc tggatttagc ctatggattt
19501 acaaacaatt tgatactta aacctgtgga atcatttac caggttacag agtttagaaa
19561 atgtggctta taatgttgtt aataaaggac actttgatgg acacgccggc gaagccctg
```

Fig. 3 (cont.)

```
19621 ttccatcat taataatgct gttacacaa aggtagatgg tattgatgtg gagatcttg
19681 aaaataagac aacacttcct gttaatgttg cattgagct tgggctaag cgtaacatta
19741 aaccagtgcc agagattaag atactcaata atttgggtgt tgatatcgct gctaatactg
19801 taatctggga ctacaaaaga gaagcccag cacatgtatc tacaataggt gtctgcacaa
19861 tgactgacat tgccaagaaa cctactgaga gtgctgttc tcacttact gtctgtttg
19921 atggtagagt ggaaggacag gtagacctt ttagaaacgc ccytaatggg gtttaataa
19981 cagaaggtc agtcaaaggt ctaacaccft caaagggacc agcacaagct agcgtcaatg
20041 gagtcacatt aattgagaa tcagtaaaaa cacagtttaa ctactttaag aaagtagacg
20101 gcattattca acagttgcct gaaacctact ttactcagag cagagactta gaggatttta
20161 agcccagatc acaaatggaa actgactttc tcgagctcgc tatggatgaa tcatacagt
20221 gatataagct cgagggctat gccttcgaac acatcgtta tggagattc agtcatggac
20281 aactggcgg tcttcattta atgataggct tagccaagcg ctcacaagat tcaccactta
20341 aattagagga tttatcct atggacagca cagtgaaaaa ttacttcata acagatgcgc
20401 aaacaggttc atcaaaatgt gtgttctg tgattgatct tttactgat gacttgtcg
20461 agataataaa gtcacaagat ttgtcagtga ttcaaaagt ggtcaaggtt acaattgact
20521 atgctgaaat tcattcatg cttggtgta aggatggaca tgttgaaacc ttctacccaa
20581 aactacaagc aagtcgagcg tggcaaccaa gtgttgcgat gcctaacttg tacaagatgc
20641 aaagaatgct tcttgaaaag tgtgaccttc agaattatgg tgaaaatgct gttataccaa
20701 aaggaataat gatgaatgtc gcaaagtata ctcaactgtg tcaatactta aatacacta
20761 ctttagctgt acctacaac atgagagta ttcactttgg tgctggctct gataaaggag
20821 tgcaccagg tacagctgtg ctcagacaat ggtgccaac tggcacacta cttgtcgatt
20881 cagatcttaa tgacttcgtc tccgacgcat attctactt aattggagac tgtgcaacag
20941 tacatacggc taataaatgg gaccttatta ttagcgatat gtatgaccct aggaccaaac
21001 atgtgacaaa agagaatgac tctaaagaag ggttttcac ttatctgtgt ggatttataa
21061 agcaaaaact agccctgggt ggttctatag ctgtaaagat aacagagcat tcttggaatg
21121 ctgaccttta caagcttatg ggccattct catggtggac agcttttgtt acaaatgtaa
21181 atgcatcatc atcggaagca tttttaattg gggctaacta tctggcaag ccgaaggaac
21241 aaatgatgg ctataccatg catgctaact acatttctg gaggaacaca aatcctatcc
21301 agttgtcttc ctattcactc ttgacatga gcaaattcc tcttaaatta agaggaactg
21361 cgtaatgtc tcttaaggag aatcaaatca atgatatgat ttattctctt ctggaaaaag
21421 gtaggcttat cattagagaa aacaacagag ttgtggttc aagtgatatt cttgttaaca
21481 actaaacgaa catgttatt ttcttattat tcttactct cactagtggt agtgaacttg
21541 accggtcac cacttttgat gatgttcaag ctcctaatta cactcaaacat acttcatcta
21601 tgaggggggt ttactatcct gatgcaattt tagatcaga cactctttat ttaactcagg
21661 atttatttct tccattttat tctaatgtta cagggttca tactattaat catacgttg
21721 gcaaccctgt catacctttt aaggatggta tttattttgc tgccacagag aaatcaaatg
21781 ttgtccgtgg ttggtttttt ggttctacca tgaacaacaa gtcacagtcg gtgattatta
21841 ttaacaattc tactaatgtt gttatacgag catgtaactt tgaattgtgt gacaaccctt
21901 tctttgctgt tctaaaaccc atgggtacac agacacatac tatgatattc gataatgcat
21961 ttaatgcac ttcgagtac atatctgatg cctttcgct tgatgttca gaaaagtcag
22021 gtaattttaa acacttacga gagtttgtgt taaaaataa agatgggtt ctctatgttt
22081 ataagggcta tcaacctata gatgtagttc gtgatctacc ttctgttttt aacactttga
22141 aacctatttt aaagttgcct cttggtatta acattacaaa tttagagcc attcttacag
22201 cctttcacc tgctcaagac atttgggca cgtcagctgc agcctatttt gttggctatt
22261 taaagccaac tacattatg ctcaagtatg atgaaaatgg tacaatcaca gatgctgttg
22321 attgttctca aaatccactt gctgaactca aatgtctgt taagagcttt gagattgaca
22381 aaggaattta ccagacctct aattcaggg ttgtcccte aggagatgtt gtgagattcc
22441 ctaatattac aaactgtgt cctttggag aggttttaa tgctactaaa ttccctctg
22501 tctatgcatg ggagagaaaa aaaatttcta attgtgttgc tgattactct gtgctctaca
22561 actcaacatt ttttcaaco ttaagtgct atggcgttc tgccactaag ttgaatgatc
22621 ttgcttctc caatgtctat gcagattctt tgtagtcaa gggagatgat gtaagacaaa
22681 tagcgccagg acaaacggt gttattgctg attataatta taaattgcca gatgattca
22741 tgggtgtgt cctgctggg aatactagga acattgatgc tactcaacct ggtaattata
22801 attataaata taggtatctt agacatggca agctaggcc cttgagaga gacatatcta
22861 atgtcctt ctccctgat ggcaaaacct gcaccccacc tgctcttaat tgttattggc
22921 cattaaatga ttatggtttt tacaccacta ctggcattgg ctaccaacct tacagagttg
```

Fig. 3 (cont.)

```
22981 tagtactttc tttgaactt taaaatgcac cggccacggt tgtggacca aaattatcca
23041 ctgacctat taagaaccag tgtgtcaatt ttaattaa tggactcact ggtactggtg
23101 tgttaactcc ttcttcaaag agatttcaac cattcaaca atttggccgt gatgtttctg
23161 attcactga ttccgttcga gatcctaaaa catctgaaat attagacatt tcaccttgcg
23221 cttttggggg tgtaagtgta attacacctg gaacaaatgc ttcatctgaa gttgctgttc
23281 tatatcaaga tgttaactgc actgatgttt ctacagcaat tcatgcagat caactcacac
23341 cagcttggcg catatatctct actggaaaca atgtattcca gactcaagca ggctgtctta
23401 taggagctga gcatgtcgac acttcttatg agtgcgacat tcctattgga gatggcattt
23461 gtgctagtta ccatacagtt tctttattac gtagtactag ccaaaaatct attgtggctt
23521 atactatgtc ttaggtgct gatagttcaa ttgcttactc taataacacc attgctatac
23581 ctactaactt ttcaattagc attactacag aagtaatgcc tgttctatg gctaaaaact
23641 ccgtagattg taatatgtac atctgcggag attctactga atgtgctaat ttgcttctcc
23701 aaatatggtag cttttgcaaca caactaaatc gtgcactctc aggtatgct gctgaacagg
23761 atcgcaacac acgtgaagtg ttcgctcaag tcaaacaaat gtacaaaacc ccaacttga
23821 aatattttgg tggttttaat tttcacaaa tattacctga ccctctaaag ccaactaaga
23881 ggtcttttat tgaggactg ctcttaaata aggtgacact cgctgatgct ggcttcatga
23941 agcaatatgg cgaatgccta ggtgatatta atgctagaga tctcatttgt gcgcagaagt
24001 tcaatggact tacagtgttg ccacctctgc tcactgatga tatgattgct gcctacactg
24061 ctgctctagt tagtgtact gccactgctg gatggacatt tggtgctggc gctgctctttc
24121 aaatacctttt tgctatgcaa atggcatata ggttcaatgg cattggagtt acccaaaatg
24181 ttctctatga gaaccaaaaa caaatcgcca accaatttaa caaggcgatt agtcaaattc
24241 aagaatcact tacaacaaca tcaactgcat tgggcaagct gcaagacgtt gttaaccaga
24301 atgctcaagc attaaacaca cttgttaaac aacttagctc taattttggt gcaatttcaa
24361 gtgtgctaaa tgatatcctt tcgcgacttg ataaagtcga ggcggaggta caaattgaca
24421 ggttaattac aggcagactt caaagccttc aaacctatgt aacacaacaa ctaatcaggg
24481 ctgctgaaat caggggttct gctaaatctg ctgctactaa aatgtctgag tgtgttctg
24541 gacaatcaaa aagagttgac tttgtggaa agggctacca ccttatgtcc ttcccacaag
24601 cagccccgca tggtgttgtc ttcctacatg tcacgtatgt gccatcccga gagaggaact
24661 tcaccacagc gccagcaatt tgtcatgaag gcaaagcata cttccctcgt gaaggtgttt
24721 ttgtgttaa tggcacttct tggttttta cacagaggaa ctttcttct ccacaaataa
24781 ttactacaga caatacattt gtctcaggaa attgtgatgt cgtattggc atcattaaca
24841 acacagtttta tgatcctctg caacctgagc ttgactcatt caagaagag ctggacaagt
24901 acttcaaaaa tcatacatca ccagatgttg atcttggcga cattcaggc attaacgctt
24961 ctgtcgtcaa cattcaaaaa gaaattgacc gcctcaatga ggtgctaaa aatttaaatg
25021 aatcactcat tgaccttcaa gaatgggaa aatatgagca atatattaaa tggccttggt
25081 atgttggct cggcttcatt gctggactaa ttgccatcgt catggttaca atcttgcttt
25141 gtgcatgac tagttgtgc agttgcctca agggtgcatg ctcttgtggt tcttgctgca
25201 agtttgatga ggatgactct gagccagttc tcaagggtgt caaattacat tacacataaa
25261 cgaacttatg gatttgttta tgagatttt tactcttgga tcaattactg cacagccagt
25321 aaaaattgac aatgcttctc ctgcaagtac tgttcatgct acagcaacga taccgctaca
25381 agcctcactc cctttcggat ggcttgtat tggcgttgca tttctgctg ttttcagag
25441 cgctaccaaa ataattgcgc tcaataaag atggcagcta gcccttata agggcttcca
25501 gttcatttgc aatttactgc tgctattgt taccatctat tcacatctt tgcttgtcgc
25561 tgcaggtact gaggcgcaat tttgtacct ctatgccttg atatatttc tacaatgcat
25621 caacgcatgt agaattatta tgagatgttg gcttgtgg aagtgcaaat ccaagaaccc
25681 attacttat gatgccaact acttgtttg ctggcacaca cataactatg actactgtat
25741 accatataac agtgtcacg atacaattgt cgttactgaa ggtgacggca tttcaacacc
25801 aaaactcaaa gaagacacc ttattggtgg ttctcgag gataggcact caggtttaa
25861 agactatgtc gtgtacatg gctatttcac cgaagtttac taccagcttg agtctacaca
25921 aaftactaca gacactggta ttgaaaatgc tacattcttc atcttaaca agcttgttaa
25981 agaccacacg aatgtgcaaa tacacacaat cgacggctct tcaggagttg ctaatccagc
26041 aatggatcca atttatgatg agccgacgac gactactagc gtgcctttgt aagcacaaga
26101 aagtgagtac gaacttatgt actcattcgt ttcggaagaa acaggtacgt taatagttaa
26161 tagcgtactt cttttcttg ctttcgtggt attcttgcta gtcacactag coatccttac
26221 tgcgcttcga ttgtgtgcgt actgctgcaa tattgttaac gtgagtttag taaaaccaac
26281 ggtttacgtc tactcgcgtg ttaaaaatct gaactcttct gaaggagttc ctgatcttct
```

Fig. 3 (cont.)

```
26341 ggtctaaacg aactaactat tattattatt ctgttggaa cttaacatt gctatcatg
26401 gcagacaacg gtactattac cgttgaggag cttaaacaac tcctggaaca atggaaccta
26461 gtactaggtt tcctattcct agcctggatt atgttactac aattgccta ttctaatcgg
26521 aacaggtttt tgtacataat aaagctgtt ttcctctggc tcttgtggcc agtaacactt
26581 gctgttttg tgcttgctgc tgtctacaga attaattggg tgactggcgg gattgcgatt
26641 gcaatggctt gtattgtagg cttgatgtgc cttagctact tcgttgcttc cttcaggctg
26701 ttgctcgta cccgtcaaat gtggtcattc aacccagaaa caaacattct tctcaatgtg
26761 cctcgcggg ggacaattgt gaccagaccg ctcatggaaa gtgaactgtg cattggtgct
26821 gtgatcattc gtggtcactt gcgaatggcc ggacactccc tagggcgctg tgacattaag
26881 gaactgccaa aagagatcac tgtggctaca tcacgaacgc tttcttatta caaattagga
26941 gcgtgcagc gtgtaggcac tgattcaggt ttgctgcat acaaccgcta ccgtattgga
27001 aactataaat taaatacaga ccacgccggt agcaacgaca atattgcttt gctagtacag
27061 taagtgacaa cagatgtttc atcttgtga cttccaggt acaatagcag agatattgat
27121 tatcattatg aggactttca ggattgctat ttggaatctt gacgttataa taagttcaat
27181 agtgagacaa ttatttaagc ctctaactaa gaagaattat tcggagttag atgatgaaga
27241 acctatggag ttagattatc catasaacga acatgaaaat tattctcttc ctgacattga
27301 ttgtatttac atcttgcgag ctatatcact atcaggagtg tgttacaggt acgactgtac
27361 tactaaaaga accttgccca tcaggaaacat acgagggcaa ttcaccattt caccctcttg
27421 ctgacaataa atttgcacta actgcacta gcacacactt tgctttgct tgtgctgacg
27481 gtactcgaca tacctatcag ctgcgtgcaa gatcagttc accaaaactt ttcatcagac
27541 aagaggaggt tcaacaagag ctctactcgc cacttttct cattgttgct gctctagtat
27601 ttttaatact ttgcttcacc attaagagaa agacagaatg aatgagctca cttaattga
27661 ctttcatattg tgcttttag ccttctgct attcctgtt ttaataatgc ttattatatt
27721 ttggtttca ctcgaaatcc aggatctaga agaacctgt accaaagtct aaacgaacat
27781 gaaacttctc attgttttga ctgtattc tctatgcagt tgcatatgca ctgtagtaca
27841 gcgcgtgca tctaataaac ctcatgtgct tgaagatcct tgtaaggtac aacactaggg
27901 gtaatactta tagcactgct tggcttgtg ctctaggaaa ggttttaccct ttcatagat
27961 ggcacactat ggttcaaaca tgcacaccta atgttactat caactgtcaa gatccagctg
28021 gtggtgcgct tatagctagg tgttggtacc ttcatgaagg tcaccaaact gctgcattta
28081 gagacgtact tgttgtttta aataaacgaa caaattaaaa tgtctgataa tggaccccaa
28141 tcaaaccaac gtagtgcccc ccgcattaca tttggtggac ccacagattc aactgacaat
28201 aaccagaatg gaggacgcaa tgggcaagg ccaaaacago gccgacccca aggtttaccc
28261 aataatactg cgtctggtt cacagctctc actcagcatg gcaaggagga acttagattc
28321 cctcgaggcc agggcgttcc aatcaacacc aatagtggtc cagatgacca aattggctac
28381 taccgaagag ctaccogacg agtcgtggt ggtgacggca aaatgaaaga gctcagcccc
28441 agatggtact tctattacct aggaactggc ccagaagctt cacttcccta cggcgctaac
28501 aaagaaggca tcgtatgggt tgcaactgag ggagccttga atacacccaa agaccacatt
28561 ggcacccgca atcctaataa caatgctgcc accgtgctac aacttcctca aggaacaaca
28621 ttgccaaaag gcttctacgc agagggaagc agaggcggca gtcaagcctc ttctcgctcc
28681 tcatcacgta gtcgcggtaa ttcaagaaat tcaactctg gcagcagtag gggaaattct
28741 cctgctcgaa tggctagcgg aggtggtgaa actgccctcg cgctattgct gctagacaga
28801 ttgaaccagc ttgagagcaa agtttctggt aaaggccaac aacaacaagg ccaaactgtc
28861 actaagaaat ctgctgctga ggcatctaaa aagcctcgcc aaaaacgtac tgccacaaaa
28921 cagtacaacg tcactcaagc atttgggaga cgtggtccag aacaaaccca aggaaatttc
28981 ggggaccaag acctaatcag acaaggaact gattacaaac attggccgca aattgcacaa
29041 ttgctccaa gtgcctctgc attcttgga atgtcacgca ttggcatgga agtcacacct
29101 tcgggaacat ggctgactta tcatggagcc attaaattgg atgacaaaga tccacaattc
29161 aaagacaacg tcatactgct gaacaagcac attgacgcat acaaaacatt cccaccaaca
29221 gagcctaaaa aggacaaaaa gaaaaagact gatgaagctc agcctttgcc gcagagacaa
29281 aagaagcagc ccactgtgac tcttcctct gcggctgaca tggatgatt ctccagacaa
29341 cttcaaaatt ccatgagtgg agcttctgct gattcaactc aggcataaac actcatgatg
29401 accacacaag gcagatgggc tatgtaaacg ttttcgcaat tccgtttacg atacatagtc
29461 tactcttgtg cagaatgaat tctcgtaact aaacagcaca agtaggttta gttaacttta
29521 atctcacata gcaatcttta atcaatgtgt aacattaggg aggacttgaa agagccacca
29581 cattttcatc gaggccacgc ggagtacgat cgagggtaca gtgaataatg ctagggagag
29641 ctgcctatat ggaagagccc taatgtgtaa aattaattt agtagtgcta tccccatgtg
```

Fig. 3 (cont.)

29701 attttcatag ctcttagga gaatgacaaa aaaaaaaaa aaaaaaaaa a
//

Fig. 3 (cont.)

Fig. 5. The Subgenomic HCV Replicon Used to Test
The Efficacy of siRNA in Human Liver Cells
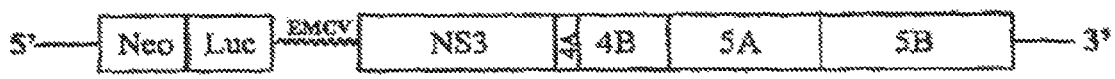
Neo: neomycin phosphotransferase gene
Luc: fruit fly luciferase
EMCV: internal ribosome entry site taken from EMCV
NS3, NS4A, NS4B, NS5A, and NS5B: HCV nonstructural proteins

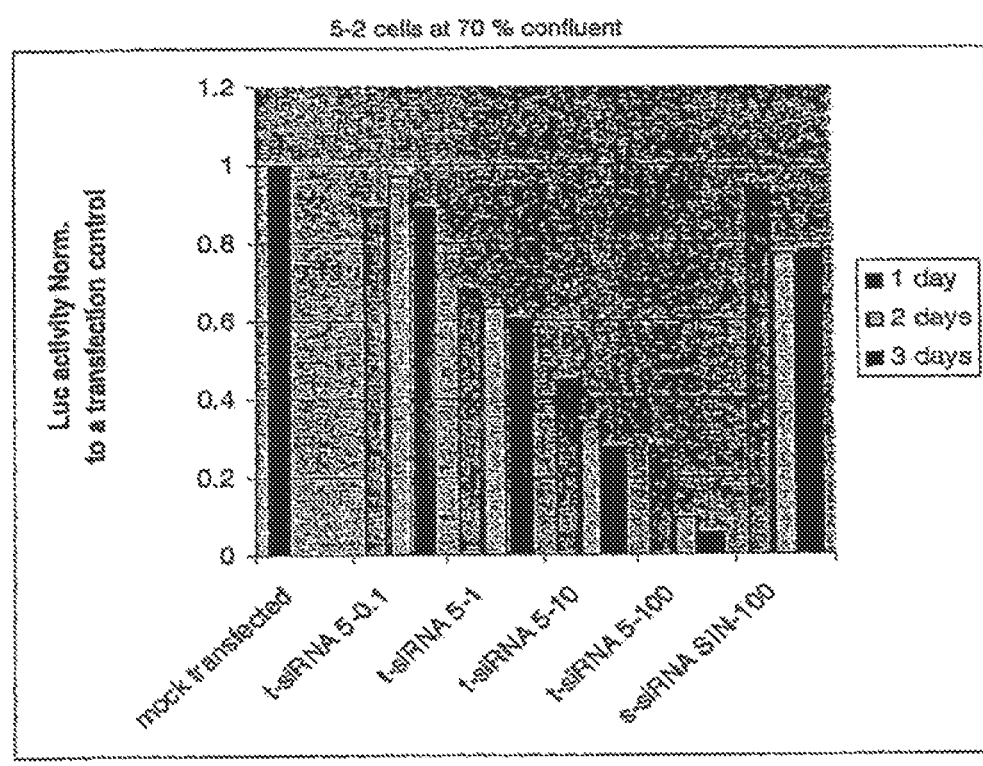
Fig. 6. The Effect of siRNAs on HCV Replication In Huh 5-2 Cells

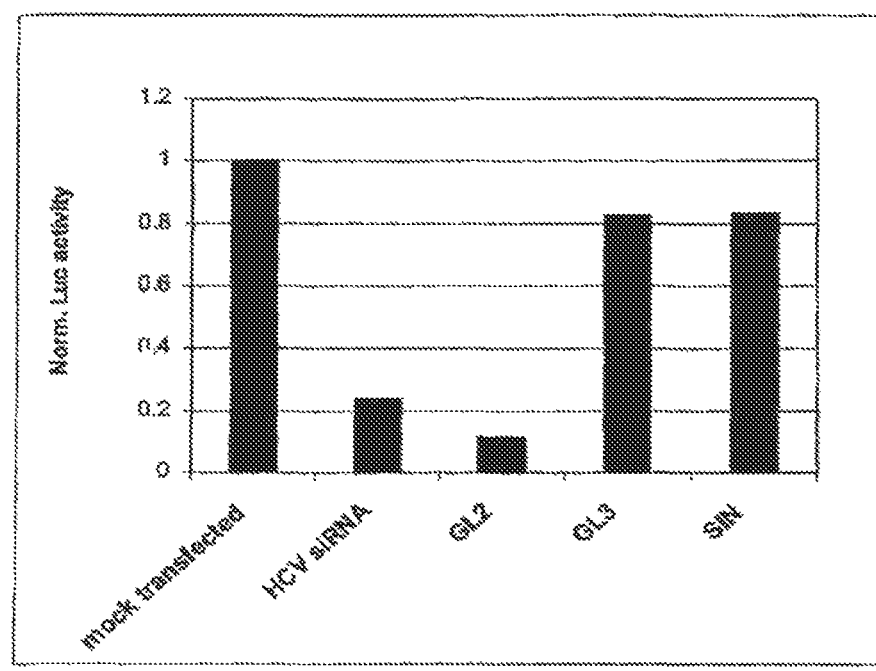

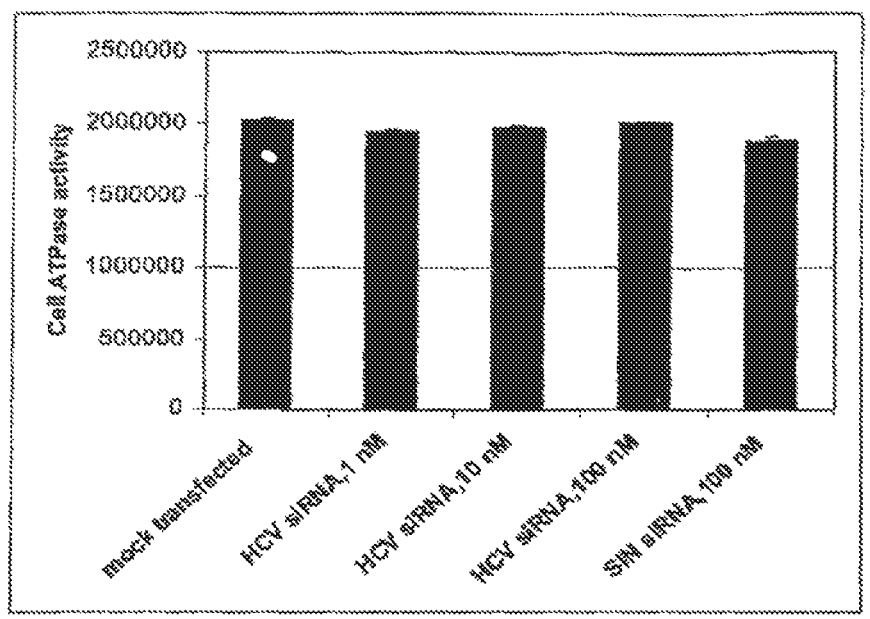
Fig. 8. The Effect of siRNA5 of Cell Viability Measured by Cellular ATPase Activity
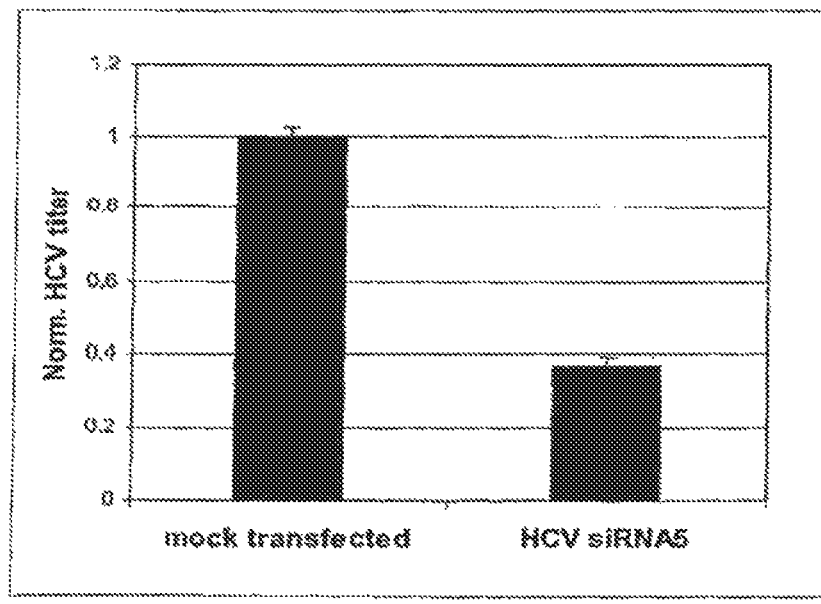
Fig. 9. The Effect of siRNA5 on HCV Replication in Huh-7 Cells Measured by HCV RNA Assay

SEQUENCE LISTING

<160> NUMBER OF SEQ ID NOS: 68

<210> SEQ ID NO 1
<211> LENGTH: 29751
<212> TYPE: DNA
<213> ORGANISM: SARS coronavirus

<400> SEQUENCE: 1

```
ttattaggtt tttacctacc caggaaaagc caaccaacct cgatctcttg tagatctgtt      60
ctctaaacga actttaaaat ctgtgtagct gtcgctcggc tgcatgccta gtgcacctac     120
gcagtataaa caataataaa ttttactgtc gttgacaaga aacgagtaac tcgtccctct     180
tctgcagact gcttacggtt tcgtccgtgt tgcagtcgat catcagcata cctaggtttc     240
gtccgggtgt gaccgaaagg taagatggag agccttgttc ttggtgtcaa cgagaaaaca     300
cacgtccaac tcagtttgcc tgtccttcag gttagagacg tgctagtgcg tggcttcggg     360
gactctgtgg aagaggccct atcggaggca cgtgaacacc tcaaaaatgg cacttgtggt     420
ctagtagagc tggaaaaagg cgtactgccc cagcttgaac agccctatgt gttcattaaa     480
cgttctgatg ccttaagcac caatcacggc cacaaggtcg ttgagctggt tgcagaaatg     540
gacggcattc agtacggtcg tagcggtata acactgggag tactcgtgcc acatgtgggc     600
gaaaccccaa ttgcataccg caatgttctt cttcgtaaga acggtaataa gggagccggt     660
ggtcatagct atggcatcga tctaaagtct tatgacttag gtgacgagct tggcactgat     720
cccattgaag attatgaaca aaactggaac actaagcatg gcagtggtgc actccgtgaa     780
ctcactcgtg agctcaatgg aggtgcagtc actcgctatg tcgacaacaa tttctgtggc     840
ccagatgggt accctcttga ttgcatcaaa gattttctcg cacgcgcggg caagtcaatg     900
tgcactcttt ccgaacaact tgattacatc gagtcgaaga gaggtgtcta ctgctgccgt     960
gaccatgagc atgaaattgc ctggttcact gagcgctctg ataagagcta cgagcaccag    1020
acacccttcg aaattaagag tgccaagaaa tttgacactt tcaaagggga atgcccaaag    1080
tttgtgtttc ctcttaactc aaaagtcaaa gtcattcaac cacgtgttga aaagaaaaag    1140
actgagggtt tcatggggcg tatacgctct gtgtaccctg ttgcatctcc acaggagtgt    1200
aacaatatgc acttgtctac cttgatgaaa tgtaatcatt gcgatgaagt tcatggcag    1260
acgtgcgact ttctgaaagc cacttgtgaa cattgtggca ctgaaaattt agttattgaa    1320
ggacctacta catgtgggta cctacctact aatgctgtag tgaaaatgcc atgtcctgcc    1380
tgtcaagacc cagagattgg acctgagcat agtgttgcag attatcacaa ccactcaaac    1440
attgaaactc gactccgcaa gggaggtagg actagatgtt ttggaggctg tgtgtttgcc    1500
tatgttggct gctataataa gcgtgcctac tgggttcctc gtgctagtgc tgatattggc    1560
tcaggccata ctggcattac tggtgacaat gtggagacct tgaatgagga tctccttgag    1620
atactgagtc gtgaacgtgt taacattaac attgttggcg attttcattt gaatgaagag    1680
gttgccatca ttttggcatc tttctctgct tctacaagtg cctttattga cactataaag    1740
```

```
agtcttgatt acaagtcttt caaaaccatt gttgagtcct gcggtaacta taaagttacc    1800
aagggaaagc ccgtaaaagg tgcttggaac attggacaac agagatcagt tttaacacca    1860
ctgtgtggtt ttccctcaca ggctgctggt gttatcagat caattttgc gcgcacactt     1920 gatgcagcaa accactcaat tcctgatttg caaagagcag ctgtcaccat acttgatggt    1980
atttctgaac agtcattacg tcttgtcgac gccatggttt atacttcaga cctgctcacc    2040
aacagtgtca ttattatggc atatgtaact ggtggtcttg tacaacagac ttctcagtgg    2100
ttgtctaatc ttttgggcac tactgttgaa aaactcaggc ctatctttga atggattgag    2160
gcgaaactta gtgcaggagt tgaatttctc aaggatgctt gggagattct caaatttctc    2220
attacaggtg ttttttgacat cgtcaagggt caaatacagg ttgcttcaga taacatcaag    2280
gattgtgtaa aatgcttcat tgatgttgtt aacaaggcac tcgaaatgtg cattgatcaa    2340
gtcactatcg ctggcgcaaa gttgcgatca ctcaacttag gtgaagtctt catcgctcaa    2400
agcaagggac tttaccgtca gtgtatacgt ggcaaggagc agctgcaact actcatgcct    2460
cttaaggcac caaaagaagt aacctttctt gaaggtgatt cacatgacac agtacttacc    2520
tctgaggagg ttgttctcaa gaacggtgaa ctcgaagcac tcgagacgcc cgttgatagc    2580
ttcacaaatg gagctatcgt cggcacacca gtctgtgtaa atggcctcat gctcttagag    2640
attaaggaca agaacaata ctgcgcattg tctcctggtt tactggctac aaacaatgtc     2700
tttcgcttaa aaggggtgc accaattaaa ggtgtaacct ttggagaaga tactgtttgg    2760
gaagttcaag gttacaagaa tgtgagaatc acatttgagc ttgatgaacg tgttgacaaa    2820
gtgcttaatg aaaagtgctc tgtctacact gttgaatccg gtaccgaagt tactgagttt    2880
gcatgtgttg tagcagaggc tgttgtgaag actttacaac cagtttctga tctccttacc    2940
aacatgggta ttgatcttga tgagtggagt gtagctacat tctacttatt tgatgatgct    3000
ggtgaagaaa acttttcatc acgtatgtat tgttcctttt accctccaga tgaggaagaa    3060
gaggacgatg cagagtgtga ggaagaagaa attgatgaaa cctgtgaaca tgagtacggt    3120
acagaggatg attatcaagg tctccctctg gaatttggtg cctcagctga aacagttcga    3180
gttgaggaag aagaagagga agactggctg gatgatacta ctgagcaatc agagattgag    3240
ccagaaccag aacctacacc tgaagaacca gttaatcagt ttactggtta tttaaaactt    3300
actgacaatg ttgccattaa atgtgttgac atcgttaagg aggcacaaag tgctaatcct    3360
atggtgattg taaatgctgc taacatacac ctgaaacatg gtggtggtgt agcaggtgca    3420
ctcaacaagg caaccaatgg tgccatgcaa aaggagagtg atgattacat taagctaaat    3480
ggccctctta cagtaggagg gtcttgtttg ctttctggac ataatcttgc taagaagtgt    3540
ctgcatgttg ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag gagccaccaa acacagaaga ttccaaaact    3840
gaggagaaat ctgtcgtaca gaagcctgtc gatgtgaagc aaaaattaa ggcctgcatt    3900 gatgaggtta ccacaacact ggaagaaact aagtttctta ccaataagtt actcttgttt    3960
gctgatatca atggtaagct ttaccatgat tctcagaaca tgcttagagg tgaagatatg    4020
tctttccttg agaaggatgc accttacatg gtaggtgatt ttatcactag tggtgatatc    4080
acttgtgttg taataccctc caaaaaggct ggtggcacta ctgagatgct ctcaagagct    4140
```

```
ttgaagaaag tgccagttga tgagtatata accacgtacc ctggacaagg atgtgctggt    4200
tatacacttg aggaagctaa gactgctctt aagaaatgca aatctgcatt ttatgtacta    4260
ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt cttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta agctcctgc cgtagtgtca    4620 gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagcccgt cgagtttcat cttgacggtg aggttctttc acttgacaaa    4860
ctaaagagtc tcttatccct gcgggaggtt aagactataa aagtgttcac aactgtggac    4920
aacactaatc tccacacaca gcttgtggat atgtctatga catatggaca gcagtttggt    4980
ccaacatact tggatggtgc tgatgttaca aaaattaaac ctcatgtaaa tcatgagggt    5040
aagactttct ttgtactacc tagtgatgac acactacgta gtgaagcttt cgagtactac    5100
catactcttg atgagagttt tcttggtagg tacatgtctg ctttaaacca cacaaagaaa    5160
tggaaatttc ctcaagttgg tggtttaact tcaattaaat gggctgataa caattgttat    5220
ttgtctagtg ttttattagc acttcaacag cttgaagtca aattcaatgc accagcactt    5280
caagaggctt attatagagc ccgtgctggt gatgctgcta acttttgtgc actcatactc    5340
gcttacagta ataaaactgt tggcgagctt ggtgatgtca gagaaactat gacccatctt    5400
ctacagcatg ctaatttgga atctgcaaag cgagttctta atgtggtgtg taaacattgt    5460
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttcttttgtt atgatgtctg caccacctgc tgagtataaa    5640
ttacagcaag gtacattctt atgtgcgaat gagtacactg gtaactatca gtgtggtcat    5700
tacactcata taactgctaa ggagaccctc tatcgtattg acggagctca ccttacaaag    5760
atgtcagagt acaaaggacc agtgactgat gttttctaca aggaaacatc ttacactaca    5820
accatcaagc ctgtgtcgta taaactcgat ggagttactt acacagagat tgaaccaaaa    5880
ttggatgggt attataaaaa ggataatgct tactatacag agcagcctat agaccttgta    5940
ccaactcaac cattaccaaa tgcgagtttt gataatttca aactcacatg ttctaacaca    6000
aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
acaaagccag tagatacttc aaattcattt gaagttctgg cagtagaaga cacacaagga    6300
atggacaatc ttgcttgtga agtcaacaa cccacctctg aagaagtagt ggaaaatcct    6360
accatacaga aggaagtcat agagtgtgac gtgaaaacta ccgaagttgt aggcaatgtc    6420
atacttaaac catcagatga aggtgttaaa gtaacacaag agttaggtca tgaggatctt    6480
```

```
atggctgctt atgtggaaaa cacaagcatt accattaaga aacctaatga gctttcacta    6540
gccttaggtt taaaaacaat tgccactcat ggtattgctg caattaatag tgttccttgg    6600
agtaaaattt tggcttatgt caaaccattc ttaggacaag cagcaattac aacatcaaat    6660
tgcgctaaga gattagcaca acgtgtgttt aacaattata tgccttatgt gtttacatta    6720
ttgttccaat tgtgtacttt tactaaaagt accaattcta gaattagagc ttcactacct    6780
acaactattg ctaaaaatag tgttaagagt gttgctaaat tatgtttgga tgccggcatt    6840
aattatgtga agtcacccaa attttctaaa ttgttcacaa tcgctatgtg gctattgttg    6900
ttaagtattt gcttaggttc tctaatctgt gtaactgctg cttttggtgt actcttatct    6960
aattttggtg ctccttctta ttgtaatggc gttagagaat tgtatcttaa ttcgtctaac    7020
gttactacta tggatttctg tgaaggttct tttccttgca gcatttgttt aagtggatta    7080
gactcccttg attcttatcc agctcttgaa accattcagg tgacgatttc atcgtacaag    7140
ctagacttga caattttagg tctggccgct gagtgggttt tggcatatat gttgttcaca    7200
aaattctttt atttattagg tctttcagct ataatgcagg tgttctttgg ctattttgct    7260
agtcatttca tcagcaattc ttggctcatg tggtttatca ttagtattgt acaaatggca    7320
cccgtttctg caatggttag gatgtacatc ttctttgctt ctttctacta catatggaag    7380
agctatgttc atatcatgga tggttgcacc tcttcgactt gcatgatgtg ctataagcgc    7440
aatcgtgcca cacgcgttga gtgtacaact attgttaatg gcatgaagag atctttctat    7500
gtctatgcaa atggaggccg tggcttctgc aagactcaca attggaattg tctcaattgt    7560
gacacatttt gcactggtag tacattcatt agtgatgaag ttgctcgtga tttgtcactc    7620
cagtttaaaa gaccaatcaa ccctactgac cagtcatcgt atattgttga tagtgttgct    7680
gtgaaaaatg gcgcgcttca cctctacttt gacaaggctg gtcaaaagac ctatgagaga    7740
catccgctct cccatttggt caatttagac aatttgagag ctaacaacac taaaggttca    7800
ctgcctatta tgtcatagt ttttgatggc aagtccaaat gcgacgagtc tgcttctaag    7860
tctgcttctg tgtactacag tcagctgatg tgccaaccta ttctgttgct tgaccaagct    7920
cttgtatcag acgttggaga tagtactgaa gtttccgtta agatgtttga tgcttatgtc    7980 gacaccttt cagcaacttt tagtgttcct atggaaaaac ttaaggcact tgttgctaca    8040
gctcacagcg agttagcaaa gggtgtagct ttagatggtg tccttttctac attcgtgtca    8100 gctgcccgac aaggtgttgt tgataccgat gttgacacaa aggatgttat tgaatgtctc    8160
aaactttcac atcactctga cttagaagtg acaggtgaca gttgtaacaa tttcatgctc    8220
acctataata aggttgaaaa catgacgccc agagatcttg gcgcatgtat tgactgtaat    8280
gcaaggcata tcaatgccca gtagcaaaa agtcacaatg tttcactcat ctggaatgta    8340
aaagactaca tgtctttatc tgaacagctg cgtaaacaaa ttcgtagtgc tgccaagaag    8400
aacaacatac ttttagact aacttgtgct acaactagac aggttgtcaa tgtcataact    8460
actaaaatct cactcaaggg tggtaagatt gttagtactt gttttaaact tatgcttaag    8520
gccacattat tgtgcgttct tgctgcattg gtttgttata tcgttatgcc agtacataca    8580
ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta aagagagat tggtttcata gtgcctggct taccgggtac tgtgctgaga    8820
gcaatcaatg gtgacttctt gcattttcta cctcgtgttt ttagtgctgt tggcaacatt    8880
```

```
tgctacacac cttccaaact cattgagtat agtgattttg ctacctctgc ttgcgttctt   8940
gctgctgagt gtacaatttt taaggatgct atgggcaaac ctgtgccata ttgttatgac   9000
actaatttgc tagagggttc tatttcttat agtgagcttc gtccagacac tcgttatgtg   9060
cttatggatg gttccatcat acagtttcct aacacttacc tggagggttc tgttagagta   9120
gtaacaactt ttgatgctga gtactgtaga catggtacat gcgaaaggtc agaagtaggt   9180
atttgcctat ctaccagtgg tagatgggtt cttaataatg agcattacag agctctatca   9240
ggagttttct gtggtgttga tgcgatgaat ctcatagcta acatctttac tcctcttgtg   9300
caacctgtgg gtgctttaga tgtgtctgct tcagtagtgg ctggtggtat tattgccata   9360
ttggtgactt gtgctgccta ctactttatg aaattcagac gtgttttttgg tgagtacaac   9420 catgttgttg ctgctaatgc acttttgttt ttgatgtctt tcactatact ctgtctggta   9480
ccagcttaca gctttctgcc gggagtctac tcagtctttt acttgtactt gacattctat   9540
ttcaccaatg atgtttcatt cttggctcac cttcaatggt ttgccatgtt ttctcctatt   9600
gtgccttttt ggataacagc aatctatgta ttctgtattt ctctgaagca ctgccattgg   9660
ttctttaaca actatcttag gaaaagagtc atgtttaatg gagttacatt tagtaccttc   9720
gaggaggctg ctttgtgtac cttttttgctc aacaaggaaa tgtacctaaa attgcgtagc   9780
gagacactgt tgccacttac acagtataac aggtatcttg ctctatataa caagtacaag   9840
tatttcagtg gagccttaga tactaccagc tatcgtgaag cagcttgctg ccacttagca   9900
aaggctctaa atgactttag caactcaggt gctgatgttc tctaccaacc accacagaca   9960
tcaatcactt ctgctgttct gcagagtggt tttaggaaaa tggcattccc gtcaggcaaa  10020
gttgaagggt gcatggtaca agtaacctgt ggaactacaa ctcttaatgg attgtggttg  10080
gatgacacag tatactgtcc aagacatgtc atttgcacag cagaagacat gcttaatcct  10140
aactatgaag atctgctcat tcgcaaatcc aaccatagct ttcttgttca ggctggcaat  10200
gttcaacttc gtgttattgg ccattctatg caaaattgtc tgcttaggct taaagttgat  10260
acttctaacc ctaagacacc caagtataaa tttgtccgta tccaacctgg tcaaacattt  10320
tcagttctag catgctacaa tggttcacca tctggtgttt atcagtgtgc catgagacct  10380
aatcatacca ttaaaggttc tttccttaat ggatcatgtg gtagtgttgg ttttaacatt  10440
gattatgatt gcgtgtcttt ctgctatatg catcatatgg agcttccaac aggagtacac  10500
gctggtactg acttagaagg taaattctat ggtccatttg ttgacagaca aactgcacag  10560
gctgcaggta cagacacaac cataacatta atgttttggg catggctgta tgctgctgtt  10620
atcaatggtg ataggtggtt tcttaataga ttcaccacta ctttgaatga ctttaacctt  10680
gtggcaatga agtacaacta tgaaccttttg acacaagatc atgttgacat attgggacct  10740
ctttctgctc aaacaggaat tgccgtctta gatatgtgtg ctgctttgaa agagctgctg  10800
cagaatggta tgaatggtcg tactatcctt ggtagcacta ttttagaaga tgagtttaca  10860
ccatttgatg ttgttagaca atgctctggt gttaccttcc aaggtaagtt caagaaaatt  10920
gttaagggca ctcatcattg gatgctttta actttcttga catcactatt gattcttgtt  10980
caaagtacac agtggtcact gttttctctt gtttacgaga atgctttctt gccatttact  11040
cttggtatta tggcaattgc tgcatgtgct atgctgcttg ttaagcataa gcacgcattc  11100
ttgtgcttgt ttctgttacc ttctcttgca acagttgctt actttaatat ggtctacatg  11160
cctgctagct gggtgatgcg tatcatgaca tggcttgaat tggctgacac tagccttgtct  11220
```

```
ggttataggc ttaaggattg tgttatgtat gcttcagctt tagttttgct tattctcatg   11280
acagctcgca ctgtttatga tgatgctgct agacgtgttt ggacactgat gaatgtcatt   11340
acacttgttt acaaagtcta ctatggtaat gctttagatc aagctatttc catgtgggcc   11400
ttagttattt ctgtaacctc taactattct ggtgtcgtta cgactatcat gtttttagct   11460
agagctatag tgtttgtgtg tgttgagtat tacccattgt tatttattac tggcaacacc   11520
ttacagtgta tcatgcttgt ttattgtttc ttaggctatt gttgctgctg ctactttggc   11580
cttttctgtt tactcaaccg ttacttcagg cttactcttg gtgtttatga ctacttggtc   11640
tctacacaag aatttaggta tatgaactcc caggggcttt tgcctcctaa gagtagtatt   11700
gatgctttca agcttaacat taagttgttg ggtattggag gtaaaccatg tatcaaggtt   11760
gctactgtac agtctaaaat gtctgacgta aagtgcacat ctgtggtact gctctcggtt   11820
cttcaacaac ttagagtaga gtcatcttct aaattgtggg cacaatgtgt acaactccac   11880
aatgatattc ttcttgcaaa agacacaact gaagctttcg agaagatggt ttctcttttg   11940
tctgttttgc tatccatgca gggtgctgta gacattaata ggttgtgcga ggaaatgctc   12000
gataaccgtg ctactcttca ggctattgct tcagaattta gttctttacc atcatatgcc   12060
gcttatgcca ctgcccagga ggcctatgag caggctgtag ctaatggtga ttctgaagtc   12120
gttctcaaaa agttaaagaa atcttttaat gtggctaaat ctgagtttga ccgtgatgct   12180
gccatgcaac gcaagttgga aaagatggca gatcaggcta tgacccaaat gtacaaacag   12240
gcaagatctg aggacaagag ggcaaaagta actagtgcta tgcaaacaat gctcttcact   12300
atgcttagga agcttgataa tgatgcactt aacaacatta tcaacaatgc gcgtgatggt   12360
tgtgttccac tcaacatcat accattgact acagcagcca aactcatggt tgttgtccct   12420
gattatggta cctacaagaa cacttgtgat ggtaacacct ttacatatgc atctgcactc   12480
tgggaaatcc agcaagttgt tgatgcggat agcaagattg ttcaacttag tgaaattaac   12540
atggacaatt caccaaattt ggcttggcct cttattgtta cagctctaag agccaactca   12600
gctgttaaac tacagaataa tgaactgagt ccagtagcac tacgacagat gtcctgtgcg   12660
gctggtacca cacaaacagc ttgtactgat gacaatgcac ttgcctacta taacaattcg   12720
aagggaggta ggtttgtgct ggcattacta tcagaccacc aagatctcaa atgggctaga   12780 ttcccctaaga gtgatggtac aggtacaatt tacacagaac tggaaccacc ttgtaggttt   12840
gttacagaca caccaaaagg gcctaaagtg aaatacttgt acttcatcaa aggcttaaac   12900
aacctaaata gaggtatggt gctgggcagt ttagctgcta cagtacgtct tcaggctgga   12960
aatgctacag aagtacctgc caattcaact gtgctttcct tctgtgcttt tgcagtagac   13020
cctgctaaag catataagga ttacctagca agtggaggac aaccaatcac caactgtgtg   13080
aagatgttgt gtacacacac tggtacagga caggcaatta ctgtaacacc agaagctaac   13140
atggaccaag agtcctttgg tggtgcttca tgttgtctgt attgtagatg ccacattgac   13200
catccaaatc ctaaaggatt ctgtgacttg aaaggtaagt acgtccaaat acctaccact   13260
tgtgctaatg acccagtggg ttttacactt agaaacacag tctgtaccgt ctgcggaatg   13320
tggaaaggtt atggctgtag ttgtgaccaa ctccgcgaac ccttgatgca gtctgcggat   13380
gcatcaacgt tttttaaacgg gtttgcggtg taagtgcagc ccgtcttaca ccgtgcggca   13440
caggcactag tactgatgtc gtctacaggg cttttgatat ttacaacgaa aaagttgctg   13500
gttttgcaaa gttcctaaaa actaattgct gtcgcttcca ggagaaggat gaggaaggca   13560
atttattaga ctcttacttt gtagttaaga ggcatactat gtctaactac caacatgaag   13620
```

```
agactattta taacttggtt aaagattgtc cagcggttgc tgtccatgac ttttcaagt      13680 ttagagtaga tggtgacatg gtaccacata tatcacgtca gcgtctaact aaatacacaa     13740
tggctgattt agtctatgct ctacgtcatt ttgatgaggg taattgtgat acattaaaag     13800
aaatactcgt cacatacaat tgctgtgatg atgattattt caataagaag gattggtatg     13860
acttcgtaga gaatcctgac atcttacgcg tatatgctaa cttaggtgag cgtgtacgcc     13920
aatcattatt aaagactgta caattctgcg atgctatgcg tgatgcaggc attgtaggcg     13980
tactgacatt agataatcag gatcttaatg ggaactggta cgatttcggt gatttcgtac     14040
aagtagcacc aggctgcgga gttcctattg tggattcata ttactcattg ctgatgccca     14100
tcctcacttt gactagggca ttggctgctg agtcccatat ggatgctgat ctcgcaaaac     14160
cacttattaa gtgggatttg ctgaaatatg attttacgga agagagactt tgtctcttcg     14220
accgttattt taaatattgg gaccagacat accatcccaa ttgtattaac tgtttggatg     14280
ataggtgtat ccttcattgt gcaaacttta atgtgttatt ttctactgtg tttccaccta     14340
caagttttgg accactagta agaaaaatat tgtagatgg tgttcctttt gttgtttcaa      14400
ctggatacca ttttcgtgag ttaggagtcg tacataatca ggatgtaaac ttacatagct     14460
cgcgtctcag tttcaaggaa cttttagtgt atgctgctga tccagctatg catgcagctt     14520
ctggcaattt attgctagat aaacgcacta catgcttttc agtagctgca ctaacaaaca     14580
atgttgcttt tcaaactgtc aaacccggta attttaataa agactttat gactttgctg       14640 tgtctaaagg tttctttaag gaaggaagtt ctgttgaact aaaacacttc ttctttgctc     14700
aggatggcaa cgctgctatc agtgattatg actattatcg ttataatctg ccaacaatgt     14760
gtgatatcag acaactccta ttcgtagttg aagttgttga taaatacttt gattgttacg     14820
atggtggctg tattaatgcc aaccaagtaa tcgttaacaa tctggataaa tcagctggtt     14880
tcccatttaa taaatggggt aaggctagac tttattatga ctcaatgagt tatgaggatc     14940
aagatgcact tttcgcgtat actaagcgta atgtcatccc tactataact caaatgaatc     15000
ttaagtatgc cattagtgca aagaatagag ctcgcaccgt agctggtgtc tctatctgta     15060
gtactatgac aaatagacag tttcatcaga aattattgaa gtcaatagcc gccactagag     15120
gagctactgt ggtaattgga acaagcaagt tttacggtgg ctggcataat atgttaaaaa     15180
ctgtttacag tgatgtagaa actccacacc ttatgggttg ggattatcca aaatgtgaca     15240
gagccatgcc taacatgctt aggataatgg cctctcttgt tcttgctcgc aaacataaca     15300
cttgctgtaa cttatcacac cgtttctaca ggttagctaa cgagtgtgcg caagtattaa     15360
gtgagatggt catgtgtggc ggctcactat atgttaaacc aggtggaaca tcatccggtg     15420
atgctacaac tgcttatgct aatagtgtct ttaacatttg tcaagctgtt acagccatgt     15480
taaatgcact tctttcaact gatggtaata agatagctga caagtatgtc cgcaatctac     15540
aacacaggct ctatgagtgt ctctatagaa atagggatgt tgatcatgaa ttcgtggatg     15600
agttttacgc ttacctgcgt aaacatttct ccatgatgat tctttctgat gatgccgttg     15660
tgtgctataa cagtaactat gcggctcaag gtttagtagc tagcattaag aactttaagg     15720 cagttctttta ttatcaaaat aatgtgttca tgtctgaggc aaaatgttgg actgagactg     15780
accttactaa aggacctcac gaattttgct cacagcatac aatgctagtt aaacaaggag     15840
atgattacgt gtacctgcct tacccagatc catcaagaat attaggcgca ggctgttttg     15900
tcgatgatat tgtcaaaaca gatggtacac ttatgattga aaggttcgtg tcactggcta     15960
```

```
ttgatgctta cccacttaca aaacatccta atcaggagta tgctgatgtc tttcacttgt   16020
atttacaata cattagaaag ttacatgatg agcttactgg ccacatgttg gacatgtatt   16080
ccgtaatgct aactaatgat aacacctcac ggtactggga acctgagttt tatgaggcta   16140
tgtacacacc acatacagtc ttgcaggctg taggtgcttg tgtattgtgc aattcacaga   16200
cttcacttcg ttgcggtgcc tgtattagga gaccattcct atgttgcaag tgctgctatg   16260
accatgtcat ttcaacatca cacaaattag tgttgtctgt taatccctat gtttgcaatg   16320
ccccaggttg tgatgtcact gatgtgacac aactgtatct aggaggtatg agctattatt   16380
gcaagtcaca taagcctccc attagttttc cattatgtgc taatggtcag gttttggtt    16440 tatacaaaaa cacatgtgta ggcagtgaca atgtcactga cttcaatgcg atagcaacat   16500
gtgattggac taatgctggc gattacatac ttgccaacac ttgtactgag agactcaagc   16560
ttttcgcagc agaaacgctc aaagccactg aggaaacatt taagctgtca tatggtattg   16620
ccactgtacg cgaagtactc tctgacagag aattgcatct ttcatgggag gttggaaaac   16680
ctagaccacc attgaacaga aactatgtct ttactggtta ccgtgtaact aaaaatagta   16740
aagtacagat tggagagtac acctttgaaa aggtgactga tggtgatgct gttgtgtaca   16800
gaggtactac gacatacaag ttgaatgttg gtgattactt tgtgttgaca tctcacactg   16860
taatgccact tagtgcacct actctagtgc cacaagagca ctatgtgaga attactggct   16920
tgtacccaac actcaacatc tcagatgagt tttctagcaa tgttgcaaat tatcaaaagg   16980
tcggcatgca aaagtactct acactccaag gaccacctgg tactggtaag agtcattttg   17040
ccatcggact tgctctctat tacccatctg ctcgcatagt gtatacggca tgctctcatg   17100
cagctgttga tgccctatgt gaaaaggcat taaaatattt gcccatagat aaatgtagta   17160
gaatcatacc tgcgcgtgcg cgcgtagagt gttttgataa attcaaagtg aattcaacac   17220
tagaacagta tgttttctgc actgtaaatg cattgccaga aacaactgct gacattgtag   17280
tctttgatga aatctctatg ctactaattt atgacttgag tgttgtcaat gctagacttc   17340
gtgcaaaaca ctacgtctat attggcgatc ctgctcaatt accagccccc cgcacattgc   17400
tgactaaagg cacactagaa ccagaatatt ttaattcagt gtgcagactt atgaaaacaa   17460
taggtccaga catgttcctt ggaacttgtc gccgttgtcc tgctgaaatt gttgacactg   17520
tgagtgcttt agtttatgac aataagctaa aagcacacaa ggataagtca gctcaatgct   17580
tcaaaatgtt ctacaaaggt gttattacac atgatgtttc atctgcaatc aacagacctc   17640
aaataggcgt tgtaagagaa tttcttacac gcaatcctgc ttggagaaaa gctgttttta   17700
tctcacctta taattcacag aacgctgtag cttcaaaaat cttaggattg cctacgcaga   17760
ctgttgattc atcacagggt tctgaatatg actatgtcat attcacacaa actactgaaa   17820
cagcacactc ttgtaatgtc aaccgcttca atgtggctat cacaagggca aaaattggca   17880
ttttgtgcat aatgtctgat agagatcttt atgacaaact gcaatttaca agtctagaaa   17940
taccacgtcg caatgtggct acattacaag cagaaaatgt aactggactt tttaaggact   18000
gtagtaagat cattactggt cttcatccta cacaggcacc tacacacctc agcgttgata   18060
taaagttcaa gactgaagga ttatgtgttg acataccagg cataccaaag gacatgacct   18120
accgtagact catctctatg atgggtttca aaatgaatta ccaagtcaat ggttacccta   18180
atatgtttat cacccgcgaa gaagctattc gtcacgttcg tgcgtggatt ggctttgatg   18240
tagagggctg tcatgcaact agagatgctg tgggtactaa cctacctctc cagctaggat   18300
tttctacagg tgttaactta gtagctgtac cgactggtta tgttgacact gaaaataaca   18360
```

```
cagaattcac cagagttaat gcaaaacctc caccaggtga ccagtttaaa catcttatac   18420
cactcatgta taaaggcttg ccctggaatg tagtgcgtat taagatagta caaatgctca   18480
gtgatacact gaaaggattg tcagacagag tcgtgttcgt cctttgggcg catggctttg   18540
agcttacatc aatgaagtac tttgtcaaga ttggacctga agaacgtgt tgtctgtgtg    18600 acaaacgtgc aacttgcttt tctacttcat cagatactta tgcctgctgg aatcattctg   18660
tgggttttga ctatgtctat aacccattta tgattgatgt tcagcagtgg ggctttacgg   18720
gtaaccttca gagtaaccat gaccaacatt gccaggtaca tggaaatgca catgtggcta   18780
gttgtgatgc tatcatgact agatgtttag cagtccatga gtgctttgtt aagcgcgttg   18840
attggtctgt tgaataccct attataggag atgaactgag ggttaattct gcttgcagaa   18900
aagtacaaca catggttgtg aagtctgcat tgcttgctga taagtttcca gttcttcatg   18960
acattggaaa tccaaaggct atcaagtgtg tgcctcaggc tgaagtagaa tggaagttct   19020
acgatgctca gccatgtagt gacaaagctt acaaaataga ggaactcttc tattcttatg   19080
ctacacatca cgataaattc actgatggtg tttgtttgtt ttggaattgt aacgttgatc   19140
gttacccagc caatgcaatt gtgtgtaggt ttgacacaag agtcttgtca aacttgaact   19200
taccaggctg tgatggtggt agtttgtatg tgaataagca tgcattccac actccagctt   19260
tcgataaaag tgcatttact aatttaaagc aattgccttt cttttactat tctgatagtc   19320
cttgtgagtc tcatggcaaa caagtagtgt cggatattga ttatgttcca ctcaaatctg   19380
ctacgtgtat tacacgatgc aatttaggtg gtgctgtttg cagacaccat gcaaatgagt   19440
accgacagta cttggatgca tataatatga tgatttctgc tggatttagc ctatggattt   19500
acaaacaatt tgatacttat aacctgtgga atacatttac caggttacag agtttagaaa   19560
atgtggctta taatgttgtt aataaaggac actttgatgg acacgccggc gaagcacctg   19620
tttccatcat taataatgct gtttacacaa aggtagatgg tattgatgtg gagatctttg   19680
aaaataagac aacacttcct gttaatgttg catttgagct ttgggctaag cgtaacatta   19740
aaccagtgcc agagattaag atactcaata atttgggtgt tgatatcgct gctaatactg   19800
taatctggga ctacaaaaga gaagccccag cacatgtatc tacaataggt gtctgcacaa   19860
tgactgacat tgccaagaaa cctactgaga gtgcttgttc ttcacttact gtcttgtttg   19920
atggtagagt ggaaggacag gtagaccttt ttagaaacgc ccgtaatggt gttttaataa   19980
cagaaggttc agtcaaaggt ctaacacctt caaagggacc agcacaagct agcgtcaatg   20040
gagtcacatt aattggagaa tcagtaaaaa cacagtttaa ctactttaag aaagtagacg   20100
gcattattca acagttgcct gaaacctact ttactcagag cagagactta gaggatttta   20160
agcccagatc acaaatggaa actgactttc tcgagctcgc tatggatgaa ttcatacagc   20220
gatataagct cgagggctat gccttcgaac acatcgttta tggagatttc agtcatggac   20280
aacttggcgg tcttcattta atgataggct tagccaagcg ctcacaagat tcaccactta   20340
aattagagga ttttatccct atggacagca cagtgaaaaa ttacttcata acagatgcgc   20400
aaacaggttc atcaaaatgt gtgtgttctg tgattgatct tttacttgat gactttgtcg   20460
agataataaa gtcacaagat ttgtcagtga tttcaaaagt ggtcaaggtt acaattgact   20520
atgctgaaat ttcattcatg ctttggtgta aggatggaca tgttgaaacc ttctacccaa   20580
aactacaagc aagtcgagcg tggcaaccag gtgttgcgat gcctaacttg tacaagatgc   20640
aaagaatgct tcttgaaaag tgtgaccttc agaattatgg tgaaaatgct gttataccaa   20700
```

-continued

```
aaggaataat gatgaatgtc gcaaagtata ctcaactgtg tcaatactta aatacactta   20760
ctttagctgt accctacaac atgagagtta ttcactttgg tgctggctct gataaaggag   20820
ttgcaccagg tacagctgtg ctcagacaat ggttgccaac tggcacacta cttgtcgatt   20880
cagatcttaa tgacttcgtc tccgacgcat attctacttt aattggagac tgtgcaacag   20940
tacatacggc taataaatgg gaccttatta ttagcgatat gtatgaccct aggaccaaac   21000
atgtgacaaa agagaatgac tctaaagaag gttttttcac ttatctgtgt ggatttataa   21060
agcaaaaact agccctgggt ggttctatag ctgtaaagat aacagagcat tcttggaatg   21120
ctgacccttta caagcttatg ggccatttct catggtggac agcttttgtt acaaatgtaa   21180
atgcatcatc atcggaagca ttttttaattg gggctaacta tcttggcaag ccgaaggaac   21240
aaattgatgg ctataccatg catgctaact acatttttctg gaggaacaca aatcctatcc   21300
agttgtcttc ctattcactc tttgacatga gcaaatttcc tcttaaatta agaggaactg   21360
ctgtaatgtc tcttaaggag aatcaaatca atgatatgat ttattctctt ctggaaaaag   21420
gtaggcttat cattagagaa acaacagag ttgtggtttc aagtgatatt cttgttaaca   21480
actaaacgaa catgtttatt ttcttattat ttcttactct cactagtggt agtgaccttg   21540
accggtgcac cactttttgat gatgttcaag ctcctaatta cactcaacat acttcatcta   21600
tgaggggggt ttactatcct gatgaaattt ttagatcaga cactctttat ttaactcagg   21660
atttattttct tccattttat tctaatgtta cagggtttca tactattaat catacgtttg   21720
gcaaccctgt catacctttt aaggatggta tttattttgc tgccacagag aaatcaaatg   21780
ttgtccgtgg ttgggttttt ggttctacca tgaacaacaa gtcacagtcg gtgattatta   21840
ttaacaattc tactaatgtt gttatacgag catgtaactt tgaattgtgt gacaaccctt   21900
tctttgctgt ttctaaaccc atgggtacac agacacatac tatgatattc gataatgcat   21960
ttaattgcac tttcgagtac atatctgatg ccttttcgct tgatgtttca gaaaagtcag   22020
gtaattttaa acacttacga gagtttgtgt ttaaaaataa agatgggttt ctctatgttt   22080
ataaggcta tcaacctata gatgtagttc gtgatctacc ttctggtttt aacactttga   22140
aacctatttt taagttgcct cttggtatta acattacaaa ttttagagcc attcttacag   22200
cctttttcacc tgctcaagac atttggggca cgtcagctgc agcctatttt gttggctatt   22260
taaagccaac tacattttatg ctcaagtatg atgaaaatgg tacaatcaca gatgctgttg   22320
attgttctca aaatccactt gctgaactca aatgctctgt taagagcttt gagattgaca   22380
aaggaattta ccagacctct aatttcaggg ttgttccctc aggagatgtt gtgagattcc   22440
ctaatattac aaacttgtgt cctttttggag aggtttttaa tgctactaaa ttccccttctg   22500
tctatgcatg ggagagaaaa aaaatttcta attgtgttgc tgattactct gtgctctaca   22560
actcaacatt tttttcaacc tttaagtgct atggcgtttc tgccactaag ttgaatgatc   22620
tttgcttctc caatgtctat gcagattctt ttgtagtcaa gggagatgat gtaagacaaa   22680
tagcgccagg acaaactggt gttattgctg attataatta taaattgcca gatgatttca   22740
tgggttgtgt ccttgcttgg aatactagga acattgatgc tacttcaact ggtaattata   22800
attataaata taggtatctt agacatggca agcttaggcc ctttgagaga gacatatcta   22860
atgtgccttt ctcccctgat ggcaaacctt gcaccccacc tgctcttaat tgttattggc   22920
cattaaatga ttatggtttt tacaccacta ctggcattgg ctaccaacct tacagagttg   22980
tagtactttc ttttgaactt ttaaatgcac cggccacggt ttgtggacca aaattatcca   23040
ctgaccttat taagaaccag tgtgtcaatt ttaattttaa tggactcact ggtactggtg   23100
```

```
tgttaactcc ttcttcaaag agatttcaac catttcaaca atttggccgt gatgtttctg   23160
atttcactga ttccgttcga gatcctaaaa catctgaaat attagacatt tcaccttgcg   23220 cttttgggg  tgtaagtgta attacacctg gaacaaatgc ttcatctgaa gttgctgttc   23280
tatatcaaga tgttaactgc actgatgttt ctacagcaat tcatgcagat caactcacac   23340
cagcttggcg catatattct actggaaaca atgtattcca gactcaagca ggctgtctta   23400
taggagctga gcatgtcgac acttcttatg agtgcgacat tcctattgga gctggcattt   23460
gtgctagtta ccatacagtt tctttattac gtagtactag ccaaaaatct attgtggctt   23520
atactatgtc tttaggtgct gatagttcaa ttgcttactc taataacacc attgctatac   23580
ctactaactt ttcaattagc attactacag aagtaatgcc tgtttctatg ctaaaaacct   23640
ccgtagattg taatatgtac atctgcggag attctactga atgtgctaat ttgcttctcc   23700
aatatggtag cttttgcaca caactaaatc gtgcactctc aggtattgct gctgaacagg   23760
atcgcaacac acgtgaagtg ttcgctcaag tcaaacaaat gtacaaaacc ccaactttga   23820
aatattttgg tggttttaat ttttcacaaa tattacctga ccctctaaag ccaactaaga   23880
ggtcttttat tgaggacttg ctctttaata aggtgacact cgctgatgct ggcttcatga   23940
agcaatatgg cgaatgccta ggtgatatta atgctagaga tctcatttgt gcgcagaagt   24000
tcaatggact tacagtgttg ccacctctgc tcactgatga tatgattgct gcctacactg   24060
ctgctctagt tagtggtact gccactgctg gatggacatt tggtgctggc gctgctcttc   24120
aaataccttt tgctatgcaa atggcatata ggttcaatgg cattggagtt acccaaaatg   24180
ttctctatga gaaccaaaaa caaatcgcca accaatttaa caaggcgatt agtcaaattc   24240
aagaatcact tacaacaaca tcaactgcat tgggcaagct gcaagacgtt gttaaccaga   24300
atgctcaagc attaaacaca cttgttaaac aacttagctc taattttggt gcaatttcaa   24360
gtgtgctaaa tgatatcctt tcgcgacttg ataaagtcga ggcggaggta caaattgaca   24420
ggttaattac aggcagactt caaagccttc aaacctatgt aacacaacaa ctaatcaggg   24480
ctgctgaaat cagggcttct gctaatcttg ctgctactaa aatgtctgag tgtgttcttg   24540
gacaatcaaa aagagttgac ttttgtggaa agggctacca ccttatgtcc ttcccacaag   24600
cagccccgca tggtgttgtc ttcctacatg tcacgtatgt gccatcccag gagaggaact   24660
tcaccacagc gccagcaatt tgtcatgaag caaagcata  cttccctcgt gaaggtgttt   24720
ttgtgtttaa tggcacttct tggtttatta cacagaggaa cttctttctt ccacaaataa   24780
ttactacaga caatacattt gtctcaggaa attgtgatgt cgttattggc atcattaaca   24840
acacagttta tgatcctctg caacctgagc ttgactcatt caaagaagag ctggacaagt   24900
acttcaaaaa tcatacatca ccagatgttg atcttggcga catttcaggc attaacgctt   24960
ctgtcgtcaa cattcaaaaa gaaattgacc gcctcaatga ggtcgctaaa aatttaaatg   25020
aatcactcat tgaccttcaa gaattgggaa aatatgagca atatattaaa tggccttggt   25080
atgtttggct cggcttcatt gctggactaa ttgccatcgt catggttaca atcttgcttt   25140
gttgcatgac tagttgttgc agttgcctca agggtgcatg ctcttgtggt tcttgctgca   25200
agtttgatga ggatgactct gagccagttc tcaagggtgt caaattacat tacacataaa   25260
cgaacttatg gatttgttta tgagattttt tactcttgga tcaattactg cacagccagt   25320
aaaaattgac aatgcttctc ctgcaagtac tgttcatgct acagcaacga taccgctaca   25380
agcctcactc ccttcggat  ggcttgttat tggcgttgca tttcttgctg tttttcagag   25440
```

```
cgctaccaaa ataattgcgc tcaataaaag atggcagcta gcccttttata agggcttcca   25500 gttcatttgc aatttactgc tgctatttgt taccatctat tcacatcttt tgcttgtcgc   25560
tgcaggtatg gaggcgcaat ttttgtacct ctatgccttg atatattttc tacaatgcat   25620
caacgcatgt agaattatta tgagatgttg gctttgttgg aagtgcaaat ccaagaaccc   25680
attactttat gatgccaact actttgtttg ctggcacaca cataactatg actactgtat   25740
accatataac agtgtcacag atacaattgt cgttactgaa ggtgacggca tttcaacacc   25800
aaaactcaaa gaagactacc aaattggtgg ttattctgag gataggcact caggtgttaa   25860
agactatgtc gttgtacatg gctatttcac cgaagtttac taccagcttg agtctacaca   25920
aattactaca gacactggta ttgaaaatgc tacattcttc atctttaaca agcttgttaa   25980
agacccaccg aatgtgcaaa tacacacaat cgacggctct tcaggagttg ctaatccagc   26040
aatggatcca atttatgatg agccgacgac gactactagc gtgcctttgt aagcacaaga   26100
aagtgagtac gaacttatgt actcattcgt ttcggaagaa acaggtacgt taatagttaa   26160
tagcgtactt cttttttcttg ctttcgtggt attcttgcta gtcacactag ccatccttac   26220
tgcgcttcga ttgtgtgcgt actgctgcaa tattgttaac gtgagtttag taaaaccaac   26280
ggtttacgtc tactcgcgtg ttaaaaatct gaactcttct gaaggagttc ctgatcttct   26340
ggtctaaacg aactaactat tattattatt ctgtttggaa ctttaacatt gcttatcatg   26400
gcagacaacg gtactattac cgttgaggag cttaaacaac tcctggaaca atggaaccta   26460
gtaataggtt tcctattcct agcctggatt atgttactac aatttgccta ttctaatcgg   26520
aacaggtttt tgtacataat aaagcttgtt ttcctctggc tcttgtggcc agtaacactt   26580
gcttgttttg tgcttgctgc tgtctacaga attaattggg tgactggcgg gattgcgatt   26640
gcaatggctt gtattgtagg cttgatgtgg cttagctact tcgttgcttc cttcaggctg   26700
tttgctcgta cccgctcaat gtggtcattc aacccagaaa caaacattct tctcaatgtg   26760
cctctccggg ggacaattgt gaccagaccg ctcatggaaa gtgaacttgt cattggtgct   26820
gtgatcattc gtggtcactt gcgaatggcc ggacactccc tagggcgctg tgacattaag   26880
gacctgccaa aagagatcac tgtggctaca tcacgaacgc tttcttatta caaattagga   26940
gcgtcgcagc gtgtaggcac tgattcaggt tttgctgcat acaaccgcta ccgtattgga   27000
aactataaat taaatacaga ccacgccggt agcaacgaca atattgcttt gctagtacag   27060
taagtgacaa cagatgtttc atcttgttga cttccaggtt acaatagcag agatattgat   27120
tatcattatg aggactttca ggattgctat ttggaatctt gacgttataa taagttcaat   27180
agtgagacaa ttatttaagc ctctaactaa gaagaattat tcggagttag atgatgaaga   27240
acctatggag ttagattatc cataaaacga acatgaaaat tattctcttc ctgacattga   27300
ttgtatttac atcttgcgag ctatatcact atcaggagtg tgttagaggt acgactgtac   27360
tactaaaaga accttgccca tcaggaacat acgagggcaa ttcaccattt caccctcttg   27420
ctgacaataa atttgcacta acttgcacta gcacacactt tgcttttgct tgtgctgacg   27480
gtactcgaca tacctatcag ctgcgtgcaa gatcagtttc accaaaactt ttcatcagac   27540
aagaggaggt tcaacaagag ctctactcgc cacttttttct cattgttgct gctctagtat   27600
ttttaatact tgcttcacc attaagagaa agacagaatg aatgagctca ctttaattga   27660
cttctatttg tgcttttttag cctttctgct attccttgtt ttaataatgc ttattatatt   27720
ttggttttca ctcgaaatcc aggatctaga agaaccttgt accaaagtct aaacgaacat   27780
gaaacttctc attgttttga cttgtatttc tctatgcagt tgcatatgca ctgtagtaca   27840
```

-continued

```
gcgctgtgca tctaataaac ctcatgtgct tgaagatcct tgtaaggtac aacactaggg    27900
gtaatactta tagcactgct tggctttgtg ctctaggaaa ggttttacct tttcatagat    27960
ggcacactat ggttcaaaca tgcacaccta atgttactat caactgtcaa gatccagctg    28020
gtggtgcgct tatagctagg tgttggtacc ttcatgaagg tcaccaaact gctgcattta    28080
gagacgtact tgttgtttta aataaacgaa caaattaaaa tgtctgataa tggaccccaa    28140
tcaaaccaac gtagtgcccc ccgcattaca tttggtggac ccacagattc aactgacaat    28200
aaccagaatg gaggacgcaa tggggcaagg ccaaacagcc gccgaccca aggtttaccc    28260
aataatactg cgtcttggtt cacagctctc actcagcatg gcaaggagga acttagattc    28320
cctcgaggcc agggcgttcc aatcaacacc aatagtggtc cagatgacca aattggctac    28380
taccgaagag ctaccgacg agttcgtggt ggtgacggaa aaatgaaaga gctcagcccc    28440
agatggtact tctattacct aggaactggc ccagaagctt cacttccta cggcgctaac    28500
aaagaaggca tcgtatgggt tgcaactgag ggagccttga atacacccaa agaccacatt    28560
ggcacccgca atcctaataa caatgctgcc accgtgctac aacttcctca aggaacaaca    28620
ttgccaaaag gcttctacgc agagggaagc agaggcggca gtcaagcctc ttctcgctcc    28680
tcatcacgta gtcgcggtaa ttcaagaaat tcaactcctg gcagcagtag gggaaattct    28740
cctgctcgaa tggctagcgg aggtggtgaa actgccctcg cgctattgct gctagacaga    28800
ttgaaccagc ttgagagcaa agtttctggt aaaggccaac aacaacaagg ccaaactgtc    28860
actaagaaat ctgctgctga ggcatctaaa aagcctcgcc aaaaacgtac tgccacaaaa    28920
cagtacaacg tcactcaagc atttgggaga cgtggtccag aacaaaccca aggaaatttc    28980
ggggaccaag acctaatcag acaaggaact gattacaaac attggccgca aattgcacaa    29040
tttgctccaa gtgcctctgc attctttgga atgtcacgca ttggcatgga agtcacacct    29100
tcgggaacat ggctgactta tcatggagcc attaaattgg atgacaaaga tccacaattc    29160
aaagacaacg tcatactgct gaacaagcac attgacgcat acaaaacatt cccaccaaca    29220
gagcctaaaa aggacaaaaa gaaaaagact gatgaagctc agcctttgcc gcagagacaa    29280
aagaagcagc ccactgtgac tcttcttcct gcggctgaca tggatgattt ctccagacaa    29340
cttcaaaatt ccatgagtgg agcttctgct gattcaactc aggcataaac actcatgatg    29400
accacacaag gcagatgggc tatgtaaacg ttttcgcaat tccgtttacg atacatagtc    29460
tactcttgtg cagaatgaat tctcgtaact aaacagcaca agtaggttta gttaacttta    29520
atctcacata gcaatcttta atcaatgtgt aacattaggg aggacttgaa agagccacca    29580
cattttcatc gaggccacgc ggagtacgat cgagggtaca gtgaataatg ctagggagag    29640
ctgcctatat ggaagagccc taatgtgtaa aattaatttt agtagtgcta tccccatgtg    29700
attttaatag cttcttagga gaatgacaaa aaaaaaaaaa aaaaaaaaa a              29751
```

<210> SEQ ID NO 2
<211> LENGTH: 383
<212> TYPE: RNA
<213> ORGANISM: Hepatitis C virus

<400> SEQUENCE: 2

```
gccagccccc ugauggggc gacacuccac cauagaucac uccccuguga ggaacuacug      60
ucuucaccca gaaagcgucu agccauggcg uuaguaugag ugucgugcag ccuccaggac     120
cccccucc gggagagcca uaguggucug cggaaccggu gaguacaccg gaauugccag     180
```

```
gacgaccggg uccuuucuug gaucaacccg cucaaugccu ggagauuugg gcgugccccc    240
gcaagacugc uagccgagua guguugggguc gcgaaaggcc uugugguacu gccugauagg   300
gugcuugcga gugcccgggg aggucucgua gaccgugcac caugagcacg aauccuaaac   360
cucaaagaaa aaccaaacgu aac                                            383
```

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
guacugccug auagggugcu u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gcacccuauc aggcaguacu u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cguacgcgga auacuucgau u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucgaaguauu ccgcguacgu u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuuacgcuga guacuucgau u                                              21

<210> SEQ ID NO 8
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 8
ucgaaguacu cagcguaagu u                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
aucucuacgg ugguccuaau u                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uuaggaccac cguagagauu u                                              21

<210> SEQ ID NO 11
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cccugugagg aacuacuguc uuc                                            23

<210> SEQ ID NO 12
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uacugucuuc acgcagaaag cgu                                            23

<210> SEQ ID NO 13
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cgagacugcu agccgaguag ugu                                            23

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 14
gaauccuaaa ccucaaagaa aaa                                              23

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggucagaucg ucgguggagu uua                                              23

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gguaagguca ucgauacccu cac                                              23

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
acggcgugaa cuaugcaaca ggg                                              23

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ccgguugcuc cuuuucuauc uuc                                              23

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gcucuucaua cggauuccaa uac                                              23

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 20
cauacggauu ccaauacucu ccu                                          23

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uuugacucaa cggucacuga gaa                                          23

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ccuucacgga ggcuaugacu aga                                          23

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
auacgacuug gaguugauaa cau                                          23

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
auuccuggcu aggcaacauc auc                                          23

<210> SEQ ID NO 25
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuguggcaag uaccucuuca acu                                          23

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 26
auguggugcc uacuccuacu uuc                                          23

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27 cuuuggugc uccaucuuag ccc                                           23

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gucacggcua gcugugaaag guc                                          23

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
agccgcuuga cugcagagag ugc                                          23

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cugugaggaa cuacugucuu c                                            21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
agacaguagu uccucacagg g                                            21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
```
cugucuucac gcagaaagcg u                                                  21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33 gcuucugcg ugaagacagu a                                                   21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
agacugcuag ccgaguagug u                                                  21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
acuacucggc uagcagucuc g                                                  21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
auccuaaacc ucaaagaaaa a                                                  21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uuucuuugag guuuaggauu c                                                  21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ucagaucguc gguggaguuu a                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aacuccaccg acgaucugac c                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uaaggucauc gauacccuca c                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gaggguaucg augaccuuac c                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggcgugaacu augcaacagg g                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cuguugcaua guucacgccg u                                              21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gguugcuccu uuucuaucuu c                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
agauagaaaa ggagcaaccg g                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ucuucauacg gauuccaaua c                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
auuggaaucc guaugaagag c                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uacggauucc aauacucucc u                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gagaguauug gaauccguau g                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ugacucaacg gucacugaga a                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cucagugacc guugagucaa a                                              21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uucacggagg cuaugacuag a                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uagucauagc cuccgugaag g                                              21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
acgacuugga guugauaaca u                                              21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
guuaucaacu ccaagucgua u                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uccuggcuag gcaacaucau c                                              21

```
<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ugauguugcc uagccaggaa u                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
guggcaagua ccucuucaac u                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uugaagaggu acuugccaca a                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
guggugccua cuccuacuuu c                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aaguaggagu aggcaccaca u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uugguggcuc caucuuagcc c                                              21

<210> SEQ ID NO 63
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gcuaagaugg agccaccaaa g                                               21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cacggcuagc ugugaaaggu c                                               21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ccuuucacag cuagccguga c                                               21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ccgcuugacu gcagagagug c                                               21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
acucucugca gucaagcggc u                                               21

<210> SEQ ID NO 68
<211> LENGTH: 10
<212> TYPE: DNA
<213> ORGANISM: SARS coronavirus

<400> SEQUENCE: 68
taaaacgaac                                                            10
```

MODIFIED SMALL INTERFERING RNA MOLECULES AND METHODS OF USE

This application is a divisional application of U.S. Utility patent application Ser. No. 11/664,008 filed 27 Mar. 2007, which claims priority to U.S. Provisional Application Ser. No. 60/614,955 filed 1 Oct. 2004, the contents of which are incorporated herein by reference in their entirety.

BACKGROUND OF THE INVENTION

The present invention relates to the field of nucleic acid detection and to the phenomenon of RNA silencing, or RNA interference (RNAi). RNA silencing constitutes a phenomenon wherein non-coding RNA molecules mediate specific gene suppression in an organism. In nature, the phenomenon protects an organism's genome from foreign, invading nucleic acids such as transposons, trangenes and viral genes.

The introduction of double-stranded RNA (dsRNA) into a cell triggers RNA silencing, which then degrades endogenous mRNA corresponding to the dsRNA. RNA silencing pathways involve a conversion of dsRNA into short interfering RNAs (siRNAs) that direct ribonucleases to homologous mRNA targets (Baulcombe et al., 2001). An enzyme called Dicer processes the dsRNA into siRNAs, which are 20-25 nucleotides long. The siRNAs then assemble into endoribonuclease-containing complexes known as RNA-induced silencing complexes (RISCs). Subsequently, the siRNAs guide the RISCs to complementary RNA molecules, where the RISCs cleave and destroy the target mRNA. Small amounts of dsRNA can silence a large amount of target mRNA due to an amplification component of RNA silencing (Fire et al., *Nature,* 391:806-811 (1998)).

The first evidence that dsRNA produces efficient gene silencing through RNAi came from studies on the nematode *Caenorhabditis elegans* (Fire et al., *Nature,* 391:806-811 (1998) and U.S. Pat. No. 6,506,559). Later studies in the fruit fly *Drosophila melanogaster* demonstrated that RNAi is a multi-step mechanism (Elbashir et al., *Genes Dev.,* 15(2): 188-200 (2001)).

Although dsRNA can mediate gene-specific interference in mammalian cells (Wianny, F. and Zernicka-Goetz, M., Nature Cell Biol. 2:70-75 (2000) Svoboda, P. et al., Development 17:4147-4156 (2000)), the use of RNAi in mammalian somatic cells is often limited by a triggering of dsRNA-dependent protein kinase (PKR), which inactivates the translation factor eIF2a, causes a generalized suppression of protein synthesis and often times causes apoptosis (Gil, J. and Esteban, M., Apoptosis 5:107-114 (2000)).

Recently, siRNA of approximately 21 or 22 base pairs in length, corresponding to targeted RNA or DNA sequences, were shown to disrupt the expression of the targeted sequences in mammalian cells (Elbashir, S. M., et al., Nature 411: 494-498 (2001)). However, it is not clear that all RNA or DNA sequences of a mammalian cell's genome are susceptible to siRNA. It is also uncertain that every mammalian cell type possesses the necessary machinery for effectuating gene-specific suppression using siRNA. Further, siRNA is of limited use for at least two reasons: (a) the transient nature of the suppression effect seen in cells where the siRNA has been administered, and (b) the necessity for chemical synthesis of siRNAs before their use (Tuschl, T., Nature Biotech., 20: 446-448 (2002)). Also, since siRNAs are unstable in vivo, their long-term effectiveness is limited.

An invention that addresses these challenges will improve the utility of RNAi for treating human disease at the level of nucleic acid activity. In particular, such an invention will make RNAi a more practical therapy for viral infections, such as infections with HCV. Current therapies for such viral infections are very limited, and tend to have poor response rates.

SUMMARY OF THE INVENTION

In a first embodiment, the invention provides a double-stranded (dsRNA) molecule that mediates RNA interference in target cells wherein one or more of the pyrimidines in the dsRNA are modified to include a 2'-Fluorine.

In a second embodiment, the invention provides a small interfering RNA (siRNA) that mediates RNA interference in target cells wherein one or more of the pyrimidines in the siRNA are modified to include a 2'-Fluorine.

In a third embodiment, all of the pyrimidines in the dsRNA or siRNA molecules of the first and second embodiments are modified to include a 2'-Fluorine.

In a fourth embodiment, the 2'-Fluorine dsRNA or siRNA of the third embodiment's further modified to include a two base deoxynucleotide "TT" sequence at the 3' end of the dsRNA or siRNA.

In a fifth embodiment, the 2'-Fluorine dsRNA or siRNA of the third embodiment inhibits viral replication in infected cells.

In a sixth embodiment, the 2'-Fluorine dsRNA or siRNA of the fifth embodiment correspond to hepatitis C virus (HCV) nucleic acids and inhibit replication of HCV in hepatic cells.

In a seventh embodiment, there is provided a method for inactivating a virus in a patient comprising administering to said patient a 2'-Fluorine dsRNA or siRNA in an effective amount to inactivate said virus.

In an eighth embodiment, there is provided a method for inactivating a virus in a patient comprising administering to said patient a 2'-Fluorine dsRNA or siRNA in an effective amount to inactivate said virus, wherein all of the pyrimidines in the dsRNA or siRNA are modified to include a 2'-Fluorine.

In an ninth embodiment, there is provided a method for inactivating a virus in a patient comprising administering to said patient a 2'-Fluorine dsRNA or siRNA in an effective amount to inactivate said virus wherein the 2'-Fluorine dsRNA or siRNA is further modified to include a two base deoxynucleotide "TT" sequence at the 3' end of the dsRNA or siRNA.

In a tenth embodiment, there is provided a method for inactivating a virus in a patient comprising administering to said patient a 2'-Fluorine dsRNA or siRNA in an effective amount to inactivate said virus, wherein said virus is selected from the group consisting of hepatitis C virus (HCV), hepatitis A virus, hepatitis B virus, hepatitis D virus, hepatitis E virus, Ebola virus, influenza virus, rotavirus, reovirus, retrovirus, poliovirus, human papilloma virus (HPV), metapneumovirus and coronavirus.

In an eleventh embodiment, there is provided a method for inactivating a virus in a patient comprising administering to said patient a 2'-Fluorine dsRNA or siRNA in an effective amount to inactivate said virus, wherein said virus is HCV.

In a twelfth embodiment, there is provided a method of preparing an siRNA comprising the steps of:
(a) identifying a target nucleotide sequence in an HCV genome for designing a siRNA; and
(b) producing an siRNA that contains at least one pyrimidine in the siRNA which is modified to include a 2'-Fluorine.

In an thirteenth embodiment, there is provided a method of preparing an siRNA comprising the steps of:
(a) identifying a target nucleotide sequence in an HCV genome for designing a siRNA; and (b) producing an siRNA wherein all of the pyrimidines in the siRNA are modified to include a 2'-Fluorine.

In a fourteenth embodiment, there is provided a method of preparing an siRNA comprising the steps of:
(a) identifying a target nucleotide sequence in an HCV genome for designing a siRNA; and
(b) producing an siRNA wherein all of the pyrimidines in the siRNA are modified to include a 2'-Fluorine and wherein the 2'-Fluorine siRNA is further modified to include a two base deoxynucleotide "TT" sequence at the 3' end of the dsRNA or siRNA.

In a fifteenth embodiment, wherein said target nucleotide sequence in the fourteenth embodiment is selected from the group consisting of 5'-untranslated region (5'-UTR), 3'-untranslated region (3'-UTR), core, and NS3 helicase.

In a sixteenth embodiment, there is provided a dsRNA molecule of from about 10 to about 30 nucleotides that inhibits replication of HCV, wherein said dsRNA contains at least one pyrimidine in the siRNA which is modified to include a 2'-Fluorine.

In a seventeenth embodiment, there is provided a dsRNA molecule of from about 10 to about 30 nucleotides that inhibits replication of HCV, wherein all of the pyrimidines in the dsRNA are modified to include a 2'-Fluorine.

In an eighteenth embodiment, there is provided a dsRNA molecule of from about 10 to about 30 nucleotides that inhibits replication of HCV, wherein all of the pyrimidines in the dsRNA are modified to include a 2'-Fluorine and wherein the 2'-Fluorine dsRNA is further modified to include a two base deoxynucleotide "TT" sequence at the 3' end of the dsRNA.

In a nineteenth embodiment there is provided a method of inducing targeted RNA interference toward HCV in hepatic cells, comprising administering the dsRNA molecule of sixteenth embodiment to hepatic cells and wherein the nucleotide sequence of said dsRNA molecule corresponds to an HCV nucleotide sequence.

In a twentieth embodiment, there is provided a vector comprising a DNA segment encoding the dsRNA molecule of the sixteenth embodiment.

In a twenty first embodiment, there is provided a vector comprising a DNA segment encoding the dsRNA molecule of the sixteenth embodiment wherein the sense strand of said double-stranded RNA molecule is operably linked to a first promoter and wherein the antisense strand of said double-stranded RNA molecule of is operably linked to a second promoter.

In a twenty second embodiment, there is provided a host cell comprising the vector of the twentieth embodiment.

In a twenty third embodiment, the invention provides a method for the delivery of siRNA to hepatocytes in an animal for therapeutic purposes, including inactivating a virus in the animal. The method comprises administering a cholesterol-lowering drug to an animal in conjunction with the administration of a dsRNA or siRNA that is modified to further comprise a cholesterol as a receptor-binding ligand (cholesterol-siRNA). The cholesterol-lowering drug can be administered prior to, at the same time, or subsequent to the administration of the cholesterol-labeled siRNA. In one preferred embodiment, the cholesterol lowering drug is a statin.

BRIEF DESCRIPTION OF THE DRAWINGS

FIG. 2 provides sequences for several HCV-specific siRNAs that are useful for inducing RNAi toward HCV in hepatic cells. Each HCV-specific siRNA is identified by the designation provided in the first column.

FIG. 3 shows the nucleotide sequence of the SARS coronavirus.

FIG. 5 depicts a subgenomic HCV replicon contained in the hepatoma cell line Huh 7, which was used to test the efficacy of siRNA in human liver cells.

FIG. 6 depicts the dose response of normalized luciferase activity in Huh-7 cells containing the subgenomic HCV replicon (5-2 line), that were administered different concentrations of siRNA5. Luciferase activity, which was measured at 1, 2 and 3 days post-transfection, fell with increasing doses of siRNA. The luciferase assay was performed using a Luciferase assay system available from Promega Corp. (Madison, Wis.), according to the manufacturer's instructions.

FIG. 7 depicts the sequence specificity of siRNA5 for inducing HCV-directed RNAi in Huh-7 liver cells.

FIG. 8 demonstrates that siRNA5 is not toxic to Huh-7 cells. ATPase levels were assayed using an ATPase assay kit available from Promega Corp. (Madison, Wis.), according to the manufacturer's instructions.

FIG. 9 depicts the effects of siRNA5 on HCV replication in 21-5 cells (Huh-7 cells containing full-length HCV), as measured by RNA assay. RNA levels were assayed using a TaqMan™ RNA kit (F. Hoffman La-Roche, Switzerland), according to the manufacturer's instructions. Values are normalized.

& 18, 4 hr; Lanes 9 & 19, 8 hr; Lanes 10 & 20, 24 hr; Lanes 22, 24 hr; Lanes 23, 48 hr; Lanes 24, 120 hr; Lanes 25, 240 hr incubation, respectively.

Figure 14:
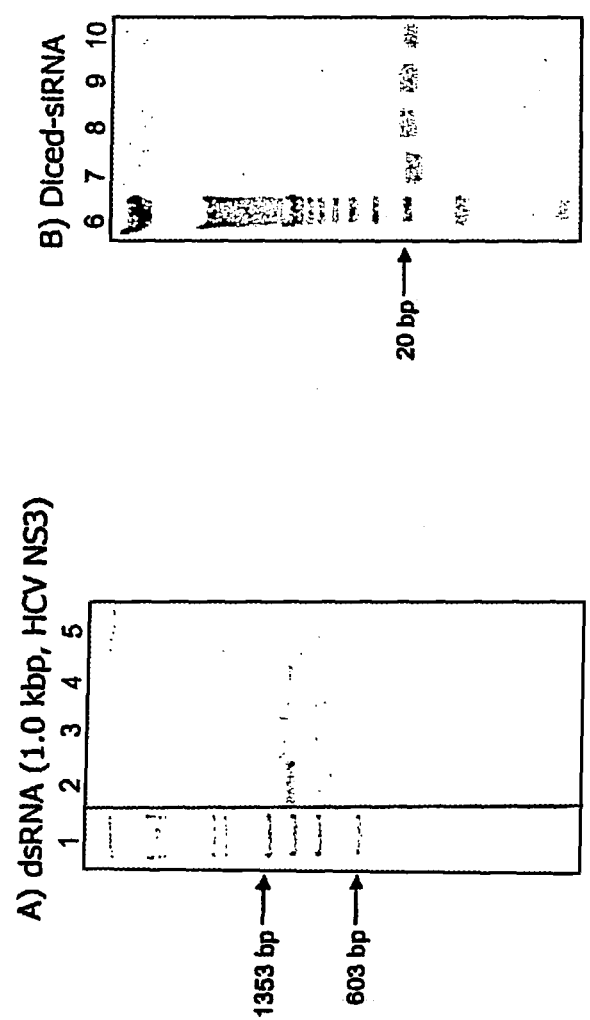

FIG. 14 demonstrates the use of recombinant human dicer to convert fluorinated dsRNA into 2'F-siRNA. The composition of the lanes is as follows: Lane 1: size marker, λ\HindIII+ φX174\HaeIII; Lane 2: ribo/ribo homoduplex RNA; Lane 3: ribo/2'-F heteroduplex RNA; Lane 4: 2'-F/ribo heteroduplex RNA; Lane 6: size marker, 10 bp DNA ladder; Lane 7: ribo/ribo homoduplex siRNA; Lane 8: ribo/2'-F heteroduplex siRNA; Lane 9: 2'-F/ribo heteroduplex siRNA; Lane 10: 2'-F/2'-F homoduplex siRNA.

Figure 15:
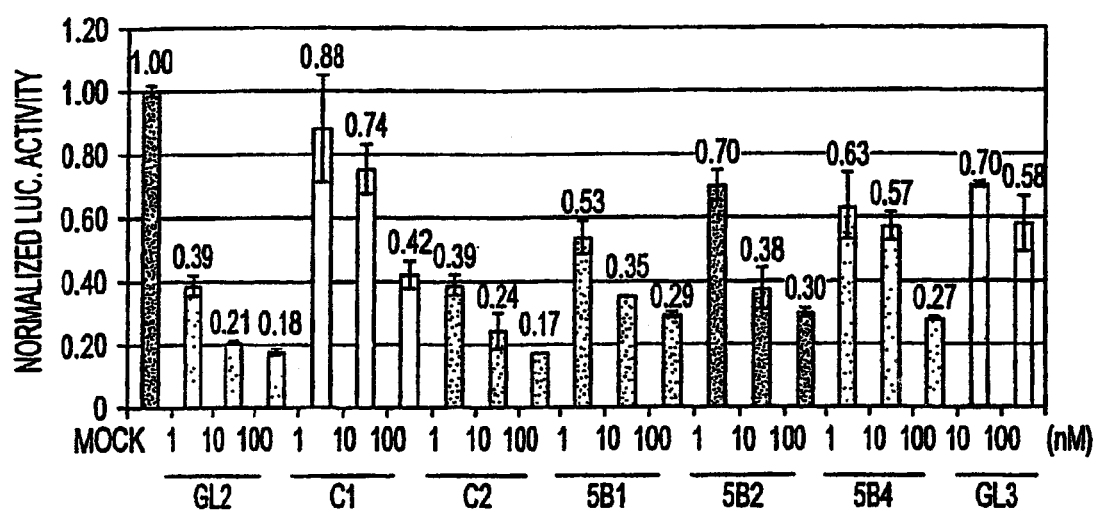

FIG. 15 shows a dose response of normalized luciferase activity in Huh-7 cells containing the subgenomic HCV replicon (5-2 line) to HCV-specific siRNAs. Luciferase activity fell with increasing doses of each siRNA.

Figure 16:
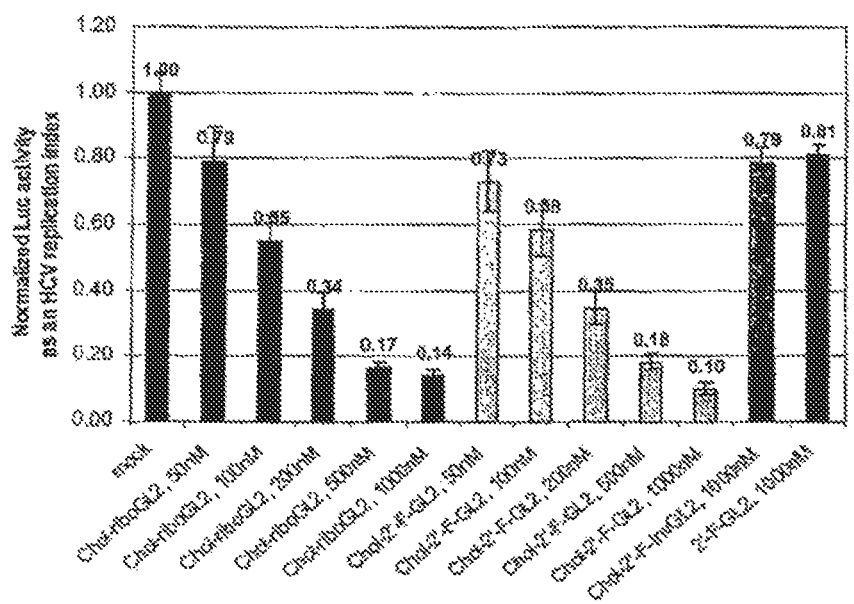

FIG. 16 shows that cholesterol shows a dose response of normalized luciferase activity in Huh-7 cells containing the subgenomic HCV replicon (5-2 line) to cholesterol-modified GL2 siRNA.

Figure 17:

FIG. 17 demonstrates the increased stability seen with an siRNA that has been modified to include 2-Fluoro pyrimidines replacing all of the pyrimidines (2-F-siRNA) and 2-Fluoro pyrimidines replacing all of the pyrimidines and also a two base deoxynucleotide "TT" sequence added to the 3' ends of the molecule in place of the ribolucleotide "UU" overhangs present in 2-F-siRNA (2'-F-siRNA 3'-X).

Figure 18:
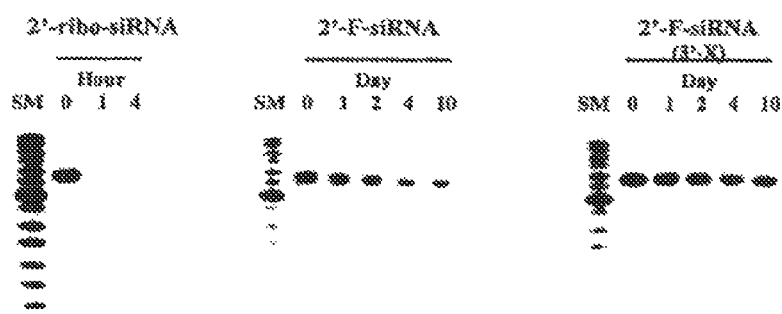

FIG. 18 shows that siRNA stability can be dramatically increased by fluorination within 2'-sugar.

Figure 19:
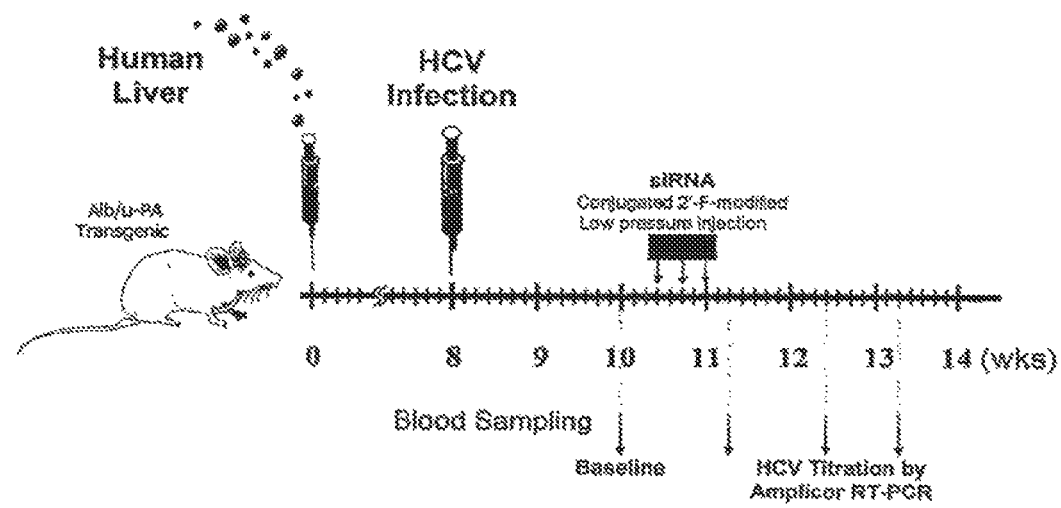

FIG. 19 shows evaluation of siRNA in vivo.

Figure 20:
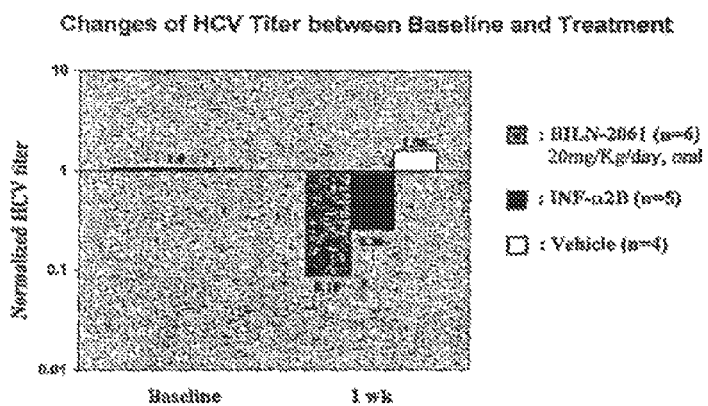

FIG. 20 shows conjugated 2'-F-siRNA is efficacious in chimeric mice by low pressure W injection.

Figure 21:
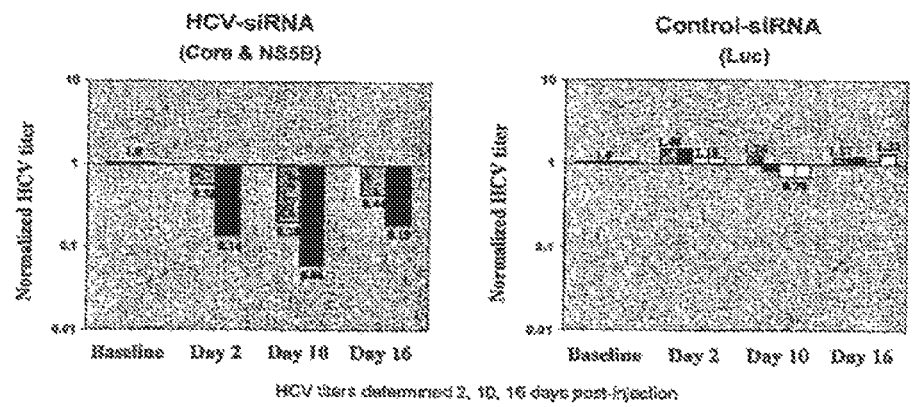

FIG. 21 shows conjugated 2'-F-siRNA given subcutaneously is partically effective in chimeric mice.

DETAILED DESCRIPTION OF THE INVENTION

The present invention provides dsRNA molecules that are about 10 to about 30 nucleotides long, and that mediate RNA interference in target cells. Preferably, the inventive molecules are chemically modified to confer increased stability against nuclease degradation, but retain the ability to bind to target nucleic acids.

As used herein, "RNA interference" (RNAi) refers to sequence-specific or gene specific suppression of gene expression (protein synthesis) that is mediated by siRNA, without generalized suppression of protein synthesis. While the invention is not limited to a particular theory or mode of action, RNAi may involve degradation of messenger RNA (mRNA) by an RNA-induced silencing complex (RISC), preventing translation of the transcribed mRNA. Alternatively, it may involve methylation of genomic DNA, which shunts transcription of a gene. The suppression of gene expression caused by RNAi may be transient or it may be more stable, even permanent.

"Gene suppression", "targeted suppression", "sequence-specific suppression", "targeted RNAi" and "sequence-specific RNAi" are used interchangeably herein. Furthermore, sequence-specific suppression, as used herein, is determined by separately assaying levels of the protein targeted for suppression in cells containing the siRNA (experimental cells) and in cells not containing the identical siRNA (control cells), then comparing the two values. Experimental and control cells should be derived from the same source and same animal. Also, control and experimental cells used in determining the level or quantity of gene suppression should be assayed under similar, if not identical, conditions.

RNA is a polymer of ribonucleotides, each containing the sugar ribose in association with a phosphate group and a nitrogenous base (typically, adenine, guanine, cytosine, or uracil). Like its cousin, DNA, RNA can form complementary hydrogen bonds. Therefore, RNA may be double-stranded (dsRNA), single-stranded (ssRNA) or double-stranded with a single-stranded overhang. Common types of RNA include messenger RNA (mRNA), transfer RNA (tRNA), ribosomal RNA (rRNA), short interfering RNA (siRNA), micro RNA (miRNA) and small hairpin RNA (shRNA), each of which plays a specific role in biological cells. As used herein, the term "RNA" includes all of these.

"Small interfering RNA" (siRNA) refers to double-stranded RNA molecules from about 10 to about 30 nucleotides long that are named for their ability to specifically interfere with protein expression. Preferably, siRNA molecules are 12-28 nucleotides long, more preferably 15-25 nucleotides long, still more preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27 28 or 29 nucleotides in length.

The length of one strand designates the length of an siRNA molecule. For instance, an siRNA that is described as 21 ribonucleotides long (a 21-mer) could comprise two opposite strands of RNA that anneal together for 19 contiguous base pairings. The two remaining ribonucleotides on each strand would form an "overhang." When an siRNA contains two strands of different lengths, the longer of the strands designates the length of the siRNA. For instance, a dsRNA containing one strand that is 21 nucleotides long and a second strand that is 20 nucleotides long, constitutes a 21-mer.

siRNAs that comprise an overhang are desirable. The overhang may be at the 5' or the 3' end of a strand. Preferably, it is at the 3' end of the RNA strand. The length of an overhang may vary, but preferably is about 1 to about 5 bases, and more preferably is about 2 nucleotides long. Preferably, the siRNA of the present invention will comprise a 3' overhang of about 2 to 4 bases. More preferably, the 3' overhang is 2 ribonucleotides long. Even more preferably, the 2 ribonucleotides comprising the 3' overhang are uridine (U).

siRNAs of the present invention are designed to interact with a target ribonucleotide sequence, meaning they complement a target sequence sufficiently to bind to the target sequence. Preferably the target ribonucleotide sequence derives from a disease producing agent or pathogen. More preferably, the target ribonucleotide sequence is in a virus genome of an RNA virus or a DNA virus. Even more preferably, the virus is selected from the group consisting of hepatitis C virus (HCV), hepatitis A virus, hepatitis B virus, hepatitis D virus, hepatitis E virus, Ebola virus, influenza virus, rotavirus, reovirus, retrovirus, poliovirus, human papilloma virus (HPV), metapneumovirus and coronavirus.

Figure 1:
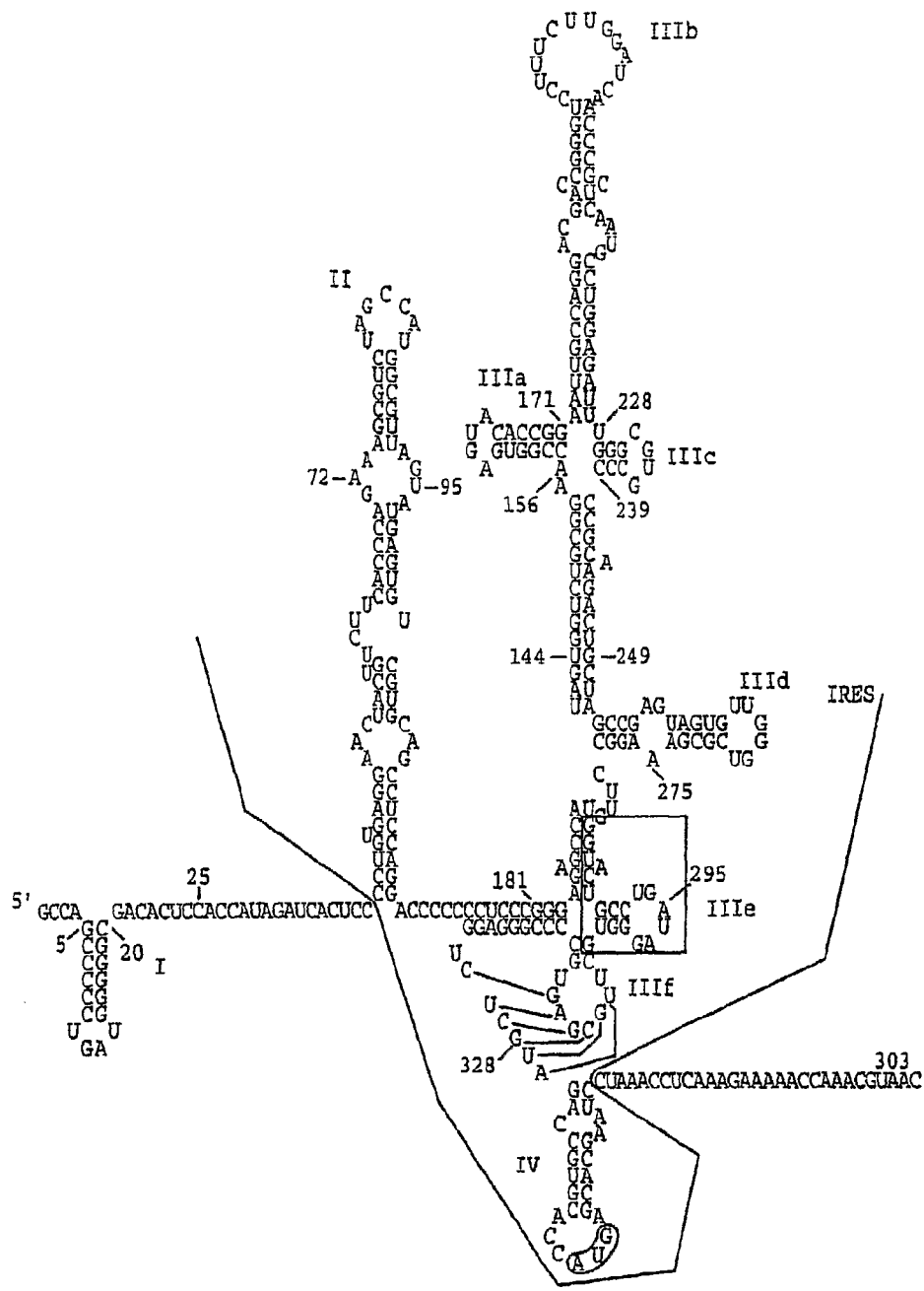
FIG. 1 depicts the sequence and secondary structure of the 5' UTR from the HCV genome. It also provides specific sequences of siRNAs for inducing RNAi toward HCV in hepatic cells.

Hepatitis C virus (HCV) is a highly preferred virus target. FIG. 1 and FIG. 2 disclose the nucleic acid sequences for several HCV-specific siRNA molecules. Among those shown, siRNA5, siRNAC1, siRNAC2, siRNA5B1, siRNA5B2, and siRNA5B4 have shown particularly good activity, and therefore are highly preferred. siRNAs at least 80%, 90%, or 95%, identical to these highly preferred siRNAs also constitute part of the invention.

Another preferred virus target is the coronavirus, which is associated with upper respiratory infections in humans and recently has been linked with SARS (severe acute respiratory syndrome). Coronavirus has the largest known RNA virus genome, 32 kilobases long, and its genome is composed of positively stranded RNA. (See FIG. 5) Each coronavirus mRNA has a 5'-end leader sequence of 60 to 80 nucleotides that is identical to the 5'-UTR of genomic RNA approximately 200 nucleotides long. (See FIG. 6) These sequences are highly conserved, and therefore, provide an excellent source of target sequences for which siRNAs. See *Fundamental Virology*, 3$^{rd}$ Ed., Chapter 18, p. 541-560 (Eds. Fields, Knipe and Howley), Lippincott-Raven (1995). In one embodiment, the entire leader sequence (nucleotides 1-72) is targeted. In another embodiment, one or more sections of the leader sequence is targeted. In a preferred embodiment, nucleotides 64-72 (TAAACGAAC) of the leader sequence are targeted. siRNA targeted to the coronavirus may be modified or unmodified.

In one embodiment, the invention provides an siRNA molecule comprising a ribonucleotide sequence at least 80% identical to a ribonucleotide sequence from a target agent or virus. Preferably, the siRNA molecule is at least 90%, 95%, 96%, 97%, 98%, 99% or 100% identical to the ribonucleotide sequence of the target agent or virus. The target can be the entire viral genome, a primary transcript, an open reading frame, or any portion of these. Most preferably, an siRNA will be 100% identical to the nucleotide sequence of a target agent or virus. However, siRNA molecules with insertions, deletions or single point mutations relative to a target may also be effective. Tools to assist siRNA design are readily available to the public. For example, a computer-based siRNA design tool is available on the internet at www.dharmacon.com.

By way of example, a polynucleotide having a nucleotide sequence at least 95% "identical" to a reference nucleotide sequence means that the polynucleotide's sequence may include up to five point mutations per 100 nucleotides of the reference nucleotide sequence, or 1 point mutation per 20 nucleotides. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97% 98%, 99% or 100% identical to the ribonucleotide sequence of a target agent or virus can be determined conventionally using known computer programs such as the Bestfit program (Wisconsin Sequence Analysis Package, Version 8 for Unix, Genetics Computer Group, Madison, Wis.). Bestfit uses the local homology algorithm of Smith and Waterman (Advances in Applied Mathematics 2:482-489 (1981)) to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference ribonucleotide sequence and that gaps in homology of up to 5% of the total number of ribonucleotides in the reference sequence are allowed.

The present invention also includes siRNA molecules that have been chemically modified to confer increased stability against nuclease degradation, but retain the ability to bind to target nucleic acids that may be present in cells. In the case where a target RNA is virus-specific, the modified siRNAs are able to bind to the virus specific RNAs or DNAs, thereby inactivating the virus.

A modified siRNA of the present invention comprises a modified ribonucleotide, and is resistant to enzymatic degradation, such as RNase degradation, yet retains the ability to inhibit viral replication in a cell containing the specific viral target RNA or DNA sequences. The siRNA may be modified at any position of the molecule so long as the modified siRNA binds to a target sequence and is resistant to enzymatic degradation. Modifications in the siRNA may be in the nucleotide base, i.e., the purine or the pyrimidine, the ribose or the phosphate. Preferably, the modification occurs at the 2' position of at least one ribose in an siRNA.

More specifically, the siRNA is modified in at least one pyrimidine, at least one purine or a combination thereof. However, generally all pyrimidines (cytosine or uracil), or all purines (adenosine or guanine) or a combination of all pyrimidines and all purines of the siRNA are modified. More preferably, the pyrimidines are modified, and these pyrimidines are cytosine, a derivative of cytosine, uracil, a derivative of uracil or a combination thereof. Ribonucleotides on either one or both strands of the siRNA may be modified.

Ribonucleotides containing pyrimidine bases found in RNA (cytidine and uridine) can be chemically modified by adding any molecule that inhibits RNA degradation or breakdown of the base, the ribose or the phosphates. As previously noted, the 2' position of ribose is a preferred site for modification. 2' modified siRNAs have a longer serum half-life and are resistant to degradation, relative to unmodified siRNAs or single-stranded RNAs, such as antisense or ribozyme. 2'-modified pyrimidine ribonucleotides can be formed by a number of different methods known in the art.

A preferable chemical modification is the addition of a molecule from the halide chemical group to a ribonucleotide of siRNA. Within the halides, fluorine is a preferred molecule. Besides fluoro-, other chemical moieties such as methyl-, methoxyethyl- and propyl- may be added as modifications. The most preferred modification, though, is fluoro-modification, such as a 2'-fluoro-modification or a 2',2'-fluoro-modification.

Thus, in a preferred embodiment of the invention, siRNA is modified by the addition of a fluorine molecule to the 2' carbon of a pyrimidine ribonucleotide. The siRNA may be fluorinated completely or partially. For example, only the cytosine ribonucleotides may be fluorinated. Alternatively, only the uracil ribonucleotides may be fluorinated. In a preferred embodiment, both uracil and cytosine are fluorinated. Only one strand, either sense or antisense, of siRNA may to be fluorinated. Even partial 2' fluorination of siRNA gives protection against nucleolytic degradation. Importantly, 2' fluorinated siRNA is not toxic to cells, an unexpected result given that fluorine chemistry usually is toxic to living organisms.

In addition, modified siRNAs of the present invention may contain chemical modifications that inhibit viral RNA polymerases. For example, siRNAs may comprise one or more nucleosides that inhibit viral RNA-dependent RNA polymerases. Examples of such nucleosides and other chemical modifications exist in WO 02/057425, WO 02/057287, WO 02/18404, WO 02/100415, WO 02/32920, WO 01/90121, U.S. Pat. No. 6,063,628 and US published application No. 2002/0019363.

siRNA can be prepared in a number of ways, such as by chemical synthesis, T7 polymerase transcription, or by treating long double stranded RNA (dsRNA) prepared by one of the two previous methods with Dicer enzyme. Dicer enzyme creates mixed populations of dsRNA from about 21 to about 23 base pairs in length from dsRNA that is about 500 base pairs to about 1000 base pairs in size. Unexpectedly, Dicer can effectively cleave modified strands of dsRNA, such as 2' fluoro-modified dsRNA. Before development of this method, it was previously thought that Dicer would not be able to cleave modified siRNA. The Dicer method of preparing siRNAs can be performed using a Dicer siRNA Generation Kit available from Gene Therapy Systems (San Diego, Calif.).

The invention particularly includes a method of making a modified siRNA that targets a nucleic acid sequence in a virus, comprising (a) preparing a modified-double stranded RNA (dsRNA) fragment containing at least one modified ribonucleotide in at least one strand, and (b) cleaving the modified-dsRNA fragments with recombinant human Dicer, resulting in more than one modified siRNA. The method may further comprise (c) isolating the modified siRNAs.

In the methods for making siRNA, a dsRNA fragment can be prepared by chemical synthesis or in vitro translation. In one embodiment, the modified siRNA is a 2' modified siRNA in which the modification is at the 2' position of at least one ribonucleotide of said siRNA. The modification is selected from the group consisting of fluoro-, methyl-, methoxyethyl and propyl-modification. Preferably the fluoro-modification is a 2'-fluoro-modification or a 2',2'-fluoro-modification. The pyrimidines, the purines or a combination thereof of the siRNA are modified. More preferably, the pyrimidines are modified, such as cytosine, a derivative of cytosine, uracil, a derivative of uracil or a combination thereof. One or both strands of the siRNA may contain one or more modified ribonucleotide.

The invention further provides a method of inactivating a target agent or virus in a patient by administering to the patient a dsRNA in an effective amount to inactivate the targeted agent or virus. Preferably the dsRNA is modified as described above. RNA interference toward a targeted DNA segment in a cell can be achieved by administering a double-stranded RNA molecule to the cells, wherein the ribonucleotide sequence of the double-stranded RNA molecule corresponds to the ribonucleotide sequence of the targeted DNA segment. Preferably, the dsRNA used to induce targeted RNAi is siRNA.

As used herein "targeted DNA segment" is used to mean a DNA sequence encoding, in whole or in part, an mRNA for a targeted protein, including introns or exons, where suppression is desired. DNA segment can also mean a DNA sequence that normally regulates expression of the targeted protein, including but not limited to the promoter of the targeted protein. Furthermore, the DNA segment may or may not be a part of the cell's genome or it may be extrachromosomal, such as plasmid DNA.

The present invention is particularly directed to a method of inactivating a virus in a patient by administering to the patient an siRNA, preferably a modified siRNA, in an effective amount to inactivate the virus. The siRNA is preferably about 10 to about 30 ribonucleotides in length, more preferably 12-28 ribonucleotides, more preferably 15-25 ribonucleotides, even more preferably 19-23 ribonucleotides and most preferably 21-23 ribonucleotides.

Also, the method of inactivating a virus preferably utilizes an siRNA that is modified at the 2' position of at least one ribonucleotide of said siRNA. The siRNA may be modified with chemical groups selected from the group consisting of fluoro-, methyl-, methoxyethyl- and propyl-. Fluoro-modification is most preferred, and either a 2'-fluoro-modification or a 2',2'-fluoro-modification is useful in the method. The modification may be at a pyrimidine, a purine or a combination thereof of the siRNA. More preferably the pyrimidines are modified, such as cytosine, a derivative of cytosine, uracil, a derivative of uracil or a combination thereof. In one embodiment, one strand of the siRNA contains at least one modified ribonucleotide, while in another embodiment, both strands of the siRNA contain at least one modified ribonucleotide.

siRNAs useful in treatment methods may also be modified by the attachment of at least one, but preferably more than one, receptor-binding ligand(s) to the siRNA. Such ligands are useful to direct delivery of siRNA to a target virus in a body system, organ, tissue or cells of a patient, such as the liver, gastrointestinal tract, respiratory tract, the cervix or the skin.

In preferred embodiments, receptor-binding ligands are attached to either a 5'-end or a 3'-end of an siRNA molecule. Receptor-binding ligands may be attached to one or more siRNA ends, including any combination of 5'- and 3'-ends. Thus, when receptor binding ligands are attached only to the ends of an siRNA molecule, anywhere between 1 and 4 such ligands may be attached.

The selection of an appropriate ligand for targeting siRNAs to viruses in particular body systems, organs, tissues or cells is considered to be within the ordinary skill of the art. For example, to target an siRNA to hepatocytes, cholesterol may be attached at one or more ends, including any combination of 5'- and 3'-ends, of an siRNA molecule. The resultant cholesterol-siRNA is delivered to hepatocytes in the liver, thereby providing a means to deliver siRNAs to this targeted location. Other ligands useful for targeting siRNAs to the liver include HBV surface antigen and low-density lipoprotein (LDL).

As another example, siRNA molecules that target Human Immunodeficiency virus type 1 (HIV-1) can be delivered to T lymphocytes where the target nucleic acids are located (Song, E. et al., *J. of Virology*, 77(13): 7174-7181 (2003)). This delivery can be accomplished by attaching, at the 3'-end or 5'-end of siRNA molecules, HIV-1 surface antigen capable of binding to the CD4 surface protein located on T-cells (Kilby, M. et al., *New England J. of Medicine*, 348(22): 2228-38 (2003)).

Similarly, siRNA molecules that target Influenza A virus can be delivered to epithelial cells of the respiratory tract where the target nucleic acids are located (Ge, Q. et al., *Proc. Natl. Acad. of Sciences*, 100(5): 2718-2723 (2002)). This delivery can be accomplished by attaching, at the 3'-end or 5'-end of siRNA molecules, the Influenza virus surface antigen, which is capable of binding to the sialic acid residues located on the surface of the epithelial cells (Ohuchi, M., et al., *J. of Virology*, 76(24): 12405-12413 (2002); Glick, G. et al., *J. of Biol. Chem.*, 266 (35): 23660-23669 (1991)).

Also, siRNA molecules that target respiratory syncitial virus (RSV) can be delivered to epithelial cells of the respiratory tract where the target nucleic acids are located (Bitko, V. et al., *BMC Microbiology*, 1:34 (2001)). This delivery can be accomplished by attaching, at the 3'-end or 5'-end of siRNA molecules, RSV surface antigen (Malhotra, R. et al., *Microbes and Infection*, 5: 123-133 (2003)).

As still another example, siRNAs that target Human Papillomavirus (HPV) can be delivered to basal epithelial cells where the target nucleic acids are located (Hall, A. et al., *J. of Virology*, 77(10): 6066-6069 (2003)). This delivery can be accomplished by attaching, at the 3'-end or 5'-end of siRNA molecules, HPV surface antigen capable of binding to heparin sulfate proteoglycans located on the surface of basal epithelial cells (Bousarghin L. et al., *J. of Virology*, 77(6): 3846-3850 (2002)).

Further, siRNAs that target Poliovirus (PV) can be delivered to cells of the nervous system where the target nucleic acids are located (Gitlin, L. et al., *Nature*, 418: 430-434 (2002)). This delivery can be accomplished by attaching, at the 3'-end or 5'-end of siRNA molecules, PV surface antigen capable of binding to the CD155 receptor located on the surface of neurons (He, Y. et al., *Proc. Natl. Acad. of Sciences*, 97 (1): 79-84 (2000)).

As noted, the methods of treatment are intended to target disease-causing agents or pathogens, and more particularly viruses, which can be either RNA viruses or DNA viruses. Preferred viruses are selected from the group consisting of hepatitis C virus (HCV), hepatitis A virus, hepatitis B virus, hepatitis D virus, hepatitis E virus, Ebola virus, influenza virus, rotavirus, reovirus, retrovirus, poliovirus, human papilloma virus (HPV), metapneumovirus and coronavirus. More preferably the target virus is hepatitis C virus or a coronavirus.

In one aspect, the method utilizes an siRNA prepared by (a) identifying a target ribonucleotide sequence in a virus genome for designing a small interfering RNA (siRNA) and (b) producing a siRNA that has been modified to contain at least one modified ribonucleotide. Preferably, the siRNA comprises a double-stranded RNA molecule with a first strand ribonucleotide sequence corresponding to a ribonucleotide sequence corresponding to a target ribonucleotide sequence in the virus, and a second strand comprising a ribonucleotide sequence complementary to the target ribonucleotide sequence. The first and second strands should be separate complementary strands that hybridize to each other to form a double-stranded RNA molecule. Moreover, one or both of the strands should comprise at least one modified ribonucleotide.

In preferred embodiments of the invention, the siRNA targets a ribonucleotide sequence in the hepatitis C virus genome. The target ribonucleotide sequence comprises a conserved ribonucleotide sequence necessary for HCV replication, and the conserved ribonucleotide sequence is selected from the group consisting of 5'-untranslated region (5'-UTR), 3'-untranslated region (3'-UTR), core, and NS3 helicase. Highly preferred siRNA molecules comprise a sequence at least 80% identical to those of siRNA5, siRNAC1, siRNAC2, siRNA5B1, siRNA5B2, or siRNA5B4. The siRNAs may be unmodified, or modified as described above.

Methods of inhibiting the replication of HCV in cells positive for HCV should not be toxic to the cells, or cause apoptosis in the treated cells. Preferably, the inhibition of HCV replication is specifically tailored to affect only HCV replication in the cells, such that normal growth, division or metabolism is not affected. Cells in which HCV has been shown to replicate include, but are not limited to hepatic cells, B cell lymphocytes and T cell lymphocytes. Preferably, a method of inhibiting the replication of HCV is performed in hepatic cells.

According to the invention, “hepatic cells” can be from any animal source. Further, the hepatic cells may be in cell culture, or part of a tissue, or an organ, in part or in whole. The phrase hepatic cells is meant to include any cell constituting a normal, abnormal or diseased liver cell. Examples of hepatic cells include, but are not limited to, Kupffer cells, hepatocytes and cells comprising a hepatocellular carcinoma. “Hepatic cells” is not meant to include cells that make up discrete structures within the liver, such as endothelial cells lining blood vessels. A tissue or organ containing the hepatic cells may be within a subject or may be biopsied or removed from the animal. Additionally, the tissue may be “fresh” in that the tissue would be recently removed from a subject, without any preservation steps between the excision and the methods of the current invention. Prior to application of the methods of the current invention, the tissue may also have been preserved by such standard tissue preparation techniques including, but not limited to, freezing, quick freezing, paraffin embedding and tissue fixation. Furthermore, the tissue may also be a xenograft or a syngraft on or in another host animal. As used herein, the terms animal and subject are used interchangeably.

According to the invention, “hepatitis C virus,” or “HCV,” takes its ordinary meaning in the art as of the date of invention. The hepatitis C virus is an RNA virus of the Flaviviridae family. For example as used herein, HCV includes, but is not limited to genotypes 1-11 (using the most common genotyping system), with these genotypes being broken down into sub-types, some of which include but are not limited to 1a, 1b, 1c, 2a, 2b, 2c, 3a, 3b, 4a, 4b, 4c, 4d, 4e, 5a, 6a, 7a, 7b, 8a, 8b, 9a, 10a and 11a. Further, isolates from individuals consist of closely related yet heterogeneous populations of viral genomes, sometimes referred to as quasispecies.

Pestivirus is yet another target of the present invention. As used herein, “pestivirus” takes its ordinary meaning in the art as of the date of invention. The pestivirus belongs to the family Flaviviridae. Pestivirus is widespread throughout the Australian cattle population. It is believed that about 70% of herds are actively infected with pestivirus. Infection of susceptible animals can cause a variety of diseases—some not apparent until well after the initial spread of the virus into a herd. Pestivirus is a genus of viruses that includes hog cholera virus, bovine viral diarrhea virus (BVDV) and border disease virus (BDV) or hairy-shaker disease virus.

siRNA may be administered to a patient by intravenous injection, subcutaneous injection, oral delivery, liposome delivery or intranasal delivery. The siRNA may then accumulate in a target body system, organ, tissue or cell type of the patient.

The present invention also provides a method of inhibiting the replication of a virus in mammalian cells, comprising transfecting cells harboring the virus with a vector that directs the expression of virus-specific siRNA. In one embodiment, the invention provides a method of inhibiting the replication of hepatitis C virus (HCV) in cells positive for HCV, comprising transfecting HCV-positive cells with a vector that directs the expression of an HCV-specific siRNA. The cells may be evaluated to determine if a marker in the cells has been inhibited by the siRNA.

Thus, the invention also provides vectors and host cells comprising a nucleic acid segment encoding the described siRNAs.

Vectors of the present invention may be employed for producing siRNAs by recombinant techniques. Thus, for example, a DNA segment encoding an siRNA may be included in any one of a variety of expression vectors for expressing any DNA sequence. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in a desired host.

The appropriate DNA segment may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA segment in the expression vector is operatively linked to an appropriate expression control sequence(s) (promoter) to direct siRNA synthesis. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter. Preferably the promoters of the present invention are from the type III class of RNA polymerase III promoters. More preferably, the promoters are selected from the group consisting of the U6 and H1 promoters. The U6 and H1 promoters are both members of the type III class of RNA polymerase III promoters. The promoters of the present invention may also be inducible, in that expression may be turned "on" or "off." For example, a tetracycline-regulatable system employing the U6 promoter may be used to control the production of siRNA. The expression vector may or may not contain a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or tetracycline or ampicillin resistance.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

In one embodiment, the invention provides a vector, wherein the DNA segment encoding the sense strand of the RNA polynucleotide is operably linked to a first promoter and where the DNA segment encoding the antisense (opposite) strand of the RNA polynucleotide molecule of is operably linked to a second promoter. In other words, each strand of the RNA polynucleotide is independently expressed. Furthermore, the promoter driving expression of each strand can be identical or each one may be different from the other promoter.

In another embodiment, the vector of the current invention may comprise opposing promoters. For example, the vector may comprise two U6 promoters on either side of the DNA segment encoding the sense strand of the RNA polynucleotide and placed in opposing orientations, with or without a transcription terminator placed between the two opposing promoters. The U6 opposing promoter construct is similar to the T7 opposing promoter construct as described in Wang, Z. et al., J. Biol. Chem. 275: 40174-40179 (2000). See Miyagishi, M. and Taira, K., Nature Biotech. 20: 497-500 (2002).

In another embodiment, the DNA segments encoding both strands of the RNA polynucleotide are under the control of a single promoter. In one embodiment, the DNA segments encoding each strand are arranged on the vector with a "loop" region interspersed between the two DNA segments, where transcription f the DNA segments and loop region creates one RNA transcript. The single transcript will, in turn, anneal to itself creating a "hairpin" RNA structure capable of inducing RNAi. The "loop" of the hairpin structure is preferably from about 4 to about 6 nucleotides in length. More preferably, the loop is 4 nucleotides in length.

The vector containing the appropriate DNA sequence as described herein, as well as an appropriate promoter or control sequence, may be employed to transform an appropriate host to permit the host to express the siRNA. Appropriate cloning and expression vectors for use with prokaryotic and eukaryotic hosts are described by Sambrook, et al., Molecular Cloning: A Laboratory Manual, Second Edition, Cold Spring Harbor, N.Y. (1989), the disclosure of which is hereby incorporated by reference.

Host cells are genetically engineered (transduced or transformed or transfected) with the vectors of this invention which may be, for example, cloning vectors or expression vectors. The vectors may be, for example, in the form of a plasmid, a viral particle, a phage, etc. The engineered host cells may be cultured in conventional nutrient media modified as appropriate for activating promoters, selecting transformants. The culture conditions, such as temperature, pH and the like, are those previously used with the host cell selected for expression, and will be apparent to the ordinarily skilled artisan.

In a further embodiment, the present invention relates to host cells containing the above-described constructs. A host cell may be a higher eukaryotic cell, such as a mammalian cell, or a lower eukaryotic cell, such as a yeast cell, or the host cell may be a prokaryotic cell, such as a bacterial cell. Preferably, host cells are mammalian cells. More preferably, host cells are hepatic cells. Introduction of a construct into host cells can be effected by calcium phosphate transfection, DEAE-Dextran mediated transfection, or electroporation (Davis, L., et al., Basic Methods in Molecular Biology (1986)).

The term patient, as used herein, refers to an animal, preferably a mammal. More preferably the patient can be a primate, including non-human and humans. The terms subject and patient are used interchangeably herein.

The treatments envisioned by the current invention can be used for subjects with a pre-existing viral infection, or for subjects pre-disposed to an infection. Additionally, the methods of the current invention can be used to correct or compensate for cellular or physiological abnormalities involved in conferring susceptibility to viral infections in patients, and/or to alleviate symptoms of a viral infections in patients, or as a preventative measure in patients.

The method of treating a patient having a viral infection involves administration of compositions to the subjects. As used herein, composition can mean a pure compound, agent or substance or a mixture of two or more compounds, agents or substances. As used herein, the term agent, substance or compound is intended to mean a protein, nucleic acid, carbohydrate, lipid, polymer or a small molecule, such as a drug.

In one embodiment of the current invention, the composition administered to the subject is a pharmaceutical composition. Further, the pharmaceutical composition can be administered orally, nasally, parenterally, intrasystemically, intraperitoneally, topically (as by drops or transdermal patch), bucally, or as an oral or nasal spray. Intranasal delivery of a virus that causes upper respiratory diseases, such as the coronavirus or the metapneumovirus, would be a particularly advantageous delivery mode. The term "parenteral," as used herein, refers to modes of administration that include intravenous, intramuscular, intraperitoneal, intrasternal, subcutaneous and intraarticular injection and infusion. The pharmaceutical compositions as contemplated by the current invention may also include a pharmaceutically acceptable carrier.

"Pharmaceutically acceptable carrier" includes, but is not limited to, a non-toxic solid, semisolid or liquid filler, diluent, encapsulating material or formulation auxiliary of any type, such as liposomes.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention can also contain adjuvants such as, but not limited to, preservatives, wetting agents, emulsifying agents, and dispersing agents. Prevention of the action of microorganisms can be ensured by the inclusion of various antibacterial and antifungal agents, for example, paraben, chlorobutanol, phenol, sorb acid, and the like. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

In some cases, to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Alternatively, the composition can be pressurized and contain a compressed gas, such as nitrogen or a liquefied gas propellant. The liquefied propellant medium and indeed the total composition is preferably such that the active ingredients do not dissolve therein to any substantial extent. The pressurized composition can also contain a surface active agent. The surface active agent can be a liquid or solid nonionic surface active agent or can be a solid anionic surface active agent. It is preferred to use the solid anionic surface active agent in the form of a sodium salt.

The compositions of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 et seq (1976)).

One of ordinary skill in the art will appreciate that effective amounts of the agents of the invention can be determined empirically and can be employed in pure form or, where such forms exist, in pharmaceutically acceptable salt, ester or prodrug form. A "therapeutically effective" amount of the inventive compositions can be determined by prevention or amelioration of adverse conditions or symptoms of diseases, injuries or disorders being treated. The agents can be administered to a subject, in need of treatment of viral infection, as pharmaceutical compositions in combination with one or more pharmaceutically acceptable excipients. It will be understood that, when administered to a human patient, the total daily usage of the agents or composition of the present invention will be decided by the attending physician within the scope of sound medical judgement. The specific therapeutically effective dose level for any particular patient will depend upon a variety of factors: the type and degree of the cellular or physiological response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

Dosing also can be arranged in a patient specific manner to provide a predetermined concentration of the agents in the blood, as determined by techniques accepted and routine in the art. Thus patient dosaging can be adjusted to achieve regular on-going blood levels, as measured by HPLC, on the order of from 50 to 1000 ng/ml.

Various medications can lower blood cholesterol levels. These medications or drugs include e.g., statins, resins and nicotinic acid (niacin), gemfibrozil and clofibrate. Clofibrate (Atromid-S) raises the HDL cholesterol levels and lowers triglyceride levels. Gemfibrozil (Lopid) lowers blood fats and raises HDL cholesterol levels. Nicotinic Acid works in the liver and is used to lower triglycerides and LDL cholesterol, and raise HDL ("good") cholesterol. Resins promote increased disposal of cholesterol. Medications in this class include: Cholestryamine (Questran, Prevalite, Lo-Cholest); Colestipol (Colestid); and Coleseveiam (WelChol).

Statin drugs are very effective for lowering LDL ("bad") cholesterol levels, have few immediate short-term side effects and are a preferred cholesterol lowering drug for use in the methods of the present invention. The statins include: Atorvastatin (Lipitor); Fluvastatin (Lescol); Lovastatin (Mevacor); Pravastatin (Pravachol); Rosuvastatin Calcium (Crestor); and Simvastatin (Zocor). (See also "Cholesterol lowering with statin drugs, risk of stroke, and total mortality. An overview of randomized trials"; Hebert P R, Gaziano J M, Chan K S, Hennekens C H. JAMA 1997 Nov. 26; 278(20):1660-1.

HMG-CoA (3-hydroxy-3-methylglutaryl-coenzyme A) reductase (HMGR) catalyzes the committed step in cholesterol biosynthesis. Statins are HMGR inhibitors with inhibition constant values in the nanomolar range that effectively lower serum cholesterol levels and are widely prescribed in the treatment of hypercholesterolemia. Statin drugs increase the expression of LDL receptors on the surface of liver hepatocytes. As a consequence of the increase in LDL receptor expression, the level of cholesterol is lowered in plasma. Thus, by administering a statin drug, the level of competing cholesterol in plasma is reduced and the level of LDL receptors for binding cholesterol-siRNA in the liver are increased. The invention thus provides a method for increased uptake of cholesterol labeled siRNA wherein the siRNA is administered in conjunction with a statin whereby the level of competing cholesterol in the serum is reduced, allowing for more efficient uptake of cholesterol labeled siRNA by hepatocytes. The statin can be administered before, with or after the administration of the cholesterol-siRNA.

It will be readily apparent to one of ordinary skill in the relevant arts that other suitable modifications and adaptations to the methods and applications described herein can be made without departing from the scope of the invention or any embodiment thereof.

EXAMPLES

The examples demonstrate that siRNA, including modified siRNA, can effectively inhibit viral replication in mammalian cells. Moreover, the examples show that the inventive siRNAs promote HCV RNA degradation in human liver cells and establish that hepatocytes possess the necessary functional components of modified siRNA-induced silencing. The examples also demonstrate that siRNA technology can be used as a therapy to inhibit HCV replication in host cells. The inventors, by submitting the following examples, do not intend to limit the scope of the claimed invention.

Example 1

To test whether siRNA directed to the HCV genome confers intracellular immunity against this human pathogen, a recently developed HCV cell culture systems in human hepatoma cell line, Huh-7, was used. One of the cell lines, 5-2, harbors autonomously replicating subgenomic HCV RNA (Bartenschlager, J. Virol, 2001). The subgenomic replicon carries firefly luciferase gene, allowing a reporter function assay as a measure of HCV RNA replication (FIG. 5). Owing to cell culture adaptive mutations introduced into the genome (Bart), these 5-2 cells replicate HCV RNA at levels of up to $5\times10^4$ virus particles/cell.

Using T7 transcription, several 21-bp siRNA duplexes against different regions of the 5'-UTR of the HCV genome were made (FIG. 5). Briefly, 2 oligo double-stranded DNA molecules comprising the T7 promoter and the 5' UTR of HCV being oriented in either the sense direction or the antisense direction were generated. Each oligo DNA was then transcribed in vitro to produce (+) and (−) RNA and then treated with DNAase I to remove the DNA template. The two RNA strands were allowed to anneal at 37° C. overnight, generating dsRNA. After treating the dsRNA with RNAase T1 to remove unreacted ssRNA species, the dsRNA was purified for transfection.

Several other siRNA duplexes were designed, including GL2 and GL3, that were directed against the fruit fly and sea pansy luciferase genes, respectively. Using standard transfection techniques, the siRNAs were transfected into the 5-2 cells and luciferase activity was measured to determine the effect of the siRNAs on HCV replication. Luciferase activity was measured 48 hours after transfection. In cells where siRNA5 was transfected, there was reduced luciferase activity of up to 85%, in a dose responsive manner (FIG. 6). The inhibition of luciferase activity was not seen in cells that were transfected with irrelevant siRNA (SIN). The sequence of SIN was taken from sindbis virus transcription promoter (FIG. 1).

Example 2

The sequence specificity of the siRNA5 response was further tested using additional siRNA duplexes, GL2 and GL3. FIG. 1 shows that GL2 and GL3 differ from each other by 3-nucleotides. Luciferase activity was reduced by 90% in cells transfected with siRNA5 or GL2, but no significant reduction was seen in cells transfected with GL3 (FIG. 7). The luciferase assay was performed using a Luciferase assay system available from Promega Corp. (Madison, Wis.), according to the manufacturer's instructions.

Example 3

Whether or not siRNA5 was toxic to transfected cells also was tested. Toxicity was by measured using an ATPase activity assay. FIG. 8 shows that the siRNA5-induced reduction in HCV replication, as seen in FIG. 6, was not due to cellular toxicity which is attributed to non sequence-specific RNAi. ATPase levels were assayed using an ATPase assay kit from Promega (Madison, Wis.) according to the manufacturer's instructions.

Example 4

The full-length HCV replicon may possess the ability to adapt and suppress RNAi, thus replicating in spite of the presence of siRNA, as documented in Li, H, Science 296: 1319-1321 (2002). To determine the effects of siRNA5 on replication of full-length HCV RNA in Huh-7 cells, from the 21-5 cell line, harboring the selectable full-length HCV replicon, were treated with siRNA5. Levels of HCV RNA were measured by quantitative PCR using TaqMan☐ (F. Hoffman La-Roche, Switzerland). The results as seen in FIG. 9 show that siRNA-directed silencing reduced steady-state viral RNA production, even in the setting of an adapted HCV mutant, where RNA replication was very high. Results from both subgenomic and full-length HCV replicons suggest that none of the HCV proteins can suppress RNA interference.

Example 5

Figure 10:
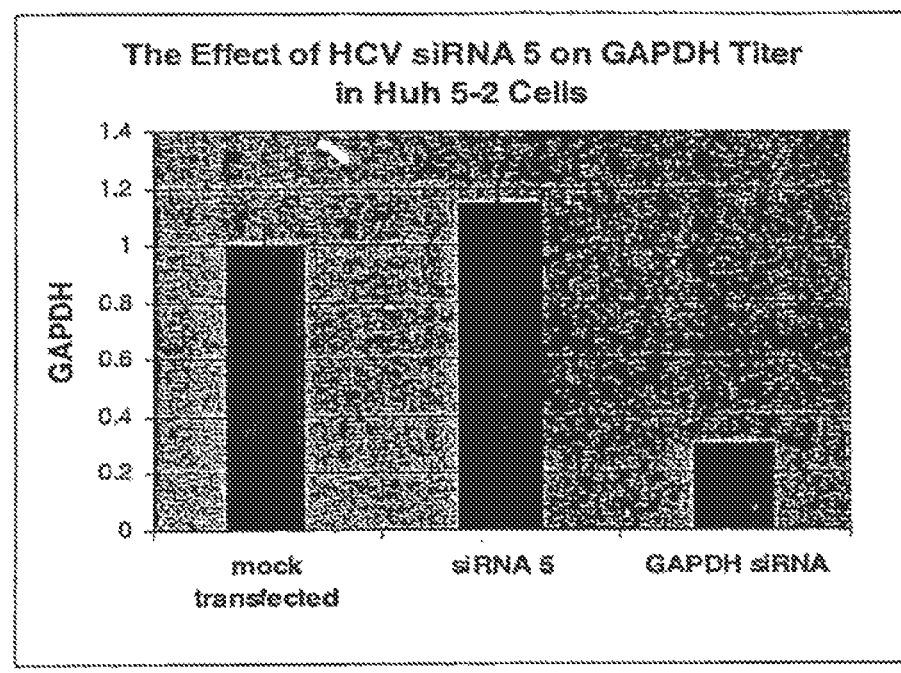
FIG. 10 demonstrates that siRNA5 does not affect the viability of Huh 5-2 cells. Specifically, mRNA encoding GAPDH, an enzyme essential to glycolysis was measured in Huh 5-2 cells transfected with siRNA5 or GAPDH-specific siRNA. The graph demonstrates that siRNA5 did not affect RNA levels of GAPDH. GAPDH was measured using a TaqMan☐ RNA kit (F. Hoffman La-Roche, Switzerland), according to the manufacturer's instructions. Values are normalized.

Whether or not siRNA5 was toxic to transfected cells also was tested. Specifically, mRNA encoding GAPDH, an enzyme essential in glycolysis, was measured in Huh 5-2 cells transfected with siRNA5, or siRNA specific towards the GAPDH sequence. FIG. 10 demonstrates that siRNA5 did not affect RNA levels of GAPDH. GAPDH was measured using a TaqMan☐ RNA kit (F. Hoffman La-Roche, Switzerland) according to the manufacturer's instructions.

Example 6

To test the effectiveness of siRNA5 on inhibiting the ability of HCV to replicate in an infected liver, portions of HCV-infected human liver are xenografted onto transgenic severe combined immunodeficient (SCID) mice according to methods well known to the skilled artisan.

Briefly, once the HCV-infected liver has supplanted the mouse liver, liposome-encapsulated siRNA5, or control liposomes are administered by intravenous injection to the mice through the tail vein, or another accessible vein. The mice are dosed one time a day for 3-10 days.

At the end of the dosing regimen the mice are sacrificed and blood collected and the livers removed. The liver is divided into portions such that a portion is frozen using liquid nitrogen, a portion is fixed for paraffin embedding, and a portion is fixed for sectioning onto slides.

Using the appropriate allotment, HCV RNA is quantified using the TaqMan☐ RNA assay kit previously utilized herein to determine the levels of HCV RNA in the liver cells. Further, anti-HCV antibody titers can be measured in the collected blood samples, along with serum ALT levels.

Example 7

To test the effectiveness of siRNA5 on inhibiting the ability of HCV to infect a healthy liver, portions of normal human liver are xenografted onto transgenic severe combined immunodeficient (SCID) mice according to methods well known to the skilled artisan.

Briefly, once the healthy liver has supplanted the mouse liver, liposome-encapsulated siRNA5, or control liposomes are administered by intravenous injection to the mice through the tail vein, or another accessible vein. The mice are dosed one time a day for 3-10 days. After the pre-dosing regimen, active HCV is then injected intravenously, or via hepatic injection, into the mice.

At about 6, 12, 18, 24 hours, and periodically up to about 5 days after the mice are infected with HCV, the mice are sacrificed and blood collected and the livers removed. The liver is divided into portions such that a portion is frozen using liquid nitrogen, a portion is fixed for paraffin embedding, and a portion is fixed for sectioning onto slides.

Using the appropriate allotment, HCV RNA is quantified using the TaqMan☐ RNA assay kit previously utilized herein to determine the levels of HCV RNA in the liver cells. Further, anti-HCV antibody titers can be measured in the collected blood samples, along with serum ALT levels.

Example 8

Modified siRNA can be prepared by chemical synthesis. In one embodiment, each C and U within a siRNA duplex, e.g. GL2, can be substituted with 2'-F-U and 2'F-C. To produce siRNA with 3'-end overhangs comprising 2'-F-U and 2'F-C, a universal support can be used. By selectively cleaving the oligo from the support, a practitioner can ensure that residues of the overhangs comprise modified nucleotides. Alternatively, the nucleotides comprising the 3'-end overhang can be unmodified dTdT.

2'-F RNA oligonucleotides can be synthesized on an Applied Biosystems 8909 or 8905 DNA/RNA synthesizer using the standard 1 μmol beta-cyanoethyl phosphoramidite RNA chemistry protocol. The RNA phosphoramidite monomers and columns of Pac-A, 2'-F-Ac-C, iPr-Pac-G, 2'-F-U, and U-RNA CPG can be obtained from Glen Research (Sterling, Va.). (See catalog nos. 10-3000-05, 10-3415-02, 10-3021-05, 10-3430-02, and 20-3430-41E, respectively.) Glen Research's Sulfurizing Reagent (catalog no. 40-4036-10) can be used as an oxidant to obtain a single phosphorothioate backbone between the 3' CPG and a subsequent base. To attain the coupling, the oxidizing step of the standard RNA 1 μmol protocol can be replaced with the standard thioate 1 μmol protocol. Cholesteryl-TEG phosphoramidite (Glen Research, catalog no. 10-1975-90) and cholesteryl-TEG CPG (Glen Research, catalog no. 20-2975-41E) can be incorporated onto the 5' or 3' ends of one or more of the oligoribonucleotides. After synthesis, the 2'-F RNA's are cleaved and deprotected with 1:1 ammonium hydroxide/methylamine, and the silyl groups are removed with triethylamine trihydrofluoride using standard protocols. See e.g. http://www.glenres.com/productfiles/technical/tb_rnadeprotection.pdf. The oligoribonucleotides are then desalted on Sephadex G25 columns (Pharmacia NAP 25, catalog no. 17-08252-02) with sterilized water and purified using standard gel electrophoresis protocols. Modified siRNAs also can be obtained from commercial vendors such as Dharmacon (Lafayette, Colo.).

Alternatively, modified siRNA can be prepared by transcription using the Durascribe☐ T7 Transcription Kit purchased from Epicentre Technologies (Madison, Wis.).

The modified siRNAs (dsRNAs) made by these methods contain phosphodiester linked oligonucleotides. Standard methods for making modified single-stranded RNAs, such as antisense molecules, are useful for making modified siRNAs, as modified single-stranded RNAs can be annealed together to form double stranded RNAs. Such standard methods include, but are not limited to, those described in Chiang et al., *J. Biol. Chem.* 266, 18162-18171 (1991); Baker et al., *J. Biol. Chem.* 272, 11994-12000 (1997); Kawasaki et al., *J. Med. Chem.* 36, 831-841 (1993); Monia et al., *J. Biol. Chem.* 268, 14514-14522 (1993).

Example 9

To test whether siRNA directed to the HCV genome confers intracellular immunity against this human pathogen, a recently developed HCV cell culture systems in human hepatoma cell line, Huh-7, was used. One of the cell lines, 5-2, harbors autonomously replicating subgenomic HCV RNA (Bartenschlager, J. Virol, 2001). The subgenomic replicon carries firefly luciferase gene, allowing a reporter function assay as a measure of HCV RNA replication. Owing to cell culture adaptive mutations introduced into the genome, 5-2 cells replicate HCV RNA at levels of up to $5 \times 10^4$ virus particles/cell.

Using T7 transcription, several 21-bp siRNA duplexes against different regions of the 5'-UTR of the HCV genome were made. Briefly, two oligo double-stranded DNA molecules comprising the T7 promoter and the 5' UTR of HCV being oriented in either the sense direction or the antisense direction were generated. Each oligo DNA was then transcribed in vitro to produce (+) and (−) RNA and then treated with DNAase I to remove the DNA template. The two RNA strands were allowed to anneal at 37° C. overnight, generating dsRNA. After treating the dsRNA with RNAase T1 to remove the unreacted ssRNA species, the dsRNA was purified for transfection.

Two exemplary modified siRNAs are provided below (wherein the sense strand of both Chol-GL2 and GL2 is CGUACGCGGAAUACUUCGAUU, SEQ ID NO: 5, and antisense strand of both Chol-GL2 and GL2 is UCGAAGUAUUCCGCGUACGUU, SEQ ID NO: 6):

Each C and U within siRNA GL2, directed against the fruit fly luciferase gene, was substituted with 2'-F-U and 2'F-C. The modified siRNAs were transfected into the 5-2 cells using standard liposome transfection techniques. Specifically, the modified siRNAs were incubated for 4 hrs at 37° C. in a 250 μl cell suspension containing 0.5 μl of Oligofectamine (Invitrogen, Carlsbad, Calif.), for 20 hrs in 375 μl serum containing culture medium, and for 24 hrs at 37° C. in fresh medium without the liposome-siRNA complex. Luciferase activity was measured 48 hours after transfection to determine the effect of the modified siRNAs on HCV replication.

Figure 11:
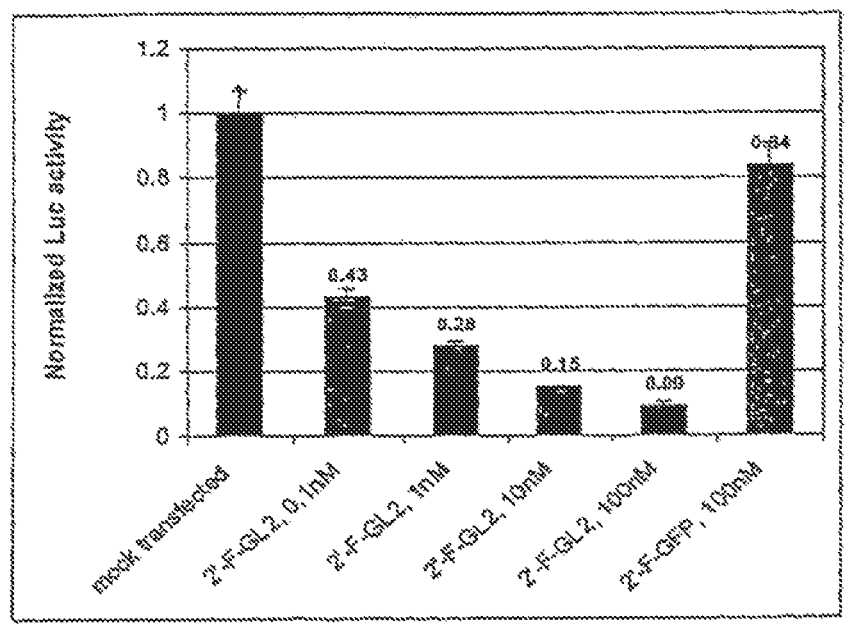
FIG. 11 depicts a dose response of normalized luciferase activity in Huh 7 cells containing a subgenomic HCV replicon (5-2 line) that were administered different concentrations of 2'-fluoro-siRNA (2'-F-GL2), which targets the fruit fly luciferase gene. Luciferase activity, which was measured at 2 days post-transfection, fell with increasing doses of siRNA. The luciferase assay was performed using a Firefly Luciferase kit (Promega Corp., Madison, Wis.), according to the manufacturer's instructions.

FIG. 11 shows that GL2 reduced the luciferase activity at increasing concentrations. Luciferase activity was reduced by 90% in cells transfected with 2'-F-GL2, but no significant reduction was seen in mocked transfected cells or with a control (2'-F-GFP=green fluorescent protein). The luciferase assay was carried out using a Luciferase assay system available from Promega Corp. (Madison, Wis.), according to the manufacturer's instructions.

Figure 12:
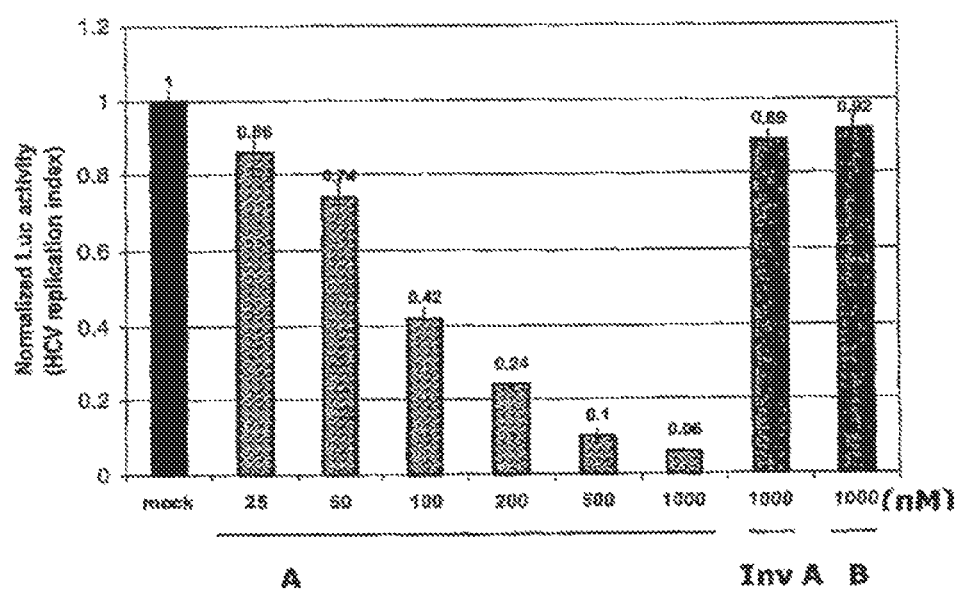
FIG. 12 demonstrates an inhibition of luciferase activity in 5-2 cells using the siRNA Chol-GL2 in the absence of liposomes.

The siRNA Chol-GL2 comprises a cholesteryl group on one of the 5' ends. 5-2 cells were incubated with various concentrations of Chol-GL2 in the absence of liposomes. Cells were harvested 48 hours after incubation and assayed for luciferase activity. FIG. 12 shows that Chol-GL2 inhibited luciferase gene activity in a dose-dependent manner. InvA refers to chol-GL2 in inverted sequence.

Example 10

Figure 13:
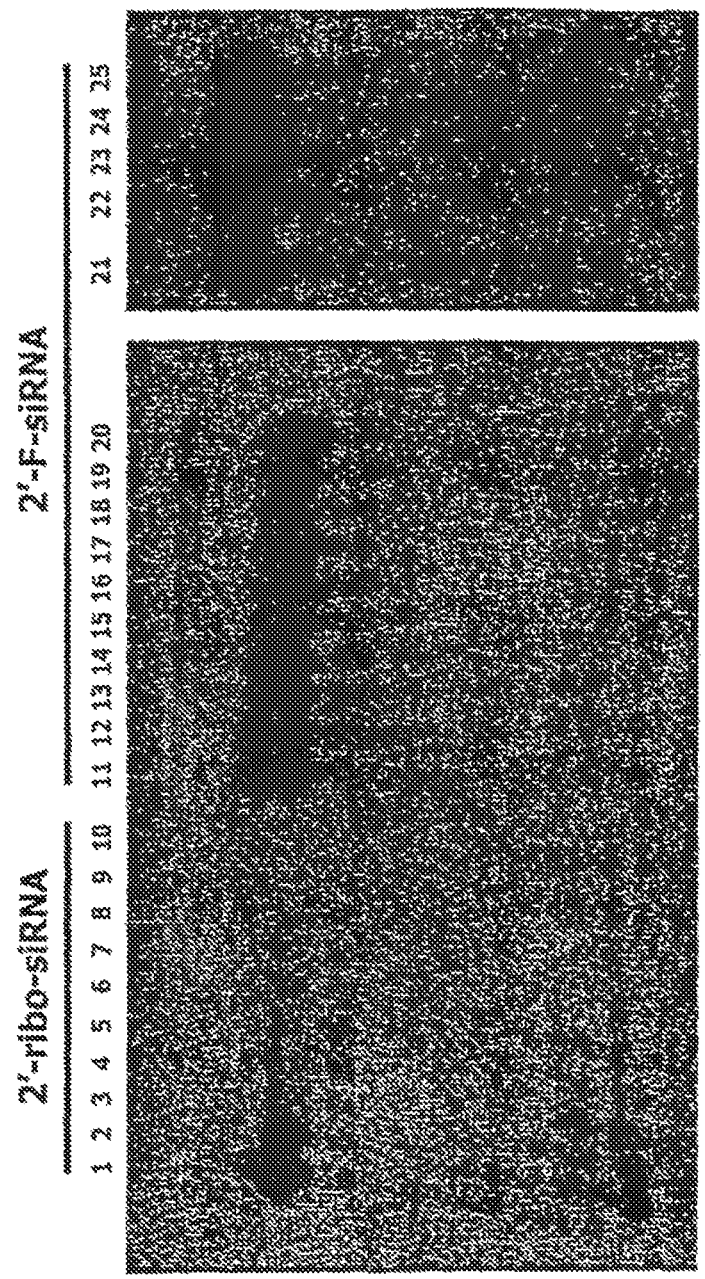
FIG. 13 depicts an autoradiograph of 5'-labeled siRNA duplexes separated by PAGE, and shows the stability of 2'-fluoro-modified siRNA (2'-F-GL2) incubated in human serum for up to 10 days. The siRNA duplexes were subjected to incubation with human serum and analysis by 20% PAGE. The composition of the lanes is as follows: Lanes 1, 11 and 21: $^{32}$P-end labeled siRNA alone; Lanes 2-10, 12-20 and 22-25: siRNA incubated with human serum. Lanes 2 & 12, 1 min; Lanes 3 & 13, 5 min; Lanes 4 & 14, 15 min; Lanes 5 & 15, 30 min; Lanes 6 & 16, 1 hr; Lanes 7 & 17, 2 hr; Lanes 8

To test the stability of 2' chemically modified siRNA compared to unmodified siRNA (siRNA), the following experiment is performed. Four nanograms of siRNA are added to a 20 μL volume of 80% human serum from a healthy donor. This mixture is incubated at 37 C.° for various times ranging from 1 minute up to 10 days. The results are depicted in lanes 2-10 of FIG. 13. The same process is performed for 2' fluorine modified siRNA (2'-F siRNA) as well and the results are shown in lanes 12-20 and 22-25 of FIG. 3. When the incubation process is finished, the mixtures are placed on ice and then immediately separated by PAGE along with a $^{32}$P-siRNA control (See Lanes 1, 11 and 21 of FIG. 13). The data show that the 2'-modified siRNA is stable over a period of 10 days as compared to unmodified siRNA.

Example 11

Figure 4:
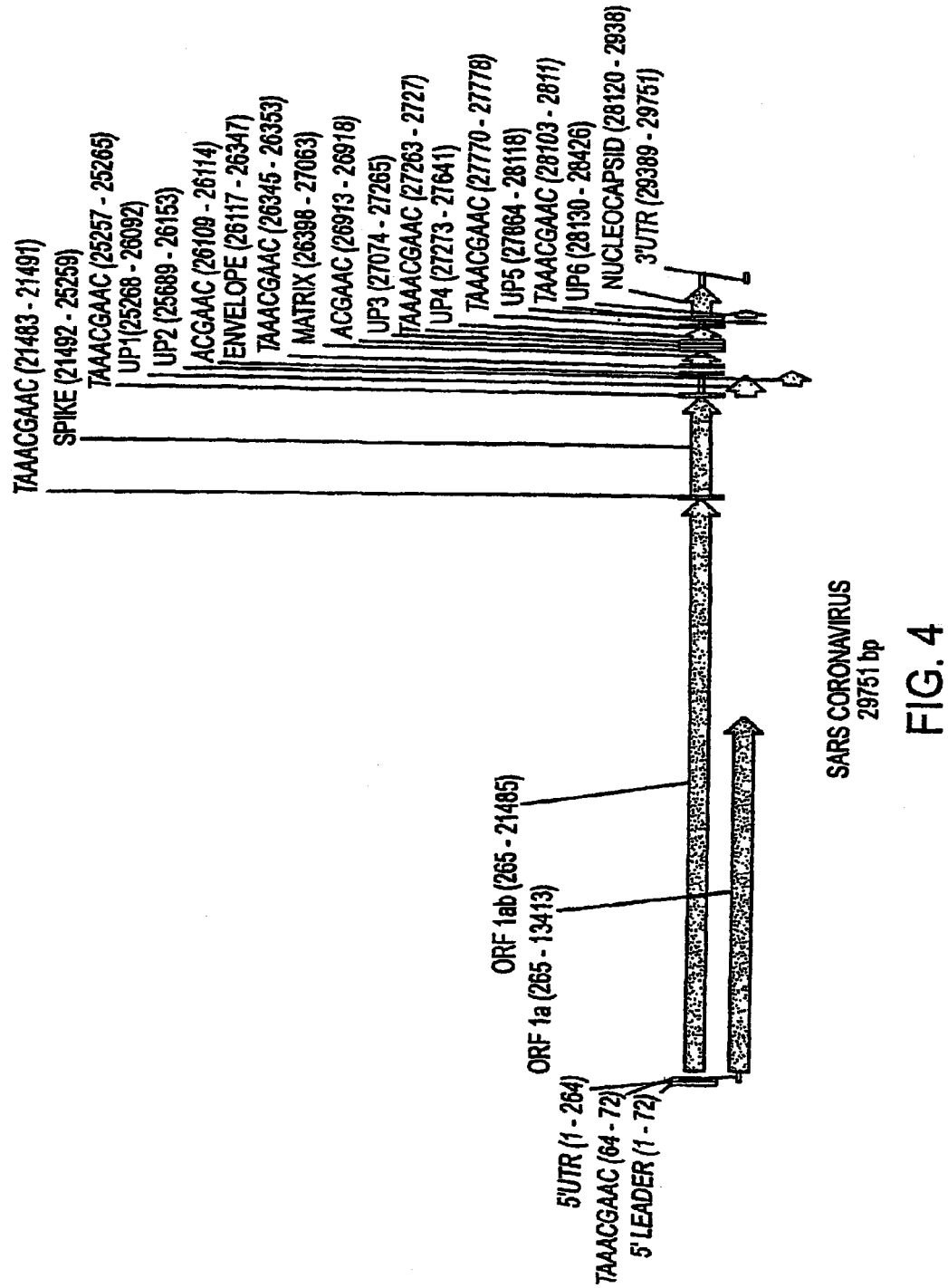
FIG. 4 is a schematic representation of the open reading frames of the SARS coronavirus (wherein "TAAAAC-GAAC" is represented by bases 27263-27272 of SEQ ID NO: 1).

To demonstrate the production of modified siRNA from long dsRNA, five micrograms of 1000 bp-long fluorinated dsRNAs (FIG. 14, panel (A)) were incubated overnight with 15 units of human Dicer at 37° C. The resulting diced-siRNAs were purified using a Sephadex G-25 column and electrophoresed on 20% PAGE (FIG. 14, panel (B)). FIG. 4 shows that recombinant human dicer effectively converts fluorinated-dsRNA into 2'F-siRNA.

Example 12

To further test whether siRNAs directed to the HCV genome confer intracellular immunity against this human pathogen, the assay described in Example 1 was employed to test siRNAC1, siRNAC2, siRNA5B1, siRNA5B2, and siRNA5B4, each of which is shown in FIG. 2. Each siRNA was tested at concentrations of 1 nM, 10 nM and 100 nM. As shown in FIG. 15, each of the siRNAs significantly inhibited luciferase activity in a dose-dependent manner. SiRNAC2 exhibited particular effectiveness.

Example 13

As a follow-up to the experiments reported in Example 9, assays were performed to demonstrate that the cholesterol modification, and not the fluoro modification directed siRNA molecules to Huh-7 liver cells. Huh-7 cells were incubated with various concentrations of two kinds of Chol-GL2 siRNAs: one having a 2'-fluoro modification and the other lacking such a modification. The results, shown in FIG. 16 demonstrate that the deliver of cholesterol-modified siRNA molecules to liver cells is due to the cholesterol, and not other modifications.

Example 14 siRNA was modified to include 2-Fluoro pyrimidines in place of all of the pyrimidines (2'-F-siRNA). This 2'-F-siRNA was further modified to include a two base deoxynucleotide "TT" sequence added to the 3' ends of the molecule in place of the ribolucleotide "UU" overhangs present in 2-F-siRNA (2'-F-siRNA 3'-X). FIG. 17 demonstrates that the further modification of the 2' fluorinated siRNA to include a 3'"dTdT" terminus resulted in significant increase in stability of the siRNA in human serum.

What is claimed is:

1. A method for inhibiting Hepatitis C Virus (HCV) replication in a patient, the method comprising the steps of:

(a) administering to said patient a composition comprising a modified double-stranded RNA (dsRNA) or modified small interfering RNA (siRNA) in an amount effective to mediate RNA interference and to inhibit HCV replication, wherein the modified dsRNA or modified siRNA comprises a first strand and a second strand, wherein the first and second strand are each no more than about 30 ribonucleotides in length and wherein the first or second strand targets HCV and is complementary to a target sequence of the HCV genome at least 15-25 nucleotides long; and wherein the modified dsRNA or modified siRNA is cholesterol-labeled, and (b) administering to said patient a cholesterol-lowering drug in an amount sufficient to reduce the level of competing cholesterol in the serum and allow more efficient uptake of the cholesterol-labeled modified dsRNA or modified siRNA by hepatocytes, wherein steps (a) and (b) can be performed simultaneously or in any order, and (c) wherein the cholesterol-lowering drug reduces the level of competing cholesterol in the serum, allowing more efficient uptake of the cholesterol-labeled modified dsRNA or modified siRNA by hepatocytes.

2. The method of claim 1, wherein said cholesterol-lowering drug is a statin, resin, nicotinic acid, gemfibrozil or clofibrate.

3. The method of claim 1, wherein said cholesterol-lowering drug is a statin.

4. The method of claim 1, wherein said modified dsRNA or modified siRNA is 2' modified.

5. The method of claim 1, wherein said modified dsRNA or modified siRNA is modified with a modification selected from the group consisting of fluoro-, methyl-, methoxyethyl- and propyl-modification.

6. The method of claim 5, wherein said fluoro-modification is a 2'-fluoro-modification or a 2',2'-difluoro-modification.

7. The method of claim 1, wherein at least one pyrimidine of said modified dsRNA or modified siRNA is modified, and said pyrimidine is cytosine, a derivative of cytosine, uracil, or a derivative of uracil.

8. The method of claim 1, wherein all of the pyrimidines in said modified dsRNA or modified siRNA are modified.

9. The method of claim 1, wherein said modified dsRNA or modified siRNA comprises a two base deoxynucleotide "TT" sequence at least one 3' end.

10. A method for inhibiting Hepatitis C Virus (HCV) replication in a patient, the method comprising the steps of:

(a) administering to said patient a composition comprising a modified double-stranded RNA (dsRNA) or modified small interfering RNA (siRNA) in an amount effective to mediate RNA interference and to inhibit HCV replication, wherein the modified dsRNA or modified siRNA comprises a first strand and a second strand, wherein the first and second strand are each no more than about 30 ribonucleotides in length and wherein the first or second strand targets HCV and is complementary to a target sequence of the HCV genome at least 15-25 nucleotides long; and wherein the modified dsRNA or modified siRNA is cholesterol-labeled, and (b) administering to said patient a cholesterol-lowering drug in an amount sufficient to reduce the level of competing cholesterol in the serum and allow more efficient uptake of the cholesterol-labeled modified dsRNA or modified siRNA by hepatocytes, wherein steps (a) and (b) are performed simultaneously, and (c) wherein the cholesterol-lowering drug reduces the level of competing cholesterol in the serum, allowing more efficient uptake of the cholesterol-labeled modified dsRNA or modified siRNA by hepatocytes.

11. The method of claim 10, wherein said cholesterol-lowering drug is a statin, resin, nicotinic acid, gemfibrozil or clofibrate.

12. The method of claim 10, wherein said cholesterol-lowering drug is a statin.

13. The method of claim 10, wherein said modified dsRNA or modified siRNA is 2' modified.

14. The method of claim 10, wherein said modified dsRNA or modified siRNA is modified with a modification selected from the group consisting of fluoro-, methyl-, methoxyethyl- and propyl-modification.

15. The method of claim 14, wherein said fluoro-modification is a 2'-fluoro-modification or a 2',2'-difluoro-modification.

16. The method of claim 10, wherein at least one pyrimidine of said modified dsRNA or modified siRNA is modified, and said pyrimidine is cytosine, a derivative of cytosine, uracil, or a derivative of uracil.

17. The method of claim 10, wherein all of the pyrimidines in said modified dsRNA or modified siRNA are modified.

18. The method of claim 10, wherein said modified dsRNA or modified siRNA comprises a two base deoxynucleotide "TT" sequence at least one 3' end.

* * * * *